(12) United States Patent
Zweckstetter et al.

(10) Patent No.: US 9,253,964 B2
(45) Date of Patent: Feb. 9, 2016

(54) MUTANT ALPHA-SYNUCLEIN, AND METHODS USING SAME

(71) Applicant: **Max-Planck-Gesellschaft zur För ated disorders of the central nervous
MUTANT ALPHA-SYNUCLEIN, AND METHODS USING SAME This application is a Divisional application of U.S. patent application Ser. No. 13/057,680, filed Aug. 12, 2011, which is a National Stage application of International Application No. PCT/EP2009/060299 filed Aug. 7, 2009, the entire contents of which is hereby incorporated herein by reference. This application also claims priority under 35 U.S.C. §119 to European Patent Application No. 08162056.9, filed Aug. 8, 2008, the entire contents of which is hereby incorporated herein by reference.

The invention relates to mutant alpha-synuclein with increased toxicity compared to wildtype alpha-synuclein. In particular, the invention relates to a mutant human alpha-synuclein, or a homologue thereof, comprising at least one amino acid substitution selected from the group consisting of a substitution at the alanine at position 56 (A56), at the alanine at position 76 (A76), at the methionine at position 127 (M127) and/or at the valine at position 118 (V118). The invention also provides polynucleotides and expression vectors encoding the mutant alpha-synuclein or homologue thereof, as well as cells comprising the polynucleotide or expression vector. Finally, the invention provides a non-human animal comprising the mutant alpha-synuclein or homologue thereof. Such cells and non-human animals are particularly useful for identifying substances that might prevent or reduce the toxicity of alpha-synuclein.

BACKGROUND OF THE INVENTION

Parkinson's disease (PD) and several other neurodegenerative diseases are degenerative disorders of the central nervous system and are both chronic and progressive. The prevalence of PD in Europeans is 1.6% in persons over 65 years of age. However, more than 10% of the patients are diagnosed before the age of 50. In 1990, an estimated 4 million people were suffering from PD. It is characterized by muscle rigidity, tremor, a slowing of physical movement (bradykinesia) and, in extreme cases, a loss of physical movement (akinesia). The primary symptoms are the results of decreased stimulation of the motor cortex by the basal ganglia, normally caused by the insufficient formation and action of dopamine, which is produced in the dopaminergic neurons of the brain. Secondary symptoms may include high level cognitive dysfunction and subtle language problems. Typical other symptoms include disorders of mood, behavior, thinking, and sensation (non-motor symptoms). Patients' individual symptoms may be quite dissimilar and progression of the disease is also distinctly individual.

The symptoms of Parkinson's disease result from the loss of dopaminergic cells in the region of the substantia nigra pars compacta. These neurons project to the striatum and their loss leads to alterations in the activity of the neural circuits within the basal ganglia that regulate movement, in essence an inhibition of the direct pathway (facilitating movement) and excitation of the indirect pathway (inhibiting movement). The lack of dopamine results in increased inhibition of the ventral anterior nucleus of the thalamus, which sends excitatory projections to the motor cortex, thus leading to hypokinesia.

The pathological hallmark feature of Parkinson's disease (PD) and several other neurodegenerative disorders is the deposition of intracytoplasmic neuronal inclusions termed Lewy bodies. The major component of Lewy bodies are amyloid fibrils of the protein alpha-synuclein (alpha-S). Protecting neurons from the toxicity of alpha-synuclein is a promising strategy for treating these diseases.

Related diseases (sometimes called Parkinson-plus diseases) include dementia with Lewy bodies (DLB). While idiopathic Parkinson's disease patients also have Lewy bodies in their brain tissue, the distribution is denser and more widespread in DLB. Even so, the relationship between Parkinson disease, Parkinson disease with dementia (PDD), and dementia with Lewy bodies (DLB) might be most accurately conceptualized as a spectrum, with a discrete area of overlap between each of the three disorders. The common involvement of alpha-synuclein in diseases such as PD, PDD, multiple system atrophy and the Lewy body variant of Alzheimer's disease has led to a classification of these disease under the term synucleinopathies.

Mutations of alpha-S associated with familial PD (A30P, A53T, E46K) have an increased aggregation propensity in vitro (US 2007/0213253), in agreement with aggregation of alpha-S into fibrillar Lewy bodies in vivo. However, the role different aggregated alpha-S species play for neurotoxicity in vivo is unclear. Loss of dopaminergic terminals was observed in the presence of non-fibrillar alpha-S inclusions in one line of A53T alpha-S transgenic mice (Masliah et al. *Science* 287, 1265-1269 (2000)), raising the possibility that pre-fibrillar intermediates in the alpha-S aggregation process may be pathogenic (Lashuel & Lansbury *Q Rev Biophys* 39, 167-201 (2006)), potentially by pore formation in cell membranes. However, transgenic mice overexpressing A30P alpha-S failed to exhibit neurodegeneration (Lee et al. *Proc Natl Acad Sci USA* 99, 8968-8973 (2002)), despite the fact that A30P alpha-S delays conversion of pre-fibrillar aggregates to fibrils (Conway et al., supra). Thus, the A30P alpha-S mice provided in vivo support that pre-fibrillar alpha-S is not the primary toxic moiety.

US 2007/0192879 and WO 2008/063779 describe animal models and cell models overexpressing alpha-S. The only disclosed mutations are A30P, A53T and E46K, which are known to show an increased aggregation propensity.

US 2007/0213253 disclose several synuclein mutants having aggregation-inhibitory activity. Those mutants are supposed to be capable of inhibiting aggregation of wt alpha-S.

Also, Koo et al. *Biochem. Biophys. Res. Comm.* 368, 772-778 (2008) describe substitutions of alpha-synuclein which exhibit the capability to influence fibril formation of the protein.

Zhou et al. *J. Biol. Chem.* 283(15), 9863-9870 (2008) teaches tyrosine to cysteine substitutions in human alpha-synuclein showing enhanced alpha-synuclein fibril formation and neurotoxicity.

Thus, there is a need in the art for alpha-synuclein mutants that can be used in in vivo and in vitro screening assays in order to identify substances that can prevent or reduce the toxicity of alpha-synuclein, which plays a pivotal role in the pathology of synucleinopathies.

SUMMARY OF THE INVENTION

Accordingly, the present invention relates to a mutant human alpha-synuclein with increased toxicity compared to wild-type alpha-synuclein, or a homologue thereof, wherein the mutant alpha-synuclein or homologue thereof comprises at least one amino acid substitution selected from the group consisting of a substitution at the alanine at position 56 (A56), at the alanine at position 76 (A76), at the methionine at position 127 (M127) and/or at the valine at position 118 (V118), as defined in the claims. Further, the invention relates to a polynucleotide encoding the mutant alpha-synuclein or homologue thereof, or an expression vector comprising said polynucleotide, a cell comprising the polynucleotide or expression vector, as defined in the claims. Also, a non-human animal comprising the cell of the invention is provided, as defined in the claims. Finally, the invention provides methods for identifying a substance that prevents or reduces toxicity of alpha-synuclein, as defined in the claims.

DETAILED DESCRIPTION OF THE PREFERRED EMBODIMENTS

Little is known about the pathogenicity and the mechanism of toxicity of aggregated alpha-S species, in particular in neuronal cells. To address these questions, the inventors generated alpha-S variants by a structure-based rational design and tested their biophysical and functional properties with respect to both fibril formation in vitro and their in vivo effect on neuronal activity and survival (toxicity) in four different model systems for PD, including both invertebrates (*Caenorhabditis elegans, Drosophila melanogaster*) and mammalian neurons. Surprisingly, it was found that the designed alpha-S variants of the invention form soluble oligomers of defined sizes but cause indeed a dramatic delay in fibril formation. Expression of pre-fibrillar alpha-S mutants in animal PD models affects locomotion, sleeping behaviour as well as the lifespan of the animals, and causes neuronal toxicity.

The results shown herein provide insights into the role of multimeric alpha-S species for PD pathogenesis and establish a tight link between the biophysical properties of the alpha-S species and their function in different in vivo models. The newly established toxicity model and animal models for alpha-S species provide a powerful tool for the identification of potential therapeutic compounds.

Thus, in a first aspect, the present invention relates to a mutant alpha-synuclein with increased toxicity compared to wild-type alpha-synuclein having the amino acid sequence shown in SEQ ID NO: 1, or a homologue thereof, wherein the mutant alpha-synuclein or homologue thereof comprises at least one amino acid substitution selected from the group consisting of a substitution at the alanine at position 56 (A56), at the alanine at position 76 (A76), at the methionine at position 127 (M127) and/or at the valine at position 118 (V118).

The present invention contemplates a mutant alpha-synuclein with decreased fibril formation ability compared to wild-type alpha-synuclein having the amino acid sequence shown in SEQ ID NO: 1, or a homologue thereof, wherein the mutant alpha-synuclein or homologue thereof comprises at least one amino acid substitution selected from the group consisting of a substitution at the alanine at position 56 (A56), at the alanine at position 76 (A76), at the methionine at position 127 (M127) and/or at the valine at position 118 (V118).

The present invention further contemplates a mutant alpha-synuclein with increased toxicity and decreased fibril formation ability compared to wild-type alpha-synuclein having the amino acid sequence shown in SEQ ID NO: 1, or a homologue thereof, wherein the mutant alpha-synuclein or homologue thereof comprises at least one amino acid substitution selected from the group consisting of a substitution at the alanine at position 56 (A56), at the alanine at position 76 (A76), at the methionine at position 127 (M127) and/or at the valine at position 118 (V118).

The present invention also contemplates a mutant alpha-synuclein with increased toxicity compared to wild-type alpha-synuclein having the amino acid sequence shown in SEQ ID NO: 1, or a homologue thereof, wherein the mutant alpha-synuclein or homologue thereof comprises an amino acid substitution at the alanine at position 56 (A56) and/or at the alanine at position 76 (A76).

Also, a mutant alpha-synuclein with decreased fibril formation ability compared to wild-type alpha-synuclein having the amino acid sequence shown in SEQ ID NO: 1, or a homologue thereof, wherein the mutant alpha-synuclein or homologue thereof comprises an amino acid substitution at the alanine at position 56 (A56) and/or at the alanine at position 76 (A76) is contemplated.

In addition, a mutant alpha-synuclein with increased toxicity and decreased fibril formation ability compared to wild-type alpha-synuclein having the amino acid sequence shown in SEQ ID NO: 1, or a homologue thereof, wherein the mutant alpha-synuclein or homologue thereof comprises an amino acid substitution at the alanine at position 56 (A56) and/or at the alanine at position 76 (A76), is contemplated.

Thus, the mutant alpha-synuclein or homologue may comprise an amino acid substitution at the alanine at position 56 (or at an amino acid in the corresponding position of the homologue) of SEQ ID NO: 1. The mutant alpha-synuclein or homologue of the first aspect may also comprise an amino acid substitution at the alanine at position 76 (or at an amino acid in the corresponding position of the homologue) of SEQ ID NO: 1. The mutant alpha-synuclein or homologue of the first aspect may comprise an amino acid substitution at the alanine at position 56 (or at an amino acid in the corresponding position of the homologue) and an amino acid substitution at the alanine at position 76 (or at an amino acid in the corresponding position of the homologue) of SEQ ID NO: 1.

In one preferred embodiment of the present invention, the mutant or homologue comprises an amino acid substitution at the alanine at position 56 (A56) and at the alanine at position 76 (A76).

Also, the present invention contemplates a mutant alpha-synuclein with increased toxicity compared to wild-type alpha-synuclein having the amino acid sequence shown in SEQ ID NO: 1, or a homologue thereof, wherein the mutant alpha-synuclein comprises an amino acid substitution at the methionine at position 127 (M127) and/or the valine at position 118 (V118), preferably wherein the methionine at position 127 and/or the valine in the position 118 is substituted by alanine (A), glutamic acid (E), or aspartic acid (D), more preferably by alanine (A).

In addition, a mutant alpha-synuclein with increased toxicity and decreased fibril formation ability compared to wild-type having the amino acid sequence shown in SEQ ID NO: 1, or a homologue thereof, wherein the mutant alpha-synuclein or homologue thereof comprises an amino acid substitution at the methionine at position 127 (M127) and/or the valine at position 118 (V118), preferably wherein the methionine at position 127 and/or the valine in the position 118 is substituted by alanine (A), glutamic acid (E), or aspartic acid (D), more preferably by alanine (A) is contemplated.

In one preferred embodiment of the present invention, the mutant or homologue comprises an amino acid substitution at the methionine at position 127 (M127) and at the valine at position 118 (V118).

It is also contemplated that these substitutions may be combined with any of the other embodiments described herein.

A mutant alpha-synuclein according to the invention relates to a polypeptide having at least 70% amino acid sequence identity on the amino acid level to SEQ ID NO: 1. Preferably, the mutant alpha-synuclein has at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5% amino acid sequence identity to SEQ ID NO: 1.

The term "mutant" alpha-synuclein implies that at least one single amino acid residue of the alpha-synuclein molecule is deleted, inserted, or replaced by another amino acid residue. The techniques of molecular biology to generate these deletions, insertions or substitutions are well-known in the art. Typically, the mutant alpha-synuclein does not have 100% amino acid sequence identity to SEQ ID NO: 1. However, there may be cases in which a program used for calculating sequence identity indicates 100% sequence identity between SEQ ID NO: 1 and another sequence of interest, even though these two sequences differ by at least one amino acid residue. In those cases, a mutant alpha-synuclein is present if there is a difference of at least one residue on the amino acid sequence level between the sequence of interest and SEQ ID NO: 1. Optionally, the mutant alpha-synuclein may be a fusion protein comprising a further protein component, such as a tag (e.g. for purification), a marker (e.g. for localization), or an inoperable part (e.g. resulting from genetic manipulation) etc.

A polypeptide has "at least X % identity" to SEQ ID NO: 1 if SEQ ID NO: 1 is aligned with the best matching sequence of a polypeptide of interest, and the amino acid identity between those two aligned sequences is at least X %. Such an alignment of amino acid sequences can be performed using, for example, publicly available computer homology programs such as the "BLAST" program provided on the NCBI homepage at www.ncbi.nlm.nih.gov/blast/blast.cgi, using the default settings provided therein. Further methods of calculating sequence identity percentages of sets of amino acid sequences or nucleic acid sequences are known in the art. The term "at position X", always refers to the amino acid numbering according to SEQ ID NO: 1. An alignment of the amino acid sequence of a homologue with SEQ ID NO: 1 allows determining a corresponding amino acid (residue) in the homologue, e.g. the corresponding amino acid residue(s) in the homologue to the amino acid residue(s) which is/are substituted in SEQ ID NO: 1.

A "homologue" refers to an isoform of the alpha-synuclein of SEQ ID NO: 1 or to an alpha-synuclein of a species other than human being evolutionary homologous to the alpha-synuclein of SEQ ID NO: 1. Typically, the homologue has at least 70% amino acid sequence identity on the amino acid level to SEQ ID NO: 1. Preferably, the mutant alpha-synuclein has at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5% or 100% (but still differing in at least one amino acid residue, see above) amino acid sequence identity to SEQ ID NO: 1. More preferably, the mutant homologue of alpha-synuclein exhibits at least 30%, at least 35%, at least 40%, at least 45%, at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 98.5%, at least 99%, at least 99.5% or 100% of the toxicity of mutant alpha-synuclein of SEQ ID NO: 1, wherein the toxicity can be determined as described below. Examples for homologues, which are not intended to be limiting, are the alpha-synuclein of *Pan troglodytes* (accession number XP_001162416.1), *Pan paniscus* (accession number AAQ85068.1), *Gorilla gorilla* (accession number AAQ85072.1), *Erythrocebus patas* (accession number AAQ85067.1), *Macaca fascicularis* (accession number AAQ85071.1), *Macaca mulatta* (accession number AAQ85074), *Pongo abelii* (accession number AAQ85070.1), *Saguinus labiatus* (accession number AAQ85075.1), *Sus scrofa* (accession number NP_001032222.1), *Lagothrix lagotricha* (accession number AAQ85073.1), *Ateles geoffroyi* (accession number AAQ85076.1), *Canis familiaris* (accession number XP_535656.1), *Rattus norvegicus* (accession number NP_062042.1), *Mus musculus* (accession number NP_001035916), *Bos Taurus* (accession number NP_001029213.1), *Equus caballus* (accession number XP_001496954.1), *Gallus gallus* (accession number NP_990004.1), *Taeniopygia guttata* (accession number NP_001041718.1), *Xenopus laevis* (accession number NP_001080623.1), and *Xenopus tropicalis* (accession number NP_001090876.1).

In addition, the mutant alpha-synuclein or homologue has an increased toxicity compared to wild-type alpha-synuclein. The term "toxicity" describes the capability to which the mutant alpha-synuclein is able to damage a cell (cytotoxicity), an organ (organotoxicity) or a whole organism. In case the cell which is specifically damaged is a neuronal cell, in an isolated form or as a part of an organ or organism, this type of toxicity is preferably called neurotoxicity. Thus, the term "toxicity" particularly encompasses the neurotoxicity of mutant alpha-synuclein. To test whether a mutant alpha-synuclein or homologue has an increased toxicity compared to wild-type alpha-synuclein, in vitro and in vivo assays can be performed.

For example, for an in vitro assay, a WST assay measuring mitochondrial dehydrogenase activity, can be performed according to the protocol of the manufacturer (Roche Diagnostics, Catalogue Number 1 644 807). By using a water-soluble tetrazolium salt (WST) colorimeteric assay for mitochondrial dehydrogenase activity, toxicity of a mutant alpha-synuclein or homologue thereof to wt alpha-synuclein, each transfected into a neuronal cell, can be compared with a control cell. The WST colorimeteric assay estimates not only the mitochondrial capacity to produce reduced equivalents but also the decline of mitochondrial activity due to diminished cell numbers. Primary neuronal cells from rat embryos at E18 or E16 are transduced by AAV vectors at day 3 (DIV 3) and analysed at DIV 10. An increased toxicity is evident if the cells transfected with the mutant-alpha-synuclein exhibit less than 90%, 85%, 80%, 75%, 70%, in particular less than 69%, 68%, 67%, 66%, 65%, 64%, 63%, 62%, 61%, 60%, 59%, 58%, 57%, 56%, 55% mitochondrial dehydrogenase activity of the wild-type when compared under identical conditions. Alternatively, toxicity may be determined in vitro by growth impairment of yeast cells transfected with the mutant alpha-synuclein, wild-type alpha-synuclein and a vector control, as described in Example 6.

Also, in vivo methods can be used for determining whether a mutant alpha-synuclein or homologue thereof has an increased toxicity compared to wild-type. For example, transgenic *C. elegans* expressing wild-type alpha-synuclein or a mutant may be generated as described by Pitman, J. L., et al. Nature 441, 753-756 (2006). To image dopaminergic neurons, the animals are anesthetized by 50 mM sodium azide in M9 buffer and mounted on a 2% agarose pad. RFP positive dopaminergic neurons are visualized using a Leica SP2 confocal microscope system. Neurite defects are scored positive if one or more dendritic processes out of four have degenerated. An increased toxicity is evident if less than 80%, 75%, 70%, 65%, 60%, in particular 58%, 56%, 54%, 52%, 50%, 48%, 46%, 44%, 42%, 40%, 38%, 36%, 34%, 32%, 30%, 28%, 26%, 24%, 22%, 20%, 18%, 16% of the worms expressing the mutant-alpha-synuclein are lacking neurite defects when compared to the worms expressing wild-type alpha-synuclein under identical conditions.

In another preferred embodiment, the mutant or homologue of the invention may further comprise the substitution A30P.

The alanine at position 56 and/or the alanine at position 76 may be substituted by any amino acid other than alanine, or, in case of a homologue, any amino acid other than the corresponding amino acid in the homologue. Preferably the substitution is a non-conservative substitution, in particular wherein the alanine at position 56 and/or the alanine at position 76 is substituted by glutamic acid (E), aspartic acid (D), or a proline (P) residue, preferably by a proline residue.

A "conservative" amino acid exchange encompasses a conservative substitution of one residue by one of a certain set of other residues, such as indicated in the table below. Thus, if an alanine at the position 56 or 76 of an alpha-synuclein molecule of the invention is substituted by a non-conservative amino acid, Ala is substituted by an amino acid other than Gly, Ser, or Thr. Preferably, the alanine is substituted by Glu (E), Asp (D), or Pro (P), and even more preferably, the alanine is substituted by Pro (P). Thus preferred substitutions are A56D, A56E, A56P, A76D, A76E, A76P, A56D+A76D, A56D+A76E, A56D+A76P, A56E+A76D, A56E+A76E, A56E+A76P, A56P+A76E, A56P+A76D, A56P+A76P, more preferred substitutions are A56D+A76P, A56E+A76P, A56P+A76E, A56P+A76D, A56P+A76P, and most preferred substitutions are A56P, A76P, and A56P+A76P.

| Amino acid | Conservative substitution |
| --- | --- |
| A | G; S; T |
| C | A; V; L |
| D | E; N; Q |
| E | D; Q; N |
| F | W; Y; L; M; H |
| G | A |
| H | Y; F; K; R |
| I | V; L; M; A |
| K | R; H |
| L | M; I; V; A |
| M | L; I; V; A |
| N | Q |
| P | V; I |
| Q | N |
| R | K; H |
| S | A; T; G; N |
| T | A; S; G; N; V |
| V | A; L; I |
| W | F; Y; H |
| Y | F; W; H |

In still another preferred embodiment, the substitution is a non-conservative substitution or a substitution by alanine, in particular wherein the methionine at position 127 and/or the valine in the position 118 is substituted by alanine (A), glutamic acid (E), or aspartic acid (D), more preferably by alanine (A). This means that any of the above mentioned substitutions or combination of substitutions, either comprising the substitution A30P or not, may further comprise a substitution at position M127 and/or V118, i.e. a substitution at position M127, or a substitution at position V118, or a substitution at position M127 and V118 of SEQ ID NO: 1, or at the corresponding amino acid position(s) of the homologue. M127 and/or V118 may be substituted by any amino acid other than methionine or valine, respectively, or any amino acid other than the corresponding amino acid in the homologue. However, preferred substitutions are M127A, M127E, M127D, V118A, V118E, V188D, M127A+V118A, M127A+V118E, M127A+V188D, M127E+V118A, M127E+V118E, M127E+V118D, M127D+V118A, M127D+V118E, M127D+V118D, even more preferred substitutions are M127A, V118A, M127A+V118A, M127A+V118E, M127A+V118D, M127E+V118A, M127D+V118A and most preferred substitutions are M127A, V118A, M127A+V118A.

Further preferred substitutions are:

A56D+M127A, A56E+M127A, A56P+M127A, A76D+M127A, A76E+M127A, A76P+M127A, A56D+A76D+M127A, A56D+A76E+M127A, A56D+A76P+M127A, A56E+A76D+M127A, A56E+A76E+M127A, A56E+A76P+M127A, A56P+A76E+M127A, A56P+A76D+M127A, A56P+A76P+M127A, A56D+A76P+M127A, A56E+A76P+M127A, A56P+A76E+M127A, A56P+A76D+M127A, A56P+A76P+M127A, A56P+M127A, A76P+M127A, A56P+A76P+M127A,

A56D+M127E, A56E+M127E, A56P+M127E, A76D+M127E, A76E+M127E, A76P+M127E, A56D+A76D+M127E, A56D+A76E+M127E, A56D+A76P+M127E, A56E+A76D+M127E, A56E+A76E+M127E, A56E+A76P+M127E, A56P+A76E+M127E, A56P+A76D+M127E, A56P+A76P+M127E, A56D+A76P+M127E, A56E+A76P+M127E, A56P+A76E+M127E, A56P+A76D+M127E, A56P+A76P+M127E, A56P+M127E, A76P+M127E, A56P+A76P+M127E,

A56D+M127D, A56E+M127D, A56P+M127D, A76D+M127D, A76E+M127D, A76P+M127D, A56D+A76D+M127D, A56D+A76E+M127D, A56D+A76P+M127D, A56E+A76D+M127D, A56E+A76E+M127D, A56E+A76P+M127D, A56P+A76E+M127D, A56P+A76D+M127D, A56P+A76P+M127D, A56D+A76P+M127D, A56E+A76P+M127D, A56P+A76E+M127D, A56P+A76D+M127D, A56P+A76P+M127D, A56P+M127D, A76P+M127D, A56P+A76P+M127D,

A56D+V118A, A56E+V118A, A56P+V118A, A76D+V118A, A76E+V118A, A76P+V118A, A56D+A76D+V118A, A56D+A76E+V118A, A56D+A76P+V118A, A56E+A76D+V118A, A56E+A76E+V118A, A56E+A76P+V118A, A56P+A76E+V118A, A56P+A76D+V118A, A56P+A76P+V118A, A56D+A76P+V118A, A56E+A76P+V118A, A56P+A76E+V118A, A56P+A76D+V118A, A56P+A76P+V118A, A56P+V118A, A76P+V118A, A56P+A76P+V118A,

A56D+V118E, A56E+V118E, A56P+V118E, A76D+V118E, A76E+V118E, A76P+V118E, A56D+A76D+V118E, A56D+A76E+V118E, A56D+A76P+V118E, A56E+A76D+V118E, A56E+A76E+V118E, A56E+A76P+V118E, A56P+A76E+V118E, A56P+A76D+V118E, A56P+A76P+V118E, A56D+A76P+V118E, A56E+A76P+V118E, A56P+A76E+V118E, A56P+A76D+V118E, A56P+A76P+V118E, A56P+V118E, A76P+V118E, A56P+A76P+V118E,

A56D+V118D, A56E+V118D, A56P+V118D, A76D+V118D, A76E+V118D, A76P+V118D, A56D+A76D+V118D, A56D+A76E+V118D, A56D+A76P+V118D, A56E+A76D+V118D, A56E+A76E+V118D, A56E+A76P+V118D, A56P+A76E+V118D, A56P+A76D+V118D, A56P+A76P+V118D, A56E+A76P+V118D, A56D+A76P+V118D, A56P+A76E+V118D, A56P+A76D+V118D, A56P+A76P+V118D, A56P+V118D, A76P+V118D, A56P+A76P+V118D,

A56D+M127A+V118A, A56E+M127A+V118A, A56P+
M127A+V118A, A76D+M127A+V118A, A76E+M127A+
V118A, A76P+M127A+V118A, A56D+A76D+M127A+
V118A, A56D+A76E+M127A+V118A, A56D+A76P+
M127A+V118A, A56E+A76D+M127A+V118A, A56E+
A76E+M127A+V118A, A56E+A76P+M127A+V118A,
A56P+A76E+M127A+V118A, A56P+A76D+M127A+
V118A, A56P+A76P+M127A+V118A, A56D+A76P+
M127A+V118A, A56E+A76P+M127A+V118A, A56P+
A76E+M127A+V118A, A56P+A76D+M127A+V118A,
A56P+A76P+M127A+V118A, A56P+M127A+V118A,
A76P+M127A+V118A, A56P+A76P+M127A+V118A,

A56D+M127A+V118E, A56E+M127A+V118E, A56P+
M127A+V118E, A76D+M127A+V118E, A76E+M127A+
V118E, A76P+M127A+V118E, A56D+A76D+M127A+
V118E, A56D+A76E+M127A+V118E, A56D+A76P+
M127A+V118E, A56E+A76D+M127A+V118E, A56E+
A76E+M127A+V118E, A56E+A76P+M127A+V118E,
A56P+A76E+M127A+V118E, A56P+A76D+M127A+
V118E, A56P+A76P+M127A+V118E, A56D+A76P+
M127A+V118E, A56E+A76P+M127A+V118E, A56P+
A76E+M127A+V118E, A56P+A76D+M127A+V118E,
A56P+A76P+M127A+V118E, A56P+M127A+V118E,
A76P+M127A+V118E, A56P+A76P+M127A+V118E,

A56D+M127A+V118D, A56E+M127A+V118D, A56P+
M127A+V118D, A76D+M127A+V118D, A76E+M127A+
V118D, A76P+M127A+V118D, A56D+A76D+M127A+
V118D, A56D+A76E+M127A+V118D, A56D+A76P+
M127A+V118D, A56E+A76D+M127A+V118D, A56E+
A76E+M127A+V118D, A56E+A76P+M127A+V118D,
A56P+A76E+M127A+V118D, A56P+A76D+M127A+
V118D, A56P+A76P+M127A+V118D, A56D+A76P+
M127A+V118D, A56E+A76P+M127A+V118D, A56P+
A76E+M127A+V118D, A56P+A76D+M127A+V118D,
A56P+A76P+M127A+V118D, A56P+M127A+V118D,
A76P+M127A+V118D, A56P+A76P+M127A+V118D,

A56D+M127E+V118A, A56E+M127E+V118A, A56P+
M127E+V118A, A76D+M127E+V118A, A76E+M127E+
V118A, A76P+M127E+V118A, A56D+A76D+M127E+
V118A, A56D+A76E+M127E+V118A, A56D+A76P+
M127E+V118A, A56E+A76D+M127E+V118A, A56E+
A76E+M127E+V118A, A56E+A76P+M127E+V118A,
A56P+A76E+M127E+V118A, A56P+A76D+M127E+
V118A, A56P+A76P+M127E+V118A, A56D+A76P+
M127E+V118A, A56E+A76P+M127E+V118A, A56P+
A76E+M127E+V118A, A56P+A76D+M127E+V118A,
A56P+A76P+M127E+V118A, A56P+M127E+V118A,
A76P+M127E+V118A, A56P+A76P+M127E+V118A,

A56D+M127E+V118E, A56E+M127E+V118E, A56P+
M127E+V118E, A76D+M127E+V118E, A76E+M127E+
V118E, A76P+M127E+V118E, A56D+A76D+M127E+
V118E, A56D+A76E+M127E+V118E, A56D+A76P+
M127E+V118E, A56E+A76D+M127E+V118E, A56E+
A76E+M127E+V118E, A56E+A76P+M127E+V118E,
A56P+A76E+M127E+V118E, A56P+A76D+M127E+
V118E, A56P+A76P+M127E+V118E, A56D+A76P+
M127E+V118E, A56E+A76P+M127E+V118E, A56P+
A76E+M127E+V118E, A56P+A76D+M127E+V118E,
A56P+A76P+M127E+V118E, A56P+M127E+V118E,
A76P+M127E+V118E, A56P+A76P+M127E+V118E,

A56D+M127E+V118D, A56E+M127E+V118D, A56P+
M127E+V118D, A76D+M127E+V118D, A76E+M127E+
V118D, A76P+M127E+V118D, A56D+A76D+M127E+
V118D, A56D+A76E+M127E+V118D, A56D+A76P+
M127E+V118D, A56E+A76D+M127E+V118D, A56E+
A76E+M127E+V118D, A56E+A76P+M127E+V118D,
A56P+A76E+M127E+V118D, A56P+A76D+M127E+
V118D, A56P+A76P+M127E+V118D, A56D+A76P+
M127E+V118D, A56E+A76P+M127E+V118D, A56P+
A76E+M127E+V118D, A56P+A76D+M127E+V118D,
A56P+A76P+M127E+V118D, A56P+M127E+V118D,
A76P+M127E+V118D, A56P+A76P+M127E+V118D,

A56D+M127D+V118A, A56E+M127D+V118A, A56P+
M127D+V118A, A76D+M127D+V118A, A76E+M127D+
V118A, A76P+M127D+V118A, A56D+A76D+M127D+
V118A, A56D+A76E+M127D+V118A, A56D+A76P+
M127D+V118A, A56E+A76D+M127D+V118A, A56E+A76E+M127D+V118A, A56E+A76P+M127D+V118A, A56P+A76E+M127D+V118A, A56P+A76D+M127D+V118A, A56P+A76P+M127D+V118A, A56D+A76P+M127D+V118A, A56E+A76P+M127D+V118A, A56P+A76E+M127D+V118A, A56P+A76D+M127D+V118A, A56P+A76P+M127D+V118A, A56P+M127D+V118A, A76P+M127D+V118A, A56P+A76P+M127D+V118A,

A56D+M127D+V118E, A56E+M127D+V118E, A56P+M127D+V118E, A76D+M127D+V118E, A76E+M127D+V118E, A76P+M127D+V118E, A56D+A76D+M127D+V118E, A56D+A76E+M127D+V118E, A56D+A76P+M127D+V118E, A56E+A76D+M127D+V118E, A56E+A76E+M127D+V118E, A56E+A76P+M127D+V118E, A56P+A76E+M127D+V118E, A56P+A76D+M127D+V118E, A56P+A76P+M127D+V118E, A56D+A76P+M127D+V118E, A56E+A76P+M127D+V118E, A56P+A76E+M127D+V118E, A56P+A76D+M127D+V118E, A56P+A76P+M127D+V118E, A56P+M127D+V118E, A76P+M127D+V118E, A56P+A76P+M127D+V118E,

A56D+M127D+V118D, A56E+M127D+V118D, A56P+M127D+V118D, A76D+M127D+V118D, A76E+M127D+V118D, A76P+M127D+V118D, A56D+A76D+M127D+V118D, A56D+A76E+M127D+V118D, A56D+A76P+M127D+V118D, A56E+A76D+M127D+V118D, A56E+A76E+M127D+V118D, A56E+A76P+M127D+V118D, A56P+A76E+M127D+V118D, A56P+A76D+M127D+V118D, A56P+A76P+M127D+V118D, A56D+A76P+M127D+V118D, A56E+A76P+M127D+V118D, A56P+A76E+M127D+V118D, A56P+A76D+M127D+V118D, A56P+A76P+M127D+V118D, A56P+M127D+V118D, A76P+M127D+V118D, A56P+A76P+M127D+V118D,

A56D+M127A+A30P, A56E+M127A+A30P, A56P+M127A+A30P, A76D+M127A+A30P, A76E+M127A+A30P, A76P+M127A+A30P, A56D+A76D+M127A+A30P, A56D+A76E+M127A+A30P, A56D+A76P+M127A+A30P, A56E+A76D+M127A+A30P, A56E+A76E+M127A+A30P, A56E+A76P+M127A+A30P, A56P+A76E+M127A+A30P, A56P+A76D+M127A+A30P, A56P+A76P+M127A+A30P, A56D+A76P+M127A+A30P, A56E+A76P+M127A+A30P, A56P+A76E+M127A+A30P, A56P+A76D+M127A+A30P, A56P+A76P+M127A+A30P, A56P+M127A+A30P, A76P+M127A+A30P, A56P+A76P+M127A+A30P,

A56D+M127E+A30P, A56E+M127E+A30P, A56P+M127E+A30P, A76D+M127E+A30P, A76E+M127E+A30P, A76P+M127E+A30P, A56D+A76D+M127E+A30P, A56D+A76E+M127E+A30P, A56D+A76P+M127E+A30P, A56E+A76D+M127E+A30P, A56E+A76E+M127E+A30P, A56E+A76P+M127E+A30P, A56P+A76E+M127E+A30P, A56P+A76D+M127E+A30P, A56P+A76P+M127E+A30P, A56D+A76P+M127E+A30P, A56E+A76P+M127E+A30P, A56P+A76E+M127E+A30P, A56P+A76D+M127E+A30P, A56P+A76P+M127E+A30P, A56P+M127E+A30P, A76P+M127E+A30P, A56P+A76P+M127E+A30P,

A56D+M127D+A30P, A56E+M127D+A30P, A56P+M127D+A30P, A76D+M127D+A30P, A76E+M127D+A30P, A76P+M127D+A30P, A56D+A76D+M127D+A30P, A56D+A76E+M127D+A30P, A56D+A76P+M127D+A30P,

A56E+A76D+M127D+A30P, A56E+A76E+M127D+A30P, A56E+A76P+M127D+A30P, A56P+A76E+M127D+A30P, A56P+A76D+M127D+A30P, A56P+A76P+M127D+A30P, A56D+A76P+M127D+A30P, A56E+A76P+M127D+A30P, A56P+A76E+M127D+A30P, A56P+A76D+M127D+A30P, A56P+A76P+M127D+A30P, A56P+M127D+A30P, A76P+M127D+A30P, A56P+A76P+M127D+A30P,

A56D+V118A+A30P, A56E+V118A+A30P, A56P+V118A+A30P, A76D+V118A+A30P, A76E+V118A+A30P, A76P+V118A+A30P, A56D+A76D+V118A+A30P, A56D+A76E+V118A+A30P, A56D+A76P+V118A+A30P, A56E+A76D+V118A+A30P, A56E+A76E+V118A+A30P, A56E+A76P+V118A+A30P, A56P+A76E+V118A+A30P, A56P+A76D+V118A+A30P, A56P+A76P+V118A+A30P, A56D+A76P+V118A+A30P, A56E+A76P+V118A+A30P, A56P+A76E+V118A+A30P, A56P+A76D+V118A+A30P, A56P+A76P+V118A+A30P, A56P+V118A+A30P, A76P+V118A+A30P, A56P+A76P+V118A+A30P,

A56D+V118E+A30P, A56E+V118E+A30P, A56P+V118E+A30P, A76D+V118E+A30P, A76E+V118E+A30P, A76P+V118E+A30P, A56D+A76D+V118E+A30P, A56D+A76E+V118E+A30P, A56D+A76P+V118E+A30P, A56E+A76D+V118E+A30P, A56E+A76E+V118E+A30P, A56E+A76P+V118E+A30P, A56P+A76D+V118E+A30P, A56P+A76E+V118E+A30P, A56D+A76P+V118E+A30P, A56E+A76P+V118E+A30P, A56P+A76E+V118E+A30P, A56P+A76D+V118E+A30P, A56P+A76P+V118E+A30P, A56P+V118E+A30P, A76P+V118E+A30P, A56P+A76P+V118E+A30P,

A56D+V118D+A30P, A56E+V118D+A30P, A56P+V118D+A30P, A76D+V118D+A30P, A76E+V118D+A30P, A76P+V118D+A30P, A56D+A76D+V118D+A30P, A56D+A76E+V118D+A30P, A56D+A76P+V118D+A30P, A56E+A76D+V118D+A30P, A56E+A76E+V118D+A30P, A56E+A76P+V118D+A30P, A56P+A76E+V118D+A30P, A56P+A76D+V118D+A30P, A56D+A76P+V118D+A30P, A56E+A76P+V118D+A30P, A56P+A76E+V118D+A30P, A56P+A76D+V118D+A30P, A56P+A76P+V118D+A30P, A56P+V118D+A30P, A76P+V118D+A30P, A56P+A76P+V118D+A30P,

A56D+M127A+V118A+A30P, A56E+M127A+V118A+A30P, A56P+M127A+V118A+A30P, A76D+M127A+V118A+A30P, A76E+M127A+V118A+A30P, A76P+M127A+V118A+A30P, A56D+A76D+M127A+V118A+A30P, A56D+A76E+M127A+V118A+A30P, A56D+A76P+M127A+V118A+A30P, A56E+A76D+M127A+V118A+A30P, A56E+A76E+M127A+V118A+A30P, A56E+A76P+M127A+V118A+A30P, A56P+A76E+M127A+V118A+A30P, A56P+A76D+M127A+V118A+A30P, A56P+A76P+M127A+V118A+A30P, A56D+A76P+M127A+V118A+A30P, A56E+A76P+M127A+V118A+A30P, A56P+A76E+M127A+V118A+A30P, A56P+A76D+M127A+V118A+A30P, A56P+A76P+M127A+V118A+A30P, A56P+M127A+V118A+A30P, A76P+M127A+V118A+A30P, A56P+A76P+M127A+V118A+A30P,

A56D+M127A+V118E+A30P, A56E+M127A+V118E+A30P, A56P+M127A+V118E+A30P, A76D+M127A+V118E+A30P, A76E+M127A+V118E+A30P, A76P+M127A+V118E+A30P, A56D+A76D+M127A+V118E+A30P, A56D+A76E+M127A+V118E+A30P, A56D+A76P+M127A+V118E+A30P, A56E+A76D+M127A+V118E+A30P, A56E+A76E+M127A+V118E+A30P, A56E+A76P+M127A+V118E+A30P, A56P+A76E+M127A+V118E+A30P, A56P+A76D+M127A+V118E+A30P, A56P+A76P+M127A+V118E+A30P, A56D+A76P+M127A+V118E+A30P, A56E+A76P+M127A+V118E+A30P, A56P+A76E+M127A+V118E+A30P, A56P+A76D+M127A+V118E+A30P, A56P+A76P+M127A+V118E+A30P, A56P+M127A+V118E+A30P, A76P+M127A+V118E+A30P, A56P+A76P+M127A+V118E+A30P,

A56D+M127A+V118D+A30P, A56E+M127A+V118D+A30P, A56P+M127A+V118D+A30P, A76D+M127A+V118D+A30P, A76E+M127A+V118D+A30P, A76P+M127A+V118D+A30P, A56D+A76D+M127A+V118D+A30P, A56D+A76E+M127A+V118D+A30P, A56D+A76P+M127A+V118D+A30P, A56E+A76D+M127A+V118D+A30P, A56E+A76E+M127A+V118D+A30P, A56E+A76P+M127A+V118D+A30P, A56P+A76E+M127A+V118D+A30P, A56P+A76D+M127A+V118D+A30P, A56P+A76P+M127A+V118D+A30P, A56D+A76P+M127A+V118D+A30P, A56E+A76P+M127A+V118D+A30P, A56P+A76E+M127A+V118D+A30P, A56P+A76D+M127A+V118D+A30P, A56P+A76P+M127A+V118D+A30P, A56P+M127A+V118D+A30P, A76P+M127A+V118D+A30P, A56P+A76P+M127A+V118D+A30P,

A56D+M127E+V118A+A30P, A56E+M127E+V118A+A30P, A56P+M127E+V118A+A30P, A76D+M127E+V118A+A30P, A76E+M127E+V118A+A30P, A76P+M127E+V118A+A30P, A56D+A76D+M127E+V118A+A30P, A56D+A76E+M127E+V118A+A30P, A56D+A76P+M127E+V118A+A30P, A56E+A76D+M127E+V118A+A30P, A56E+A76E+M127E+V118A+A30P, A56E+A76P+M127E+V118A+A30P, A56P+A76E+M127E+V118A+A30P, A56P+A76D+M127E+V118A+A30P, A56P+A76P+M127E+V118A+A30P, A56D+A76P+M127E+V118A+A30P, A56E+A76P+M127E+V118A+A30P, A56P+A76E+M127E+V118A+A30P, A56P+A76D+M127E+V118A+A30P, A56P+A76P+M127E+V118A+A30P, A56P+M127E+V118A+A30P, A76P+M127E+V118A+A30P, A56P+A76P+M127E+V118A+A30P,

A56D+M127E+V118E+A30P, A56E+M127E+V118E+A30P, A56P+M127E+V118E+A30P, A76D+M127E+V118E+A30P, A76E+M127E+V118E+A30P, A76P+M127E+V118E+A30P, A56D+A76D+M127E+V118E+A30P, A56D+A76E+M127E+V118E+A30P, A56D+A76P+M127E+V118E+A30P, A56E+A76D+M127E+V118E+A30P, A56E+A76E+M127E+V118E+A30P, A56E+A76P+M127E+V118E+A30P, A56P+A76E+M127E+V118E+A30P, A56P+A76D+M127E+V118E+A30P, A56P+A76P+M127E+V118E+A30P, A56D+A76P+M127E+V118E+A30P, A56E+A76P+M127E+V118E+A30P, A56P+A76E+M127E+V118E+A30P, A56P+A76D+M127E+V118E+A30P, A56P+A76P+M127E+V118E+A30P, A56P+M127E+V118E+A30P, A76P+M127E+V118E+A30P, A56P+A76P+M127E+V118E+A30P,

A56D+M127E+V118D+A30P, A56E+M127E+V118D+A30P, A56P+M127E+V118D+A30P, A76D+M127E+V118D+A30P, A76E+M127E+V118D+A30P, A76P+M127E+V118D+A30P, A56D+A76D+M127E+V118D+A30P, A56D+A76E+M127E+V118D+A30P, A56D+A76P+M127E+V118D+A30P, A56E+A76D+M127E+V118D+A30P, A56E+A76E+M127E+V118D+A30P, A56E+A76P+M127E+V118D+A30P, A56P+A76E+M127E+V118D+A30P, A56P+A76D+M127E+V118D+A30P, A56P+A76P+M127E+V118D+A30P, A56D+A76P+M127E+V118D+A30P, A56E+A76P+M127E+V118D+A30P, A56P+A76E+M127E+V118D+A30P, A56P+A76D+M127E+V118D+A30P, A56P+A76P+M127E+V118D+A30P, A56P+M127E+V118D+A30P, A76P+M127E+V118D+A30P, A56P+A76P+M127E+V118D+A30P,

A56D+M127D+V118A+A30P, A56E+M127D+V118A+A30P, A56P+M127D+V118A+A30P, A76D+M127D+V118A+A30P, A76E+M127D+V118A+A30P, A76P+M127D+V118A+A30P, A56D+A76D+M127D+V118A+

A30P, A56D+A76E+M127D+V118A+A30P, A56D+A76P+ M127D+V118A+A30P, A56E+A76D+M127D+V118A+ A30P, A56E+A76E+M127D+V118A+A30P, A56E+A76P+ M127D+V118A+A30P, A56P+A76E+M127D+V118A+ A30P, A56P+A76D+M127D+V118A+A30P, A56P+A76P+ M127D+V118A+A30P, A56D+A76P+M127D+V118A+ A30P, A56E+A76P+M127D+V118A+A30P, A56P+A76E+ M127D+V118A+A30P, A56P+A76D+M127D+V118A+ A30P, A56P+A76P+M127D+V118A+A30P, A56P+ M127D+V118A+A30P, A76P+M127D+V118A+A30P, A56P+A76P+M127D+V118A+A30P,

A56D+M127D+V118E+A30P, A56E+M127D+V118E+ A30P, A56P+M127D+V118E+A30P, A76D+M127D+ V118E+A30P, A76E+M127D+V118E+A30P, A76P+ M127D+V118E+A30P, A56D+A76D+M127D+V118E+ A30P, A56D+A76E+M127D+V118E+A30P, A56D+A76P+ M127D+V118E+A30P, A56E+A76D+M127D+V118E+ A30P, A56E+A76E+M127D+V118E+A30P, A56E+A76P+ M127D+V118E+A30P, A56P+A76E+M127D+V118E+ A30P, A56P+A76D+M127D+V118E+A30P, A56P+A76P+ M127D+V118E+A30P, A56D+A76P+M127D+V118E+ A30P, A56E+A76P+M127D+V118E+A30P, A56P+A76E+ M127D+V118E+A30P, A56P+A76D+M127D+V118E+ A30P, A56P+A76P+M127D+V118E+A30P, A56P+ M127D+V118E+A30P, A76P+M127D+V118E+A30P, A56P+A76P+M127D+V118E+A30P,

A56D+M127D+V118D+A30P, A56E+M127D+V118D+ A30P, A56P+M127D+V118D+A30P, A76D+M127D+ V118D+A30P, A76E+M127D+V118D+A30P, A76P+ M127D+V118D+A30P, A56D+A76D+M127D+V118D+ A30P, A56D+A76E+M127D+V118D+A30P, A56D+A76P+ M127D+V118D+A30P, A56E+A76D+M127D+V118D+ A30P, A56E+A76E+M127D+V118D+A30P, A56E+A76P+ M127D+V118D+A30P, A56P+A76E+M127D+V118D+ A30P, A56P+A76D+M127D+V118D+A30P, A56P+A76P+ M127D+V118D+A30P, A56D+A76P+M127D+V118D+ A30P, A56E+A76P+M127D+V118D+A30P, A56P+A76E+ M127D+V118D+A30P, A56P+A76D+M127D+V118D+ A30P, A56P+A76P+M127D+V118D+A30P, A56P+ M127D+V118D+A30P, A76P+M127D+V118D+A30P, A56P+A76P+M127D+V118D+A30P,

In addition to the mutation A30P in human alpha synuclein, also A53T and E46K are believed to be involved in the development of Parkinson's disease (US 2007/0213253).

Koo et al. *Biochem. Biophys. Res. Comm.* 368, 772-778 (2008) shows biophysical data substitutions of alpha-synuclein which exhibit the capability to influence fibril formation of the protein. In particular substitutions V37P, L38P, V40P, V48P, V49P, V52P, T59P, V63P, T64P, N65P, G67P, G68P, A69P, V70P, T72P, T75P, T81P, E83P, A89P, A90P showed delayed aggregation of the alpha-synuclein protein. Furthermore substitutions T72E, T75K, V95S and A78T have been found to delay fibril formation in vitro.

A human alpha-synuclein having a Y39C substitution was recently shown by Zhou et al. *J. Biol. Chem.* 283(15), 9863-9870 (2008) to enhance alpha-synuclein fibril formation and neurotoxicity.

US 2007/0213253 discloses substitutions in the human alpha-synuclein resulting in mutants with decreased ability of forming aggregation. In particular, the substitutions A50P, Gly68T, Gly68V, A69T, A69V, A69K, V70T, V70P, V70F, V71T, V71K, T72V, T72E, V74T, V77T and V82K are disclosed.

Moreover, further point mutations which influence fibrillation of alpha-synuclein are known: E13K, Q24K, E35K, Y39A, K45E, V40D, E61K, V66S, V66P, V70G, V74D, V74E, V74G, E83K, Y125A, Y133A, Y136A (Harada et al. *Biochim. Biophys. Acta*, Epub July 2009; Kumar et al. *Biochem. Biophys. Res. Commun*., Epub July 2009; Koo et al. *Biochem. Biophys. Res. Commun.* 386(1): 165-169 (2009); Ulrih et al. *Biochim. Biophys. Acta* 1782(10): 581-585 (2008)).

However, it is considered highly likely that also other substitutions (e.g. of amino acid positions 53-55, 57-89, 73-75, 77-80) or the introduction of charged residues in the central domain of alpha-synuclein (residues 30 to 100), which forms the core of the fibrils, may have a negative effect on the fibril formation and/or an increased toxicity.

Accordingly, in a further preferred embodiment, the mutant or homologue of the invention may further comprise at least one of the substitutions E13K, Q24K, E35K, V37P, L38P, Y39C, Y39A, V40P, V40D, K45E, E46K, V48P, V49P, A50P, V52P, A53T, T59P, E61K, V63P, T64P, N65P, V66S, V66P, G67P, G68P, G68T, G68V, A69P, A69T, A69V, A69K, V70G, V70T, V70P, V70F, V71T, V71K, T72P, T72V, T72E, V74D, V74E, V74G, V74T, T75P, T75K, V77T, A78T, T81P, V82K, E83K, E83P, A89P, A90P, V95S, Y125A, Y133A, Y136A. Consequently, this means that the mutant or homologue comprising at least one amino acid substitution selected from the group consisting of a substitution at the alanine at position 56 (A56), at the alanine at position 76 (A76), at the methionine at position 127 (M127) and/or at the valine at position 118 (V118), either further comprising the substitution A30P or not, may further comprise at least one of these substitutions in SEQ ID NO: 1 or at the corresponding amino acid residue(s) of the homologue.

"At least one substitution" means that the mutant alpha-synuclein may comprise one, or two, or three, or four, or five, or six, or seven, or eight, or nine, or ten, or eleven, or twelve, or 13, or 14, or 15, or even more substitutions selected from the group of substitutions given above.

In another preferred embodiment, the mutant or homologue according to the invention may be one, wherein 1 to 40 amino acids of the C-terminal end are deleted. Thus, 1 to 40 amino acids of the residues 100 to 140 of SEQ ID NO: 1 may be deleted, preferably a stretch of 1 to 40 amino acids, including residue 140 of SEQ ID NO: 1. However, the 1 to 40 amino acids to be deleted may also not be in one stretch and may also not contain residue 140 of SEQ ID NO: 1. Preferably up to 1, 2, 3, 4, 5, 6, 7, 8, 9, 10, 11, 12, 13, 14, 15, 20, 21, 25, 30, or 35 amino acids of the C-terminal end are deleted.

In one preferred embodiment, the mutant or homologue of the invention may be one, wherein the fibril formation ability of the mutant alpha-synuclein or homologue is decreased compared to wild-type alpha-synuclein. If the fibril formation ability is decreased compared to the wild-type can be determined using the Thioflavin (ThioT) fluorescence assay. Briefly, 5 μl aliquots (100 μM) from mutant and wild-type alpha-synuclein incubations are withdrawn and added to 2 ml of 5 μM ThioT in 50 mM Glycine-NaOH pH 8.2. Fluorescence measurements are carried out on a spectrofluorometer using 3.5 ml quartz cuvettes with a path length of 1 cm. Fluorescence emission spectra are recorded from 465 to 600 nm, using excitation wavelength of 446 nm, an integration time of 0.1 second, and both excitation and emission bandwidths of 10 nm. Kinetic aggregation traces are generated from time traces of ThioT fluorescence intensity at 482 nm and corrected for free ThioT fluorescence. Aggregation yields are normalized to the final values and the averaged data points are fitted to a sigmoidal equation. A decreased fibril formation ability is evident if the lag time is at least 2fold, 5fold, 10fold, 20fold, 50fold, 60fold, 70fold, 80fold, 90fold, 100fold, more preferably 200fold, 300fold, 400fold, 500fold, 600fold, 800fold, 900fold, 1000fold, 10000fold, 100000fold higher compared to wild-type alpha-synuclein under identical conditions. Most preferably, the mutant alpha-synuclein or homologue has no more fibril formation ability, even though pre-fibrillar alpha-synuclein complexes may be formed.

In a further aspect, the invention relates to a polynucleotide encoding the mutant alpha-synuclein or homologue thereof according to the invention, or an expression vector comprising said polynucleotide.

A polynucleotide can be any nucleic acid sequence capable of encoding a mutant alpha-synuclein or homologue according to the invention, such as single-stranded or double-stranded DNA, the sense or antisense strand of a DNA molecule, or RNA molecules, and the like. The person skilled in the art knows how to derive a polynucleotide sequence coding for a protein and how to isolate or produce such a nucleic acid sequence using standard techniques of molecular biology. Since the polynucleotide encoding the mutant alpha-synuclein or homologue does not encode a naturally occurring polypeptide (e.g., it encodes a mutated and/or truncated alpha-synuclein or a fusion protein) the respective nucleic acid coding for the polypeptide may be produced in accordance with standard procedures including well-known methods of genetic engineering. Further, the polynucleotide sequence may also be adapted to the codon usage of the host intended to be transfected with the polynucleotide.

The polynucleotide of the invention can be included in an expression construct such as a vector, plasmid, virus/phagemid, artificial chromosome, cosmid, and further constructs known to the skilled person in order to provide for expression of the sequence of the mutant or homologue of the invention. Techniques for modifying nucleic acid sequences for insertion into a vector e.g. by utilizing recombinant DNA methods are also well-known in the art. Generally, an expression vector comprises the polynucleotide to be expressed, which is operably linked to one or more control sequences (e.g., promoter, transcriptional stop signal, translational stop signal, etc.) capable of directing the expression of the polypeptide in the desired host cell. The promoter can be an inducible or constitutive, general or cell specific promoter. Preferred examples of cell specific promoters are the dat-1 promoter fragment of the dopamine transporter gene core promoter and the human synapsin-1 gene promoter. The selection of promoters, vectors and other elements is a matter of routine design within the level of ordinary skill in the art and many different such control sequences are described in the literature and available through commercial suppliers. Generally, the choice of the vector will typically depend on the choice of the host cell into which the vector will be introduced. Preferred expression vectors for use in the present invention are the pT7-7, the *C. elegans* expression vector pPD115.62, the GAL4-responsive pUAST expression vector, and the AAV-1/2 mosaic serotype viral vector or derivatives thereof.

In a further aspect, the invention relates to a cell comprising the polynucleotide or expression vector described above.

The polynucleotide or expression vector may be introduced into cells by various ways, e.g., using a virus as a carrier or by transfection including e.g. by chemical transfectants (such as Metafectene, Lipofectamine, Fugene, etc.), electroporation, calcium phosphate co-precipitation and direct diffusion of DNA. Suitable transfection techniques are known to the skilled person and the method of choice will vary depending on the host cell to be transfected. Transfection of a cell may yield stable cells or cell lines, if the transfected polynucleotide or expression vector is integrated into the genome, or by using episomal replicating plasmids, i.e. that the inheritance of the extrachromosomal plasmid is controlled by control elements that are integrated into the cell genome. In addition, unstable (transient) cells or cell lines, wherein the transfected DNA exists in an extrachromosomal form can be produced.

The expression vector may further comprise a selectable marker, which provides for positive selection of transfected cells, i.e. transfected cells exhibit resistance to the selection and are able to grow, whereas non-transfected cells generally die. Examples of selective markers include puromycin, zeocin, neomycin (neo) and hygromycin B, which confer resistance to puromycin, zeocin, aminoglycoside G-418 and hygromycin, respectively. However, other selection methods known to the skilled person may also be suitable.

The cell may be maintained and cultured at an appropriate temperature and gas mixture (typically, 37° C., 5% $CO_2$), optionally in a cell incubator as known to the skilled person. Culture conditions may vary for each cell type, and variation of conditions for a particular cell type can result in different phenotypes. Furthermore, recipes for growth media can vary in pH, glucose concentration, growth factors and the presence of further suitable nutrient components. Growth media are commercially available, or can be prepared according to compositions, which are for example obtainable from the American Tissue Culture Collection (ATCC). Growth factors used for supplement media are often derived from animal blood such as calf serum, but also other probably cell specific growth factors may be enclosed. Additionally, antibiotics may be added to the growth media to prevent undesired microbial growth. More specifically, cell culturing is further exemplified in the Examples section.

In general, the cell may be any kind of cell. For the expression and purification of the mutant or homologue of the invention, a prokaryotic cell may be used, such as the *E. coli* strain BL21. However, for other purposes, including the methods described herein, a eukaryotic cell or cell line may be used. Cell lines which may be used in the invention are commercially available from culture collection such as the ATCC or from other commercial suppliers.

In general, the cell may exogenously express the mutant alpha-synuclein, i.e. the polynucleotide or expression vector encoding the mutant alpha-synuclein or homologue has been introduced into the cell. Thus, the mutant-alpha-synuclein or homologue according to the invention may be derived from the same species or a different one than the cell. Optionally, a cell may endogenously express alpha-synuclein according to SEQ ID NO: 1, or a homologue thereof as defined above, i.e. the alpha-synuclein homologue is naturally expressed in the cell. In that case the cell may be obtained by genetic engineering of the endogenous gene expressing wild-type alpha-synuclein.

In a preferred embodiment, the cell is a yeast cell or an invertebrate cell, preferably a cell of *C. elegans* or *D. melanogaster*, or wherein the cell is a vertebrate cell, preferably a mammalian cell, more preferably a mouse, a rat, or a primate cell, in particular a non-human embryonic stem cell. It is noted that those cells or cell lines, particularly human embryonic stem or germline cells, are excluded, which are not subject to patentability under the respective patent law or jurisdiction.

Dopaminergic neuronal cells are neurons whose primary neurotransmitter is dopamine, which has many functions in the brain, including important roles in behavior and cognition, motor activity, motivation and reward, inhibition of prolactin production (involved in lactation), sleep, mood, attention, and learning. Dopaminergic neuronal cells are mainly present in the ventral tegmental area of the midbrain, substantia nigra pars compacta, and arcuate nucleus of the hypothalamus. As indicated above, symptoms of Parkinson's disease result from the loss of dopaminergic cells in the region of the substantia nigra pars compacta. Their loss leads to alterations in the activity of the neural circuits within the basal ganglia that regulate movement. In general, it is considered that symptoms appear when 80% of these neurons are lost leading to a hypokinetic movement disorder. Accordingly, in another preferred embodiment, the cell according to the invention is a dopaminergic neuronal cell.

In a further aspect, the invention provides a non-human animal comprising the cell according to the invention, wherein the non-human animal is an invertebrate, preferably *C. elegans*, or *D. melanogaster*, or wherein the non-human animal is a vertebrate, preferably a mammal, more preferably a mouse, a rat, or a primate.

Also, a non-human animal comprising the cell according to the invention, wherein the non-human animal is an invertebrate, preferably *C. elegans*, or *D. melanogaster*, or wherein the non-human animal is a mammal is contemplated. More specifically, the invention contemplates a non-human animal comprising a dopaminergic neuronal cell according to the invention.

In general, the non-human animal may be any animal other than a human. However, some model organisms, which may preferably be used in the invention, have gained particular attention in research. Among invertebrates, these are *Caenorhabditis elegans, Arbacia punctulata, Ciona intestinalis, Drosophila*, usually the species *Drosophila melanogaster, Euprymna scolopes, Hydra, Loligo pealei, Pristionchus pacificus, Strongylocentrotus purpuratus, Symsagittifera roscoffensis*, and *Tribolium castaneum*. Among vertebrates, these are several rodent species such as guinea pig (*Cavia porcellus*), hamster, mouse (*Mus musculus*), and rat (*Rattus norvegicus*), as well as other species such as chicken (*Gallus gallus domesticus*), cat (*Felis cattus*), dog (*Canis lupus familiaris*), Lamprey, Japanese ricefish (*Oryzias latipes*), Rhesus macaque, *Sigmodon hispidus*, zebra finch (*Taeniopygia guttata*), pufferfish (*Takifugu rubripres*), african clawed frog (*Xenopus laevis*), and zebrafish (*Danio rerio*). Among vertebrates, mammals are particularly preferred. Also preferred are non-human primates, i.e. all species of animals under the order Primates that are not a member of the genus Homo, for example rhesus macaque, chimpanzee, baboon, marmoset, and green monkey. However, these examples are not intended to limit the scope of the invention. It is noted that those animals are excluded, which are not likely to yield in substantial medical benefit to man or animal and which are therefore not subject to patentability under the respective patent law or jurisdiction. Moreover, the skilled person will take appropriate measures, as e.g. laid down in international guidelines of animal welfare, to ensure that the substantial medical benefit to man or animal will outweigh any animal suffering.

Such a non-human animal may serve as a model system for synucleinopathies (sometimes also named alpha-synucleinopathies), such as dementia with Lewy bodies (DLB), Parkinson disease, Parkinson's disease with dementia (PDD), multiple system atrophy and the Lewy body variant of Alzheimer's disease. Thus, synucleinopathies describe a group of diseases which have all a common involvement of alpha-synuclein.

In a further aspect, the invention provides a method for identifying a substance that prevents or reduces toxicity of alpha-synuclein to a test cell, the method comprising:
  (a) culturing the cell according to the invention;
  (b) contacting the cell with a test substance; and
  (c) comparing the cell viability of the cell subjected to step (b) with the cell viability of a corresponding cell subjected to step (a), but not step (b);
  wherein an increase in the cell viability of the cell subjected to step (b) compared to the cell viability of a corresponding cell subjected to step (a), but not step (b), is indicative of the capability of the substance to prevent or reduce toxicity of alpha-synuclein.

The test substance may be provided in the form of a chemical compound library including a plurality of chemical compounds which have been assembled from any of multiple sources, such as chemically synthesized molecules and natural products, or have been generated by combinatorial chemistry techniques. They may have a common particular structure or may be compounds of a particular creature such as an animal. In the context with the present invention the test substance may comprise small molecules, proteins or peptides.

The cell viability may be determined as described above using the water-soluble tetrazolium salt (WST) colorimetric assay for determining mitochondrial dehydrogenase activity according to the protocol of the manufacturer. There are other assays known in the art, which are also commercially available as kits for determining the cell viability, such as kits comprising a fluorescence-dye labelled anti Annexin V antibody (abcam, BD, BIOMOL). Specifically late apoptotic cells may be detected by adding ethidium bromide to a sample of the cells following flow cytometric analysis. Furthermore, cell proliferation, which is another marker of cell viability, may be determined by an XTT assay (Roche). The person skilled in the art will know which assay to choose depending on the cell which is applied in the method of the invention.

In the context of the present invention, the cell viability of the cell subjected to step (a), but not step (b) of less than 90%, less than 80%, less than 70%, in particular less than 65%, less than 60%, less than 55%, less than 50%, less than 45%, less than 40%, less than 35%, less than 30%, less than 25%, less than 20%, less than 15%, less than 10%, or less than 5% in comparison to the cell which has been subjected to step (a) and (b) is indicative for an increase in the cell viability.

Further, the invention provides a method for identifying a substance that prevents or reduces toxicity of alpha-synucleinto a test animal, the method comprising:
  (a) providing a non-human animal according to the invention;
  (b) administering a test substance to the non-human animal; and
  (c) comparing the result of a suitable test selected from the group consisting of tests for the locomotion, sleeping behavior, circadian rhythm, behavior, lifespan, retinal degeneration and/or the neuronal degeneration for the non-human animal subjected to step (b) with the result of the same test for a corresponding non-human animal subjected to step (a), but not step (b);
  wherein a difference in the result of said test for the non-human animal subjected to step (b) in comparison to the result of said test for the corresponding non-human animal subjected to step (a), but not step (b), is indicative of the capability of the substance to prevent or reduce toxicity of alpha-synuclein.

The skilled person will know which test is suitable, depending on the choice of the non-human animal.

It is well-known in the art that synucleinopathies affect the locomotion. Thus, one suitable test to identify whether a substance is capable to prevent or reduce toxicity of alpha-synuclein is a test for the locomotion. The tests will vary depending on the choice of the non-human animal. For example, if the non-human animal was a fly, such as *Drosophila melanogaster*, one suitable well-known test would be the climbing assay. In this assay the flies to be tested are placed in an apparatus in a black case, containing a bottom vial and an inverted upper vial, wherein they are assayed for their ability to reach the upper vial from the bottom vial in twenty seconds. Since flies generally get attracted towards light, a light source is provided at the top of upper vial with the help of two light emitting diodes. This type of set up provides a directionality and motivation for the flies to climb up. Other tests for the locomotion of an animal are known in the art.

If the non-human animal(s) subjected to step (b) has/have an improved locomotion compared to the non-human animal(s) subjected to step (a), but not step (b), this is indicative for the capability of the substance to prevent or reduce toxicity of alpha-synuclein. In the context of the above example of a test for locomotion, a higher percentage of the flies subjected to step (b) which exhibit the ability to reach the upper vial in twenty seconds compared to the flies which have been subjected to step (a), but not step (b), under the same conditions is indicative for an improved locomotion.

Other symptoms of synucleinopathies, such as Parkinson's disease, are sleep disturbances, characterized by excessive daytime somnolescence, initial, intermediate, and terminal insomnia, and disturbances in REM sleep. Somnolescence describes a state of near-sleep, a strong desire for sleep, or sleeping for unusually long periods. It has two distinct meanings, referring both to the usual state preceding falling asleep, and the chronic condition referring to being in that state independent of a circadian rhythm. Thus, tests for circadian rhythm are closely related to tests for sleeping behaviour and may be tested in the same way. Insomnia is a symptom of a sleeping disorder characterized by persistent difficulty falling asleep or staying asleep despite the opportunity and is typically followed by functional impairment while awake.

Thus, one suitable test to identify whether a substance is capable to prevent or reduce toxicity of alpha-synuclein is a test for the sleeping behavior or circadian rhythm. Again, tests will vary and the skilled person will know which test to apply, depending on the choice of the non-human animal. For example, if the non-human animal was a fly, such as *Drosophila melanogaster*, one suitable test would be a sleep assay. Briefly, fly embryos are collected in 2 hour window periods, and are grown under LD 12:12 at 25° C. before the eclosion. Males are collected from the progeny and aged with equal population density under LD 12:12 at 25° C. After 25-30 days, locomotor activity of the aged flies is recorded in LD by the *Drosophila* Activity Monitoring (DAM) system (Trikinetics, Waltham, Mass.) as described in (Hendricks et al. *Nat Neurosci* 4, 1108-15 (2001)). Sleep is measured as bouts of 5 min of inactivity, using a moving window of 1 min intervals. Average bout length (ABL) is calculated from the sum of sleep bouts of all lengths (in minutes) divided by the total number of sleep bouts. Furthermore, an activity index can be calculated by dividing total daily activity by the total wake time of the flies subjected to step (b) and the flies subjected to step (a), but not step (b).

If the non-human animal(s) subjected to step (b) has/have decreased sleep disturbances compared to the non-human animal(s) subjected to step (a) but not step (b), this is indicative for the capability of the substance to prevent or reduce toxicity of alpha-synuclein. In the context of the above example of a test for sleeping behavior, a longer sleep or a decreased activity index of the flies subjected to step (b) compared to the flies which have been subjected to step (a) but not step (b), under the same conditions is indicative for decreased sleep disturbances.

Other suitable tests to identify whether a substance is capable to prevent or reduce toxicity of alpha-synuclein are tests commonly referred to as tests for behavior. Examples for tests for behavior encompass tests for cognition (e.g., voluntary and involuntary motor responses), tests for memory (e.g., short-term memory, procedural memory), and social tests. However, many other tests for behavior are known in the art as well. Also, tests will vary and the skilled person will know which test to apply, depending on the choice of the non-human animal. For example, if the non-human animal was a nematode, such as *C. elegans*, one suitable test would be an assay for the response to the presence of food. Typically, healthy animals will slow down their movement in order to feed more efficiently as a dopamine-controlled behavior. Therefore, this behavior allows to directly assess the functional integrity of dopaminergic neurons in *C. elegans*. For behavioral analysis wellfed adult animals are transferred to the center of an assay plate with or without food as described previously (Brenner, S. *Genetics* 77, 71-94 (1974)). After an initial time of adjustment for 5 min the movement was assayed by counting body bends over a one min interval with three repetitions per animal. The slowing rate was calculated and defined as the percentage of locomotion on food as compared to the locomotion on plates without food.

If the non-human animal(s) subjected to step (b) show(s) a more similar behavior compared to healthy animals in comparison to the non-human animal(s) subjected to step (a) but not step (b), this is indicative for the capability of the substance to prevent or reduce toxicity of alpha-synuclein. In the context of the above example of a test for behavior, a higher percentage of worms that slow down locomotion of the worms subjected to step (b) compared to the worms which have been subjected to step (a) but not step (b), under the same conditions is indicative for a more similar behavior compared to healthy animals.

Tests for lifespan are well known to the skilled person and comprise all kind of techniques for determining the lifetime of an animal starting from birth or hatching (optionally also eclosion) and ending with the death of the non-human animal.

Tests for determining retinal degeneration are well known in the art, and the skilled person will know how to choose a suitable test.

Finally, the invention provides a method for identifying a substance that prevents or reduces toxicity of alpha-synuclein to a test animal, the method comprising:
(a) providing a non-human animal according to the invention and subjecting said non-human animal to a suitable test selected from the group consisting of tests for the locomotion, sleeping behavior, circadian rhythm, behavior, retinal degeneration and/or the neuronal degeneration;
(b) administering a test substance to the non-human animal and subjecting the animal to the same test; and
(c) comparing the result obtained in step (b) with the result obtained in step (a);
wherein a difference in the result of said test for step (a) in comparison to step (b) is indicative.

A, Functional domains of alpha-S. Familial mutants (E46K, A53T, A56P) and design mutants (A30P, A76P) are labeled along the sequence. Regions involved in beta-sheet formation in the fibril are marked (purple). B, Superimposed contour plots of the $^1H$—$^{15}N$ HSQC spectra of wt (black) and TP (red) alpha-S in the free state at 15° C. Affected resonances are labeled. Mutated residues are shown in red. C, Circular dichroism spectra of A56P alpha-S (yellow), TP alpha-S (red) and wt alpha-S (black) in solution (top panel) and in the presence of sodium dodecyl sulfate micelles (bottom panel). Mutations do not strongly change the overall secondary structure of alpha-S in the two states. D, Diffusion properties of A56P alpha-S (circles), TP alpha-S (long dashes) and wt alpha-S (black short dashes) as observed by NMR signal decays in pulsed field gradient measurements at 15° C. 1,4-dioxane (dark blue) was used as internal standard. The fact that the diffusion properties are not substantially different in wt and mutant alpha-S indicate that the overall shape averaged over the ensemble of conformations is not changed by the mutations.

Figure 2:
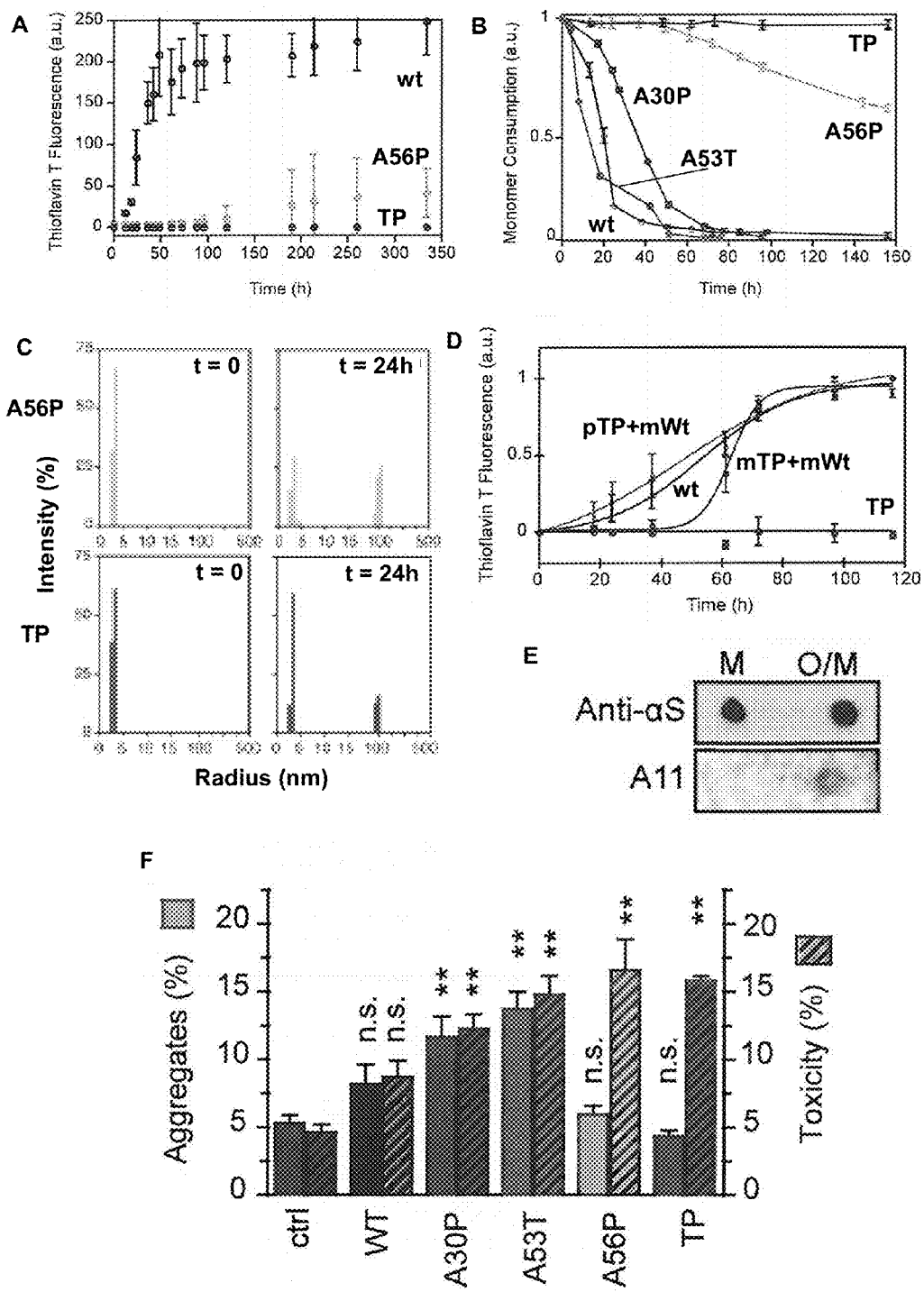
Figure 2:
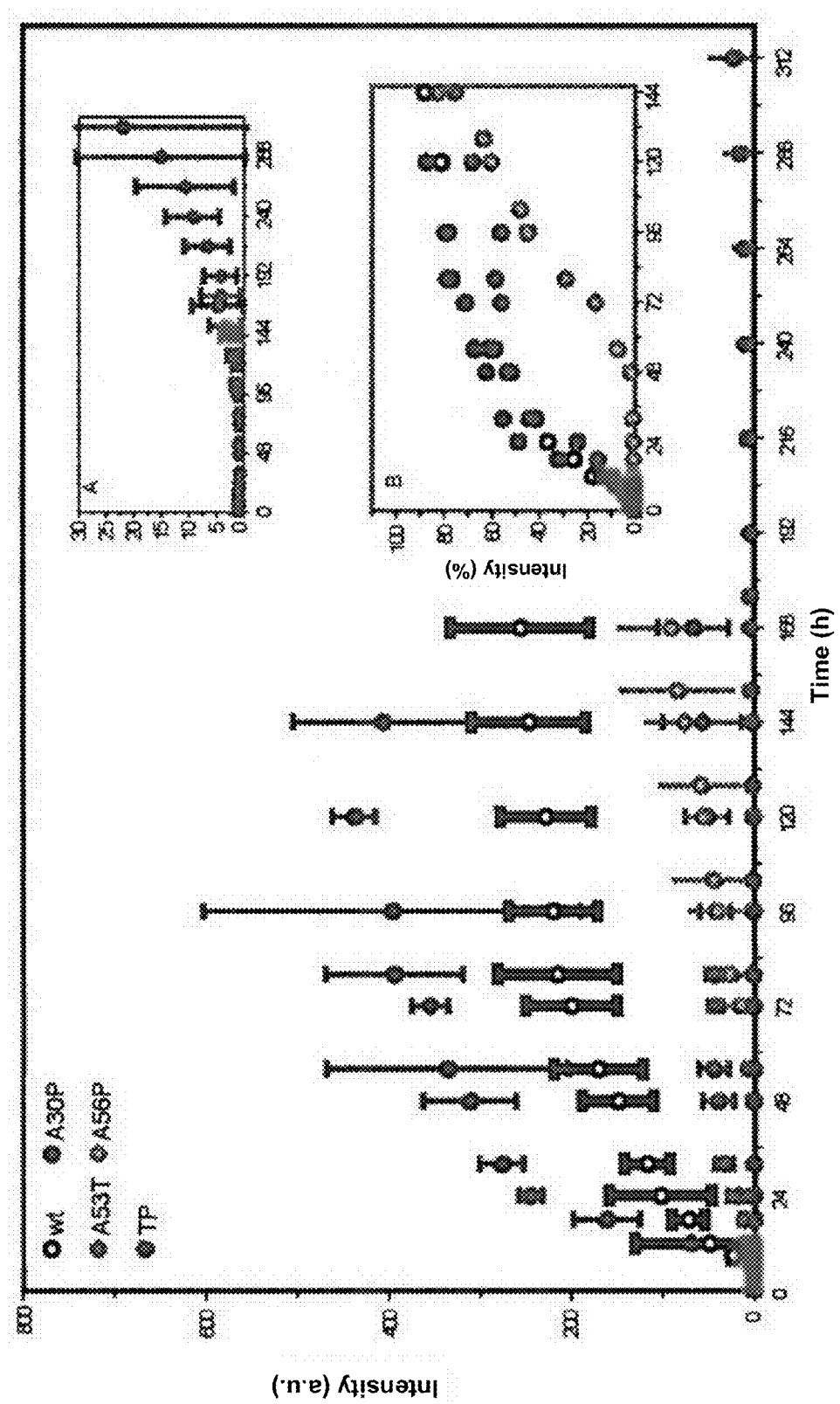

FIG. 2. Point mutations delay formation of amyloid fibrils of alpha-S.

A, Fibril formation of wt alpha-S (black), A56P alpha-S (yellow) and TP alpha-S (red) followed by Thioflavin T fluorescence. B, Consumption of monomeric wt alpha-S (black), A53T (cyan) A30P alpha-S (purple), A56P alpha-S (yellow) and TP alpha-S (red) monitored by 1D $^1$H NMR spectroscopy. Drop in signal intensity is due to formation of higher molecular weight aggregates not detectable by solution-state NMR. Errors were estimated from three independent aggregation assays. C, Dynamic light scattering of A56P alpha-S (yellow) and TP alpha-S (red). Data presented here are a representative of 30 acquisitions. D, Pre-fibrillar aggregates of TP alpha-S seed fibril formation of wt alpha-S. In an equimolar mixture of pre-aggregated TP alpha-S with monomeric wt alpha-S the lag time of aggregation is decreased (light blue) when compared to wt monomer alone (black), whereas in an equimolar mixture of monomeric TP alpha-S and monomeric wt protein the lag time is increased (dark blue). Aggregation behaviour of TP alpha-S alone is shown in red. Error bars in A, B and D represent mean±standard deviation of three independent experiments. E, Recognition of a mixture of oligomers and monomers of TP alpha-S (O/M) but not monomeric TP alpha-S (M) on nitrocellulose membrane by the A11 antibody. Anti-alpha-S antibody shows comparable attachment to both monomer and oligomer. F, Aggregate formation and toxicity in HEK293T cells: alpha-S aggregation was visualized by adding the six amino acids of a PDZ binding domain to the C-terminus and coexpressing the corresponding PDZ domain fused to EGFP (ctrl, PDZ-EGFP alone). Cells with more than one aggregate ("aggregation", left axis, clear bars) and preapoptotic cells ("toxicity", right axis, hached bars) were counted 24 h after transfection. Bars represent percentages of all EGFP-positive cells (mean±SEM, n=5 independent experiments). Significances are depicted with respect to ctrl (n.s., not significant; **, p<0.01, One-way ANOVA and Dunnet's posthoc test). G Fibril formation of wt alpha-S (black), A30P (purple), A53T (blue), A56P alpha-S (yellow) and TP alpha-S (red, also shown in Inset A at a different scale) followed by Thioflavin T (ThT) fluorescence emission intensity. Inset B demonstrates ThT intensity values of all but TP variants, each of them normalized by the maximal value observed along their aggregation reaction.

Figure 3:
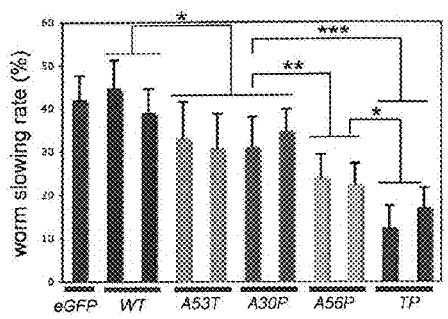
Figure 3:
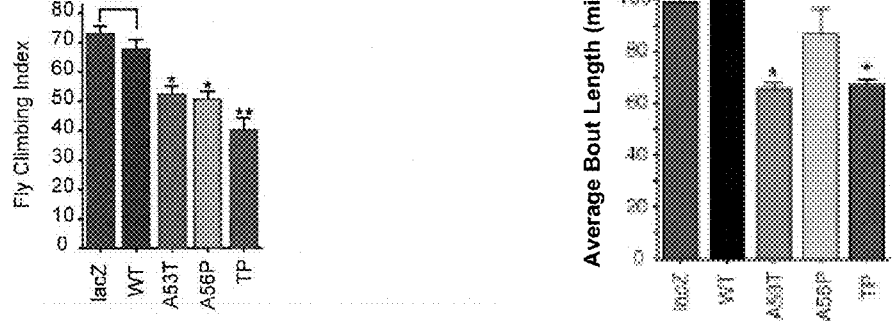
Figure 3:
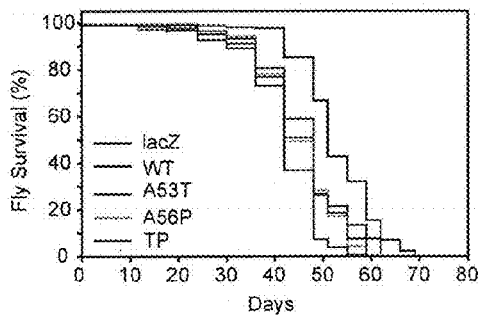
Figure 3:
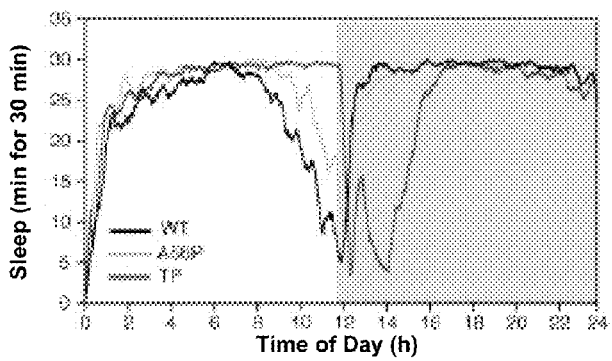

FIG. 3. Structure-based design mutants of alpha-S cause movement disorders, sleep impairment and reduced life span of C. elegans and Drosophila.

A, 'Basal slowing response' of C. elegans expressing different alpha-S variants in dopaminergic neurons. For each alpha-S variant expressed at least two independent transgenic lines were tested (n=40-50 animals per trail, 3 trails). The slowing rate corresponds to the average decrease in movement (body bends/min) for animals placed in food as compared to animals without food. Animals expressing only EGFP in dopaminergic neurons are shown as control. The error bar correspond to the standard error of the mean (SEM) and the significance values of the ANOVA test are indicated: *p<0.05; p<0.01; *p<0.001. B, Climbing assay on flies with corresponding genotypes. Climbing index, percentage of 25-30 day old flies that could reach the top chamber in a fixed amount of time (n=35-50 for each group). C, Survival curves of flies expressing different variants of alpha-S and LacZ. A56P alpha-S and TP alpha-S curves are significantly different from wt alpha-S (Logrank Test: P<0.0217 for wt alpha-S versus A56P alpha-S, and P<0.0001 for wt alpha-S and TP alpha-S. n=350-400 for each genotype). D) Averaged sleep profiles of wt alpha-S (black), A56P alpha-S (yellow) and TP alpha-S (red) (shading represents lights off). E) Changes in the average length of sleep bouts (n=40-50 for each genotype). Where errors are shown, they are s.e.m. Significance was determined by one-way analysis of variance followed by Dunnett's Multiple Comparison test. *P<0.05; **P<0.01; n.s. non significant in comparison with wt alpha-S, P>0.05.

Figure 4:
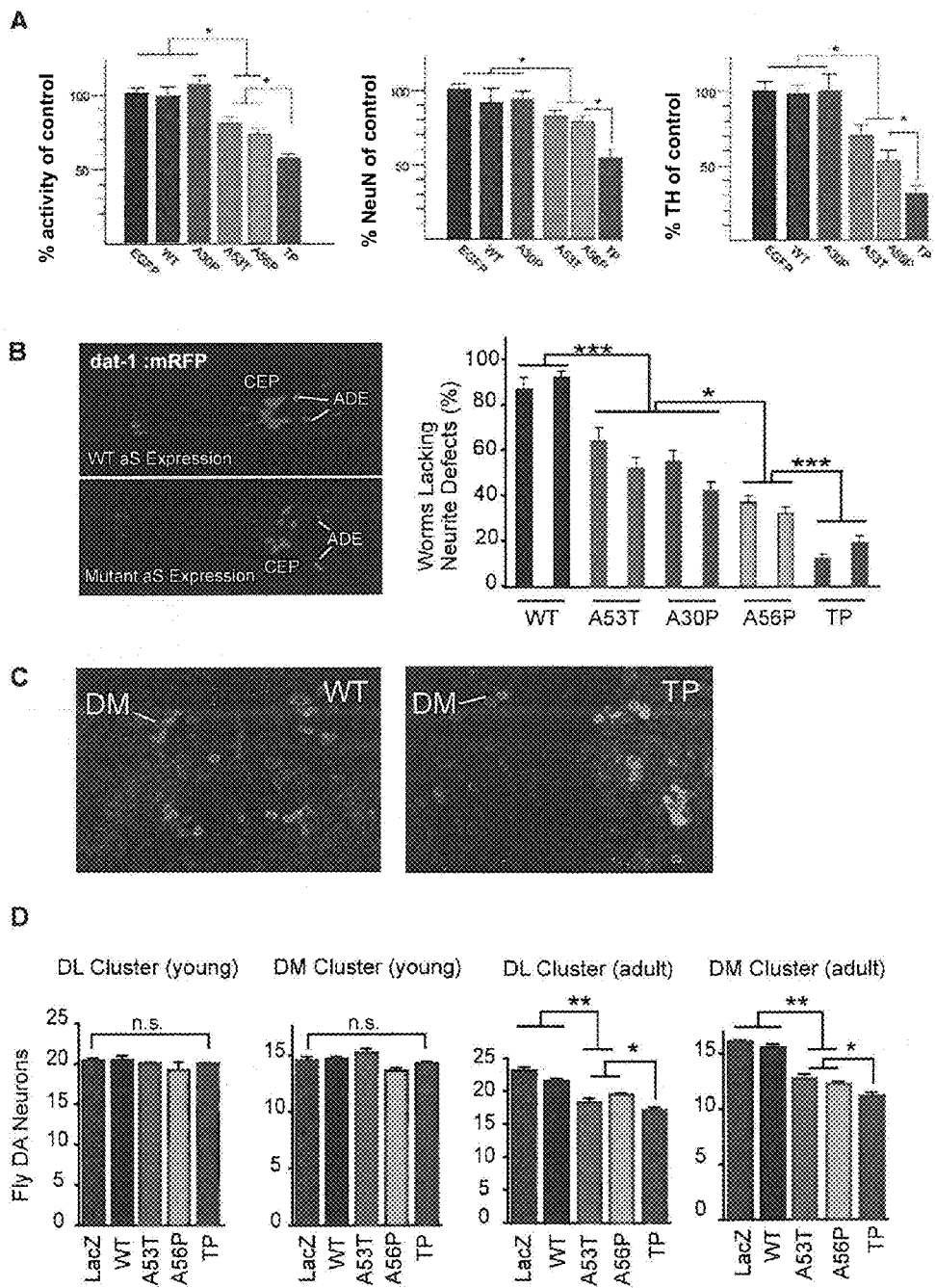

FIG. 4. Neurotoxicity of structure-based design mutants of aS in mammalian neurons, C. elegans and Drosophila.

Figure 23:
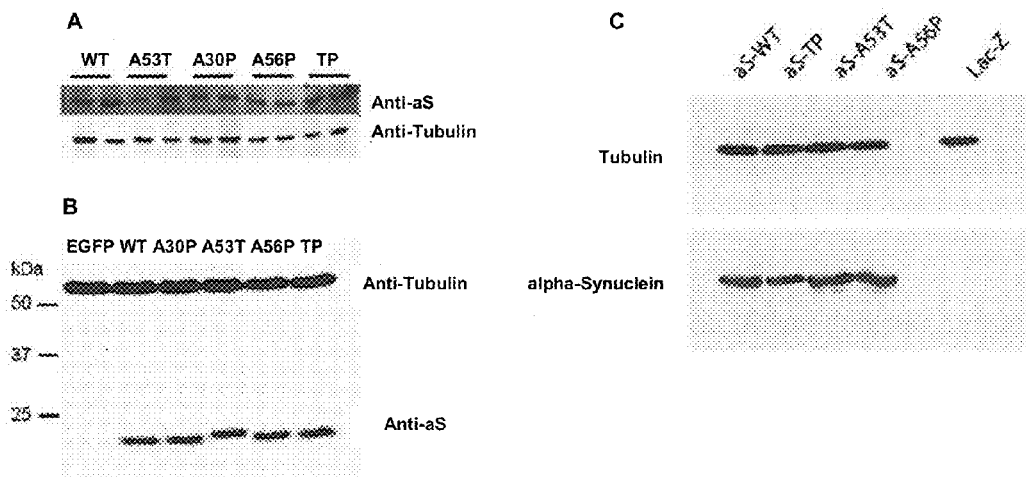

(A) Structure-based design variants in rat primary neurons. Left panel: WST assay of cortical neurons transduced by AAV-EGFP, AAV-alpha-S-wt, AAV-alpha-S-A30P, AAV-alpha-S-A53T, AAV-alpha-S-A56P and AAV-alpha-S-TP, respectively. Mitochondrial dehydrogenase activity measured after transduction with respective alpha-S mutants is shown as percentage of activity measured after AAV-EGFP transduction (n=30). Middle panel: Neuronal cell loss quantified by NeuN immunocytochemistry. Numbers of NeuN immunoreactive cells counted after transduction with respective alpha-S mutants is shown as percentage of numbers counted after AAV-EGFP transduction (n=15). Right panel: Degeneration of dopaminergic midbrain neurons quantified by TH immunocytochemistry. Numbers of TH immunoreactive cells counted after transduction with respective alpha-S mutants is shown as percentage of numbers counted after AAV-EGFP transduction (n=12). Data are shown as mean+/−SEM. In all cases significance was determined by one-way ANOVA analysis of variance followed by Dunnett's posthoc test *P<0.05; **P<0.01. (B) C. elegans expressing red fluorescent protein mCherry and wt alpha-S (upper left panel) or TP alpha-S (lower left panel) in the cephalic (CEP) and anterior deirid (ADE) dopaminergic neurons in the head. Right panel: degeneration of dendritic processes induced by expression of αS in dopaminergic neurons. Two independent transgenic lines are shown per alpha-S variant and 78-80 animals we analyzed per line. (C) Whole-mount immunostaining of fly brains. Images are maximum projections of several confocal sections in the z-plane. (D) Quantitative analysis of dopaminergic neuron numbers in the dorsomedial (DM) and dorsolateral (DL) cluster in brains of 2 day (young) and 29 day (adult) old flies. Values represent mean+/−SEM. Asterisks indicate that the difference in dopaminergic neuron numbers was statistically significant. For 2 day old flies, no statistically significant difference was observed in numbers of dopaminergic neurons. Expression levels of different alpha-S variants were comparable (FIG. 23).

Figure 5:
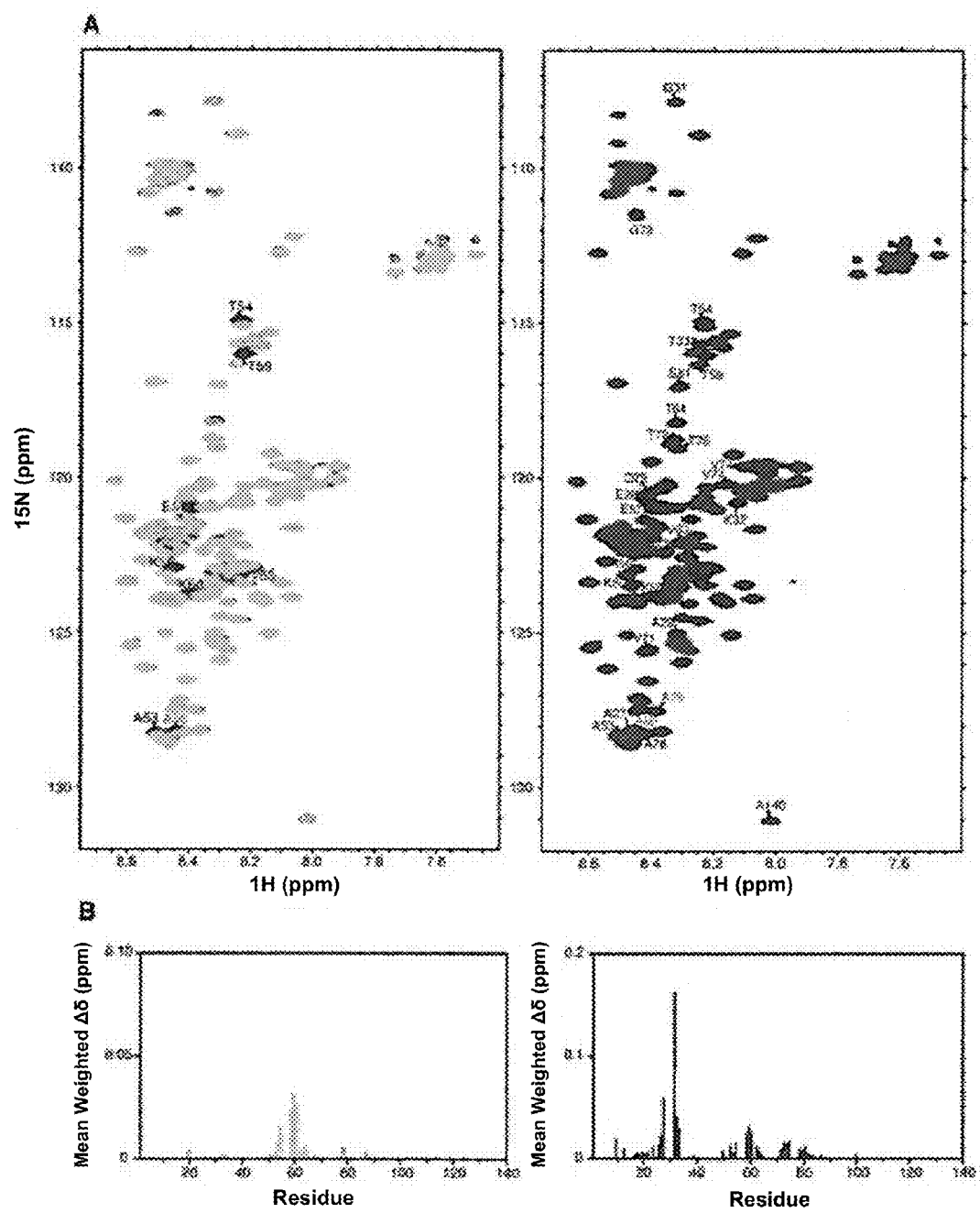

FIG. 5. Monomeric forms of design variants of aS remain disordered in solution.

(A) Superimposed contour plots of the $^7$H—$^{15}$N HSQC spectra of monomeric wt (black), A56P (yellow) and TP (red) alpha-S in solution at 15° C. Influenced resonances are labeled. Mutated residues are marked (red). (B) Mean weighted $^7$H—$^{15}$N chemical shift differences between wt and A56P aS (yellow) and between wt and TP aS (red) in the free State (calculated from $[(A5\ ^7H)^2+(A5^{15}N)^2/25]^{1/2})/2])$.

Figure 6:
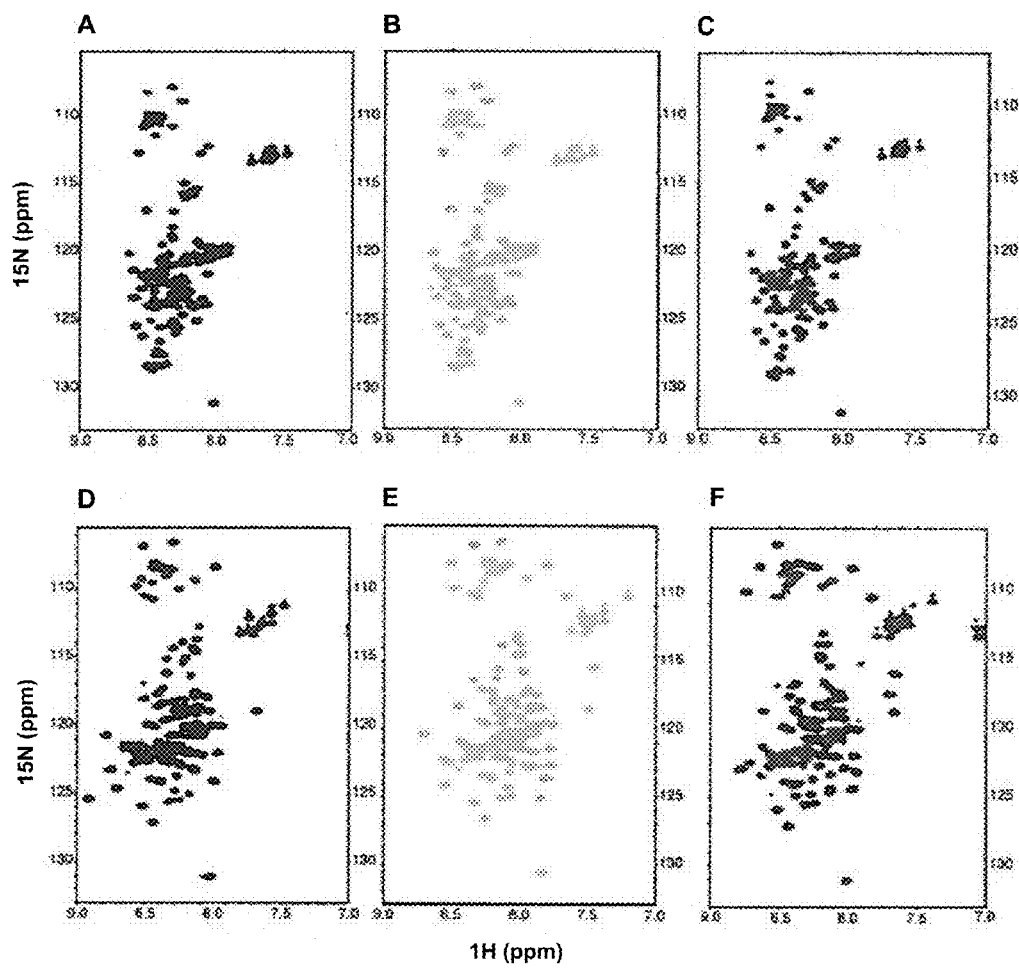

FIG. 6. Design mutations do not prohibit the interaction of alpha-S with negatively charged SDS micelles.

$^1H-^{15}N$ HSQC spectra of free wt (A), A56P (B) and TP (C) alpha-S. $^1H-^{15}N$ HSQC spectra of wt (D), A56P (E) and TP (F) alpha-S in the presence of SDS micelles at 40° C. and pH 7.4. An increase in resonance dispersion with respect to free spectra is observed upon addition of the micelles for all three variants.

Figure 7:
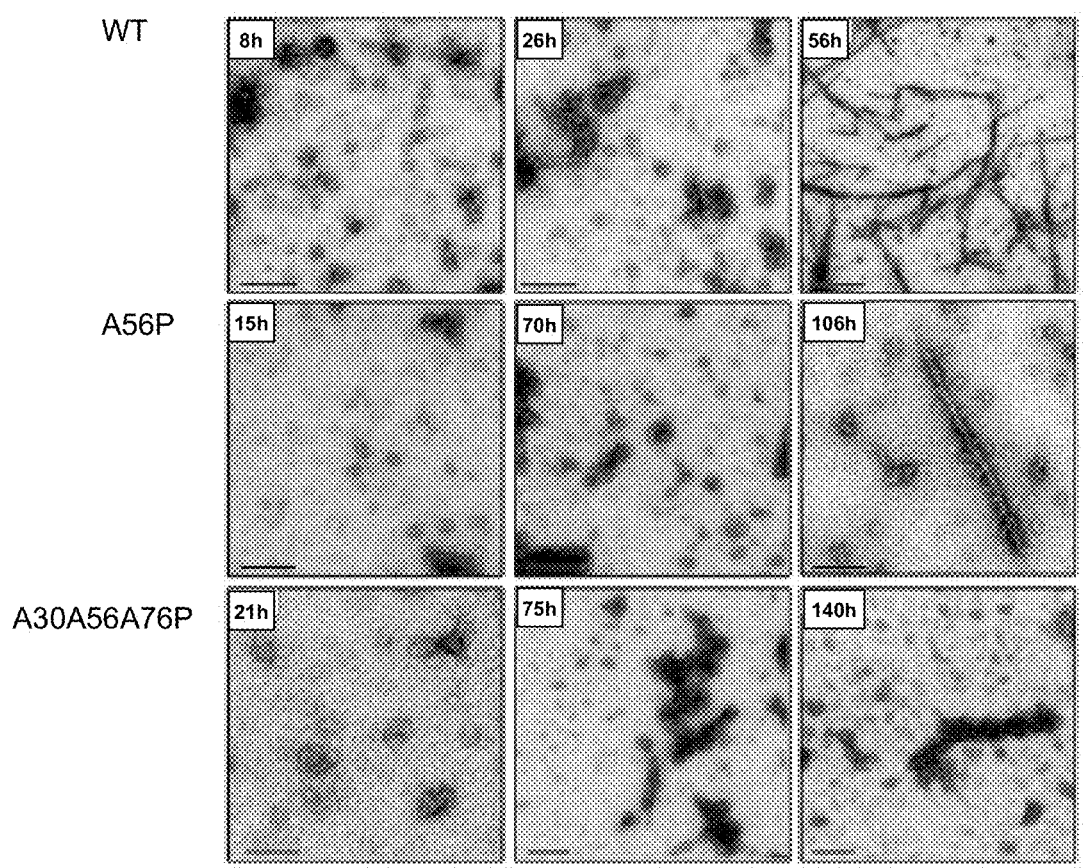

FIG. 7. Electron microscopy analysis of the aggregation of wt, A56P and TP alpha-S.

Electron micrographs shown are representative pictures for triplicates. Scale bars correspond to 200 nm, except wt alpha-S 56h and TP alpha-S 21h, where they correspond to 500 nm and 100 nm, respectively. Oligomers were observed in all three samples early on in the aggregation process. Mature fibrils were observed after about 50 h for wt alpha-S, after about 100 h for A56P alpha-S and no traces of mature fibrils were detected for TP alpha-S in a period of two weeks. Total protein concentration in each sample was 100 μM.

Figure 8:
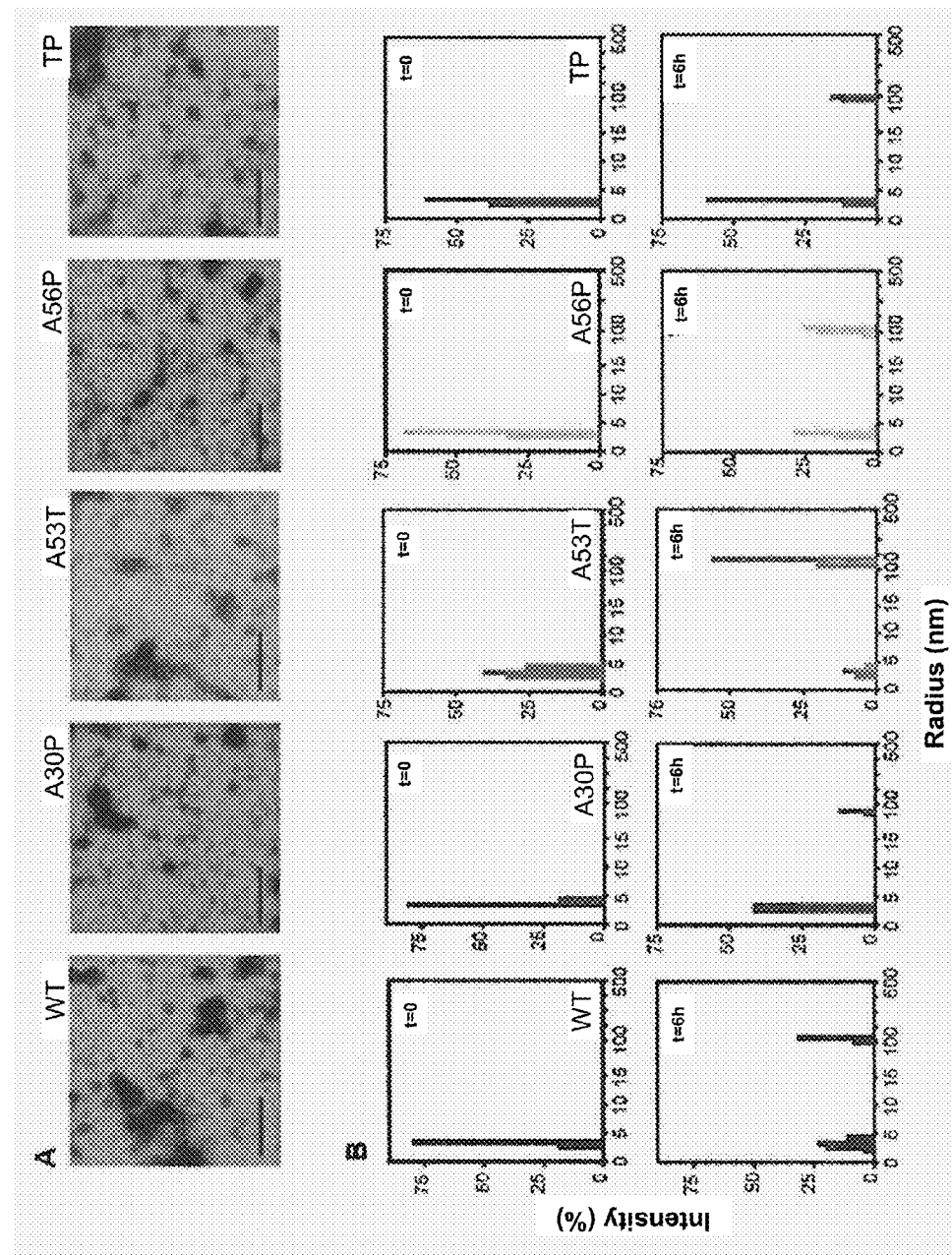

FIG. 8. Morphology of soluble oligomers formed by alpha-S variants.

(A) Electron micrographs of soluble oligomers formed by alpha-S variants. The protein concentration was 100 μM and samples were aggregated for 12 h at 37° C. and 200 rpm. Scale bars correspond to 200 nm. (B) Dynamic light scattering of alpha-S variants. Data presented here are a representative of 30 acquisitions of 10 s.

Figure 9:
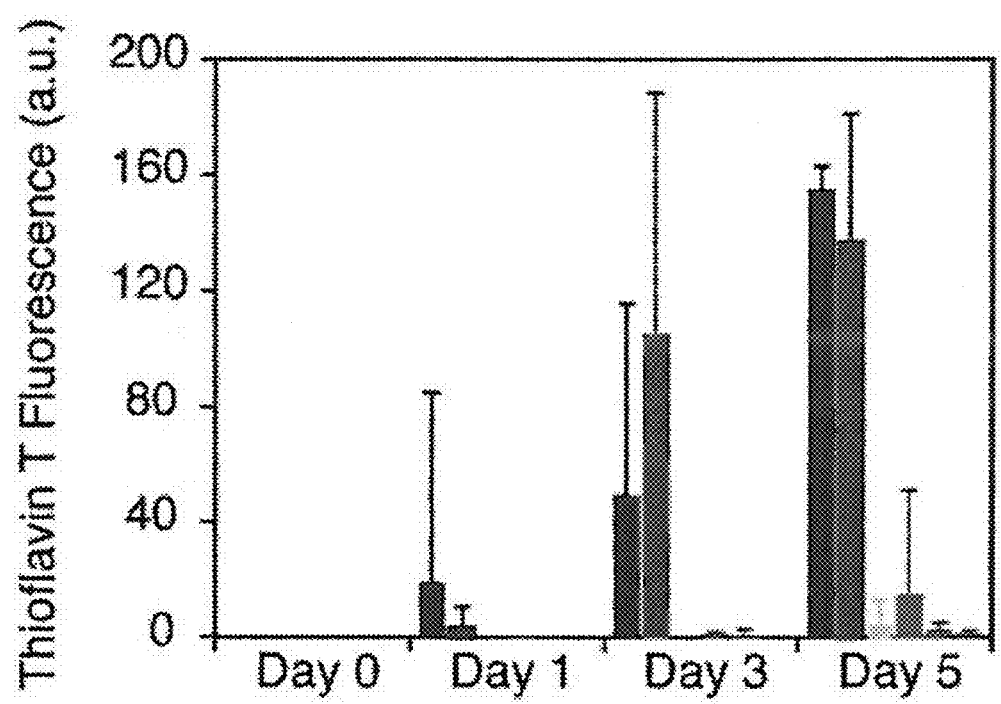

FIG. 9. Thioflavin T measurements of the alpha-S variants.

From left to right: Wt (black), A30P (purple), A56P (yellow), A76P (green), A30PA56P (blue), A30PA76P (magenta).

Figure 10:
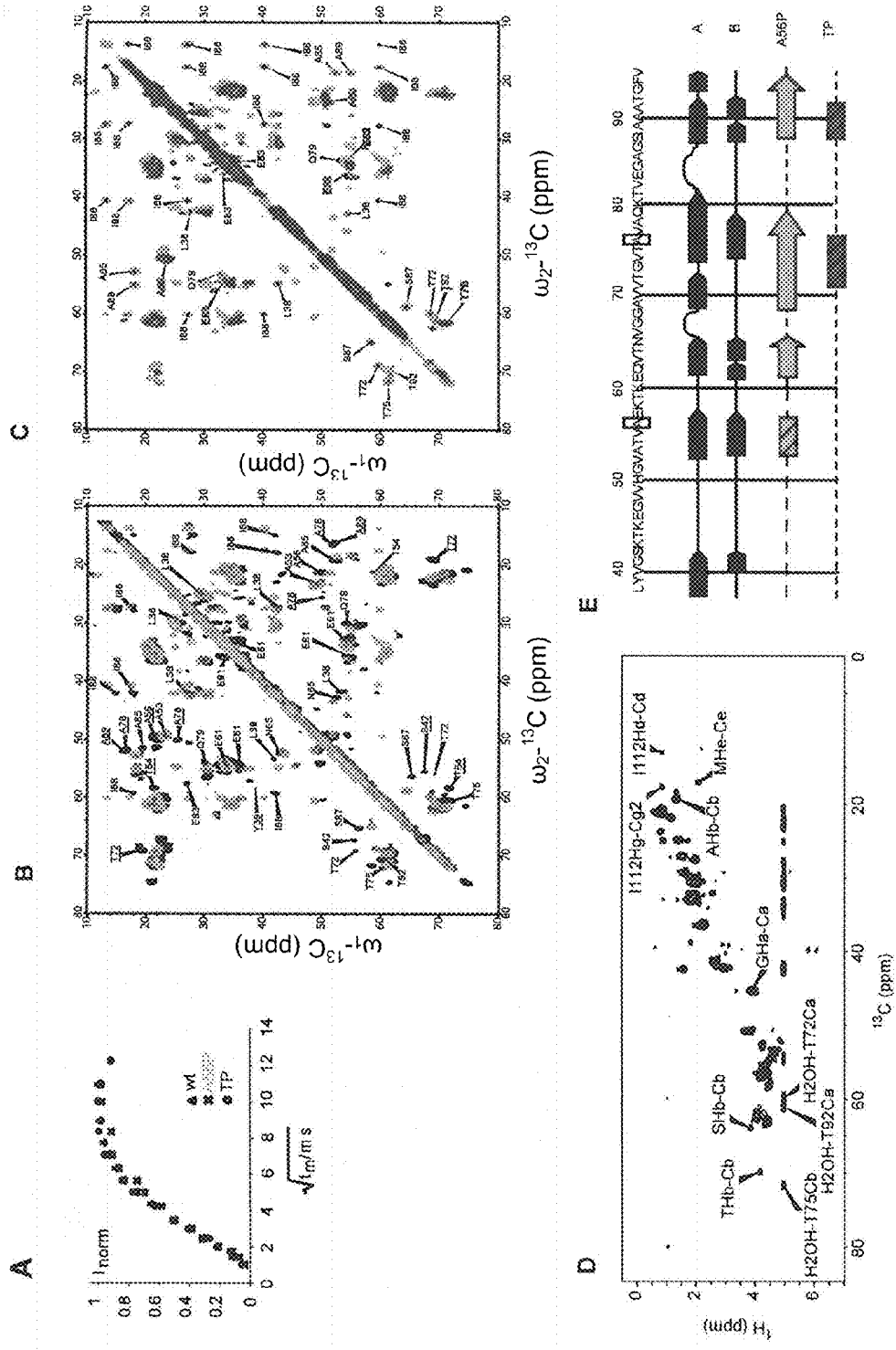

FIG. 10. High Resolution solid-state NMR of late stage aggregates formed by alpha-S variants.

(A) Water accessibility of aggregates as probed by solid-state NMR. A 3 ms Gaussian pulse and a $T_2$ filter containing two delays of 1 ms were used for selective water excitation. The cross polarization contact time was set to 700 μs. (B) Superposition of 2D $^{13}C/^{13}C$ correlation spectra of U-[$^{13}C$, $^{15}N$] A56P alpha-S (yellow) and of wt alpha-S (black). Correlations absent in the A56P mutant are underlined. Assignments correspond to values obtained for the A form of wt alpha-S as reported in (Heise et al., 2005). (C) Superposition of 2D $^{13}C/^{13}C$ correlation spectra of U-[$^{13}C,^{15}N$] A56P alpha-S (yellow) and of U-[$^{13}C,^{15}N$] TP alpha-S (red). In (B) and (C), homonuclear mixing was achieved using a proton driven spin diffusion time of 20 ms (A56P) and 50 ms (TP), respectively. (D) 2D $^1H/^{13}C$ $^1H$-$T_2$-filtered HETCOR spectrum of A56P alpha-S. The spectrum was recorded at a magnetic field strength of 14 T, with a spinning speed of 8.33 kHz, at a sample temperature of 0° C. The $T_2$ filter delay was 2×175 μs, the contact time was 3 ms. The spectrum was recorded without homonuclear decoupling during $t_1$, 160 $t_1$ increments and 128 scans per slice. (E) ssNMR-based secondary structure analysis for wt and mutant alpha-S. Row 1 and 2 correspond to wt data reported previously (Heise et al., 2005). Hashed rectangles relate to protein regions in which beta-strands are lost compared to wt alpha-S or, in the case of TP, exhibit strong dynamics/disorder. Arrows relate to beta-strands that are preserved in A56P. Mutation sites are indicated by rectangular boxes, suggesting that A⇌P mutation leads to partial (A56P) or almost complete (TP) suppression of beta-strand formation in alpha-S.

Figure 11:
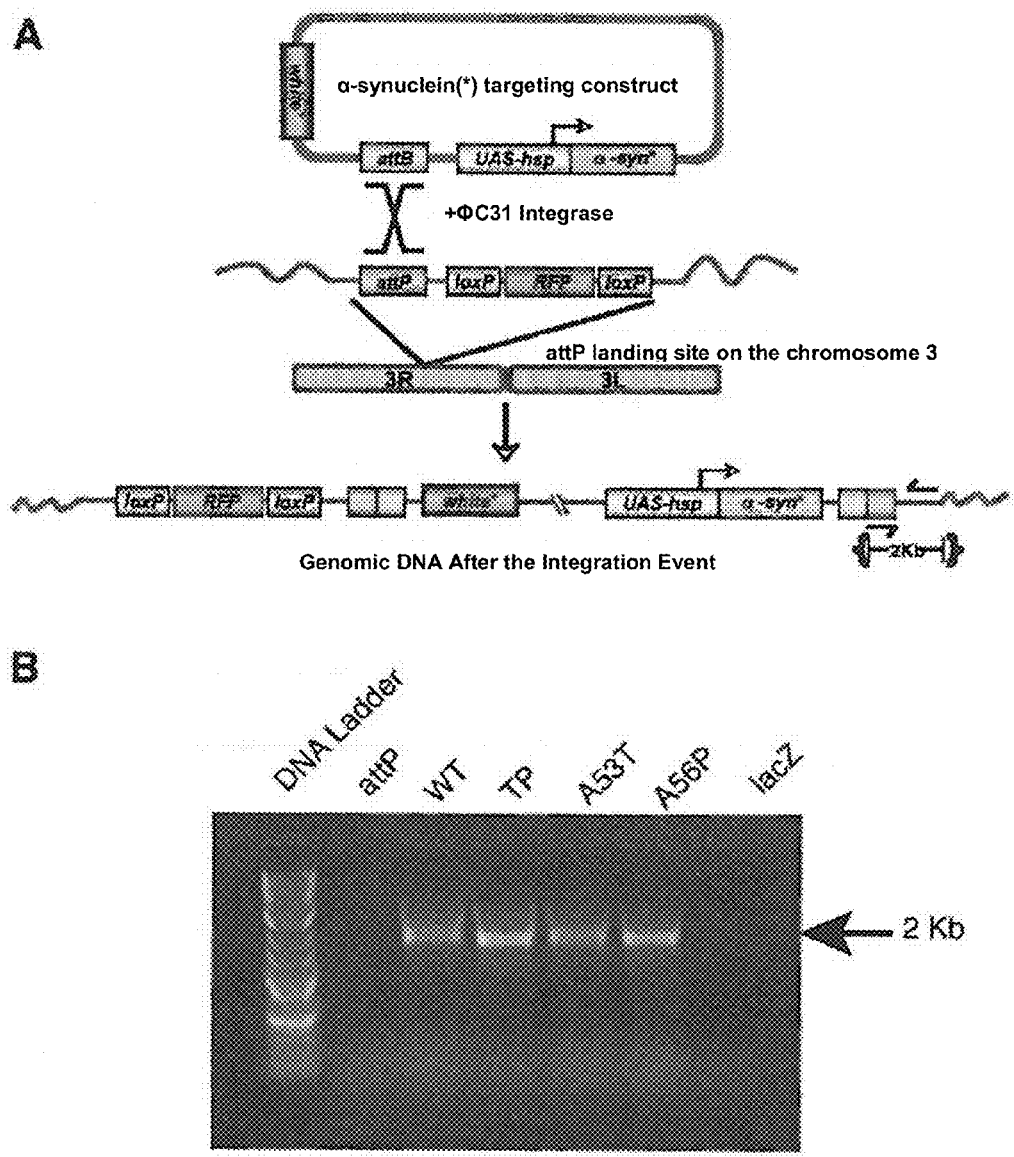

FIG. 11. Targeting alpha-S variants to an identical genomic location ensures comparable expression levels in transgenics.

A, Schematic representation of the *Drosophila* transgenesis based on φ-C31 mediated recombination. B, In all transgenic animals expressing alpha-S mutants (lanes 3, 4, 5, 6), single fly PCR using a alpha-S forward primer and a genomic reverse primer (depicted in a—genomic DNA after the integration event) shows that integration has indeed occurred at the desired attP landing site in the 3R-86Fb genomic region. As controls, flies carrying an empty-attP landing site at 3R-86Fb (lane 2) and flies carrying lacZ insertion at the same location (lane 7) were used.

Figure 12:
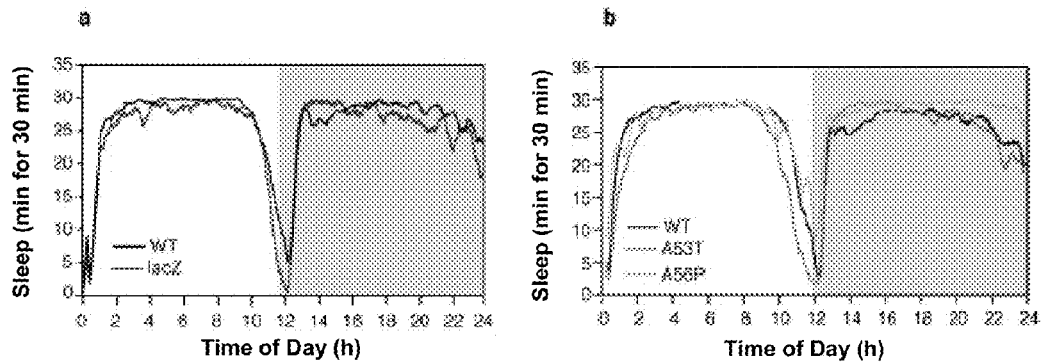

FIG. 12. Sleep profile of 25-30 day old flies.

expressing a, wt alpha-S (black) and lacZ control flies (blue) b, wt alpha-S (black), A53T alpha-S (cyan) and A56P alpha-S (yellow) under the ddc-GAL4 driver.

Figure 13:
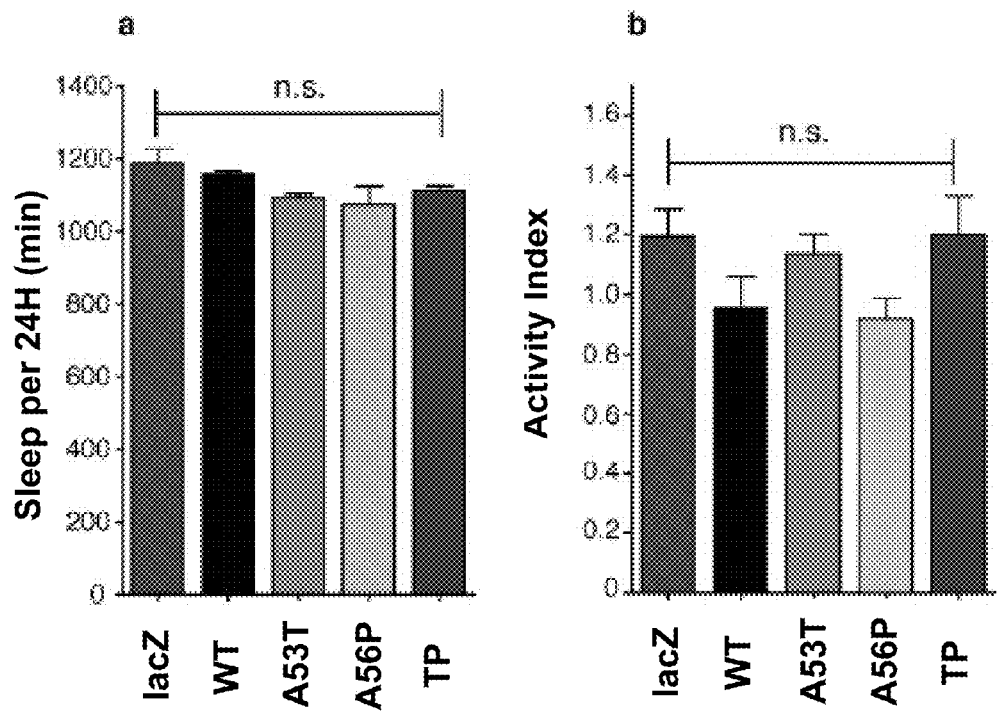

FIG. 13. Total sleep and total activity of flies expressing alpha-S variants.

a, Total sleep per day in flies expressing wt alpha-S (black), TP alpha-S (red), A56P alpha-S (yellow), A53T alpha-S (green) and lacZ control (blue). Differences in total sleep between flies expressing alpha-S mutants are not significant according to one-way ANOVA analysis (P>0.05). b, Activity index of alpha-S variants. The 'Activity Index' was calculated by dividing total daily activity (number of beam crossings per day) by the total wake time for each genotype. According to one-way ANOVA analysis (P>0.05) followed by the Tukey's multiple comparison test differences are not significant; n=30-40 per genotype.

Figure 14:
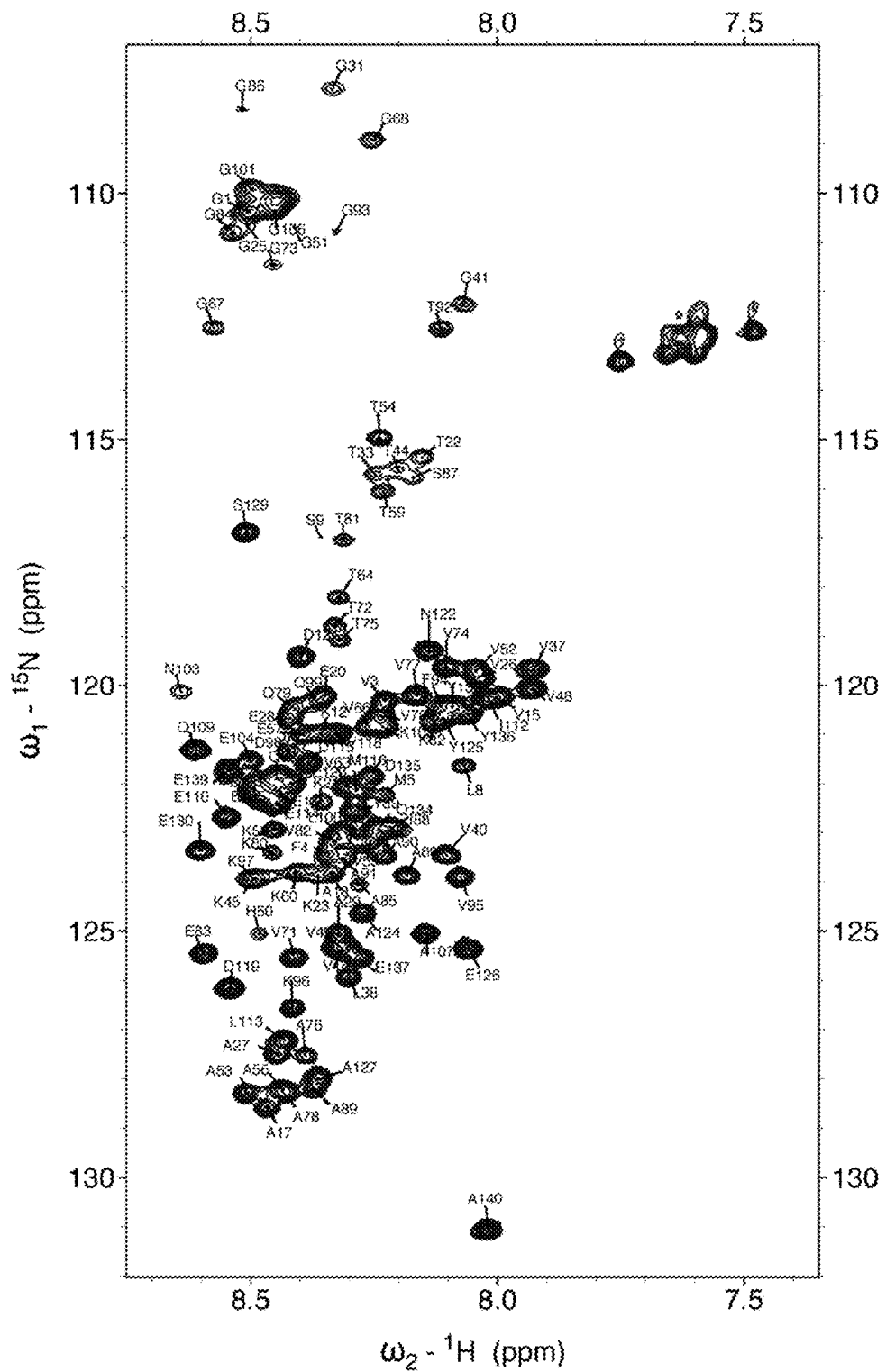

FIG. 14. alpha-Synuclein mutated in the C-terminus remains disordered.

$^1H-^{15}N$ HSQC nuclear magnetic resonance spectrum of M127A alpha-synuclein in solution. Resonance assignments are indicated.

Figure 15:
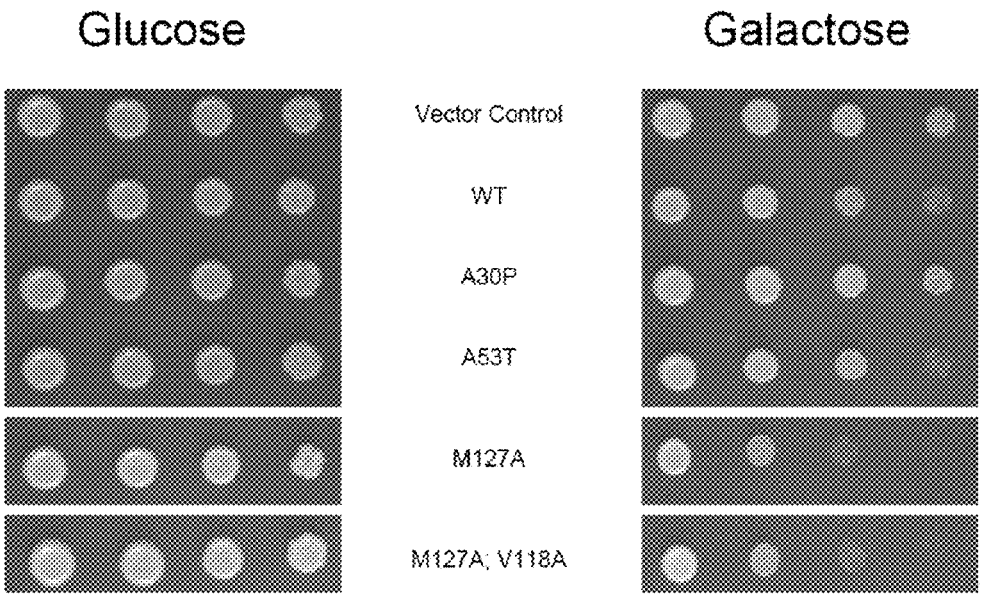

FIG. 15. Toxicity assay using C-terminal mutants of alpha-synuclein in yeast.

Yeast cells were inoculated to an OD600 of 0.1 and incubated under alpha-synuclein inducing conditions (SC-ura/Galactose). Toxicity of the various alpha-synuclein mutants can be judged by the growth impairment compared to vector control.

Figure 16:
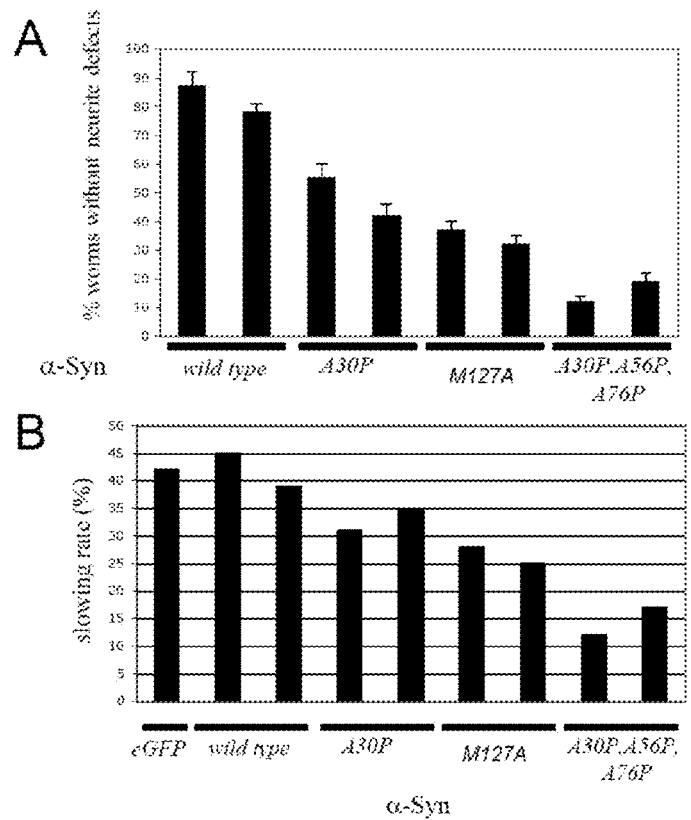

FIG. 16. Movement disorder and neurotoxicity induced by design mutants of alpha-synuclein in *C. elegans*.

A, 'Basal slowing response' of *C. elegans* expressing different alpha-synuclein variants in dopaminergic neurons. For each alpha-synuclein variant expressed at least two independent transgenic lines were tested (n=40-50 animals per trail). The slowing rate corresponds to the average decrease in movement (body bends/min) for animals placed in food as compared to animals without food. Animals expressing only EGFP in dopaminergic neurons are shown as control.

B, Degeneration of dendritic processes induced by expression of alpha-synuclein in dopaminergic neurons. Two independent transgenic lines are show per alpha-synuclein variant and 78-80 animals were analyzed per line.

Figure 17:
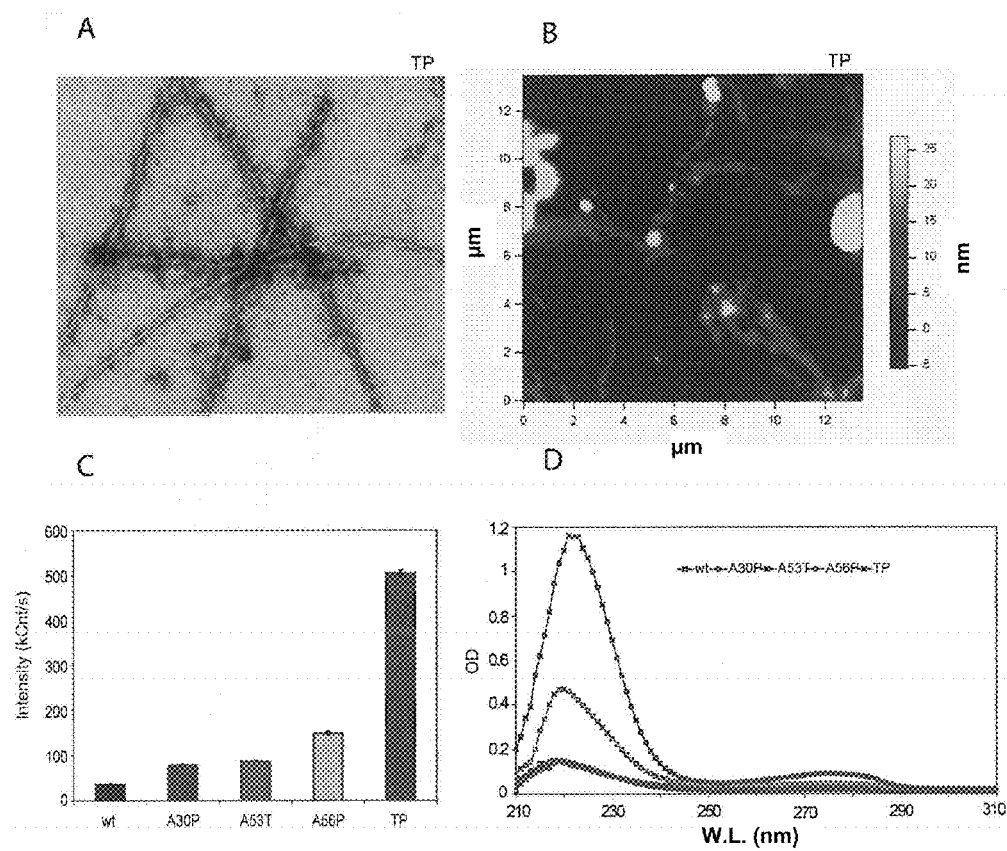

FIG. 17. Enhanced formation of soluble oligomers by αS variants.

(A) Electron micrograph of TP alpha-S solution in 50 mM HEPES, 100 mM NaCl, pH 7.4, 0.01% NaN3, incubated for 6 days at 37° C. while stirred at 200 rpm. The protein concentration was 0.8 mM, and the sample was diluted 8-fold by buffer before EM imaging. Scale bar corresponds to 500 nm. (B) AFM image of TP alpha-S solution. Conditions identical to A). (C) Dynamic light scattering of alpha-S variants, incubated for 11 days at the aggregation condition and then centrifuged briefly and the supernatant was measured. Data presented are average of three measurements, each consisting of 20 acquisitions of 20 s. (D). UV absorbance of the supernatant of aggregated alpha-S variants after 11 days of incubation at the aggregation condition.

Figure 18:
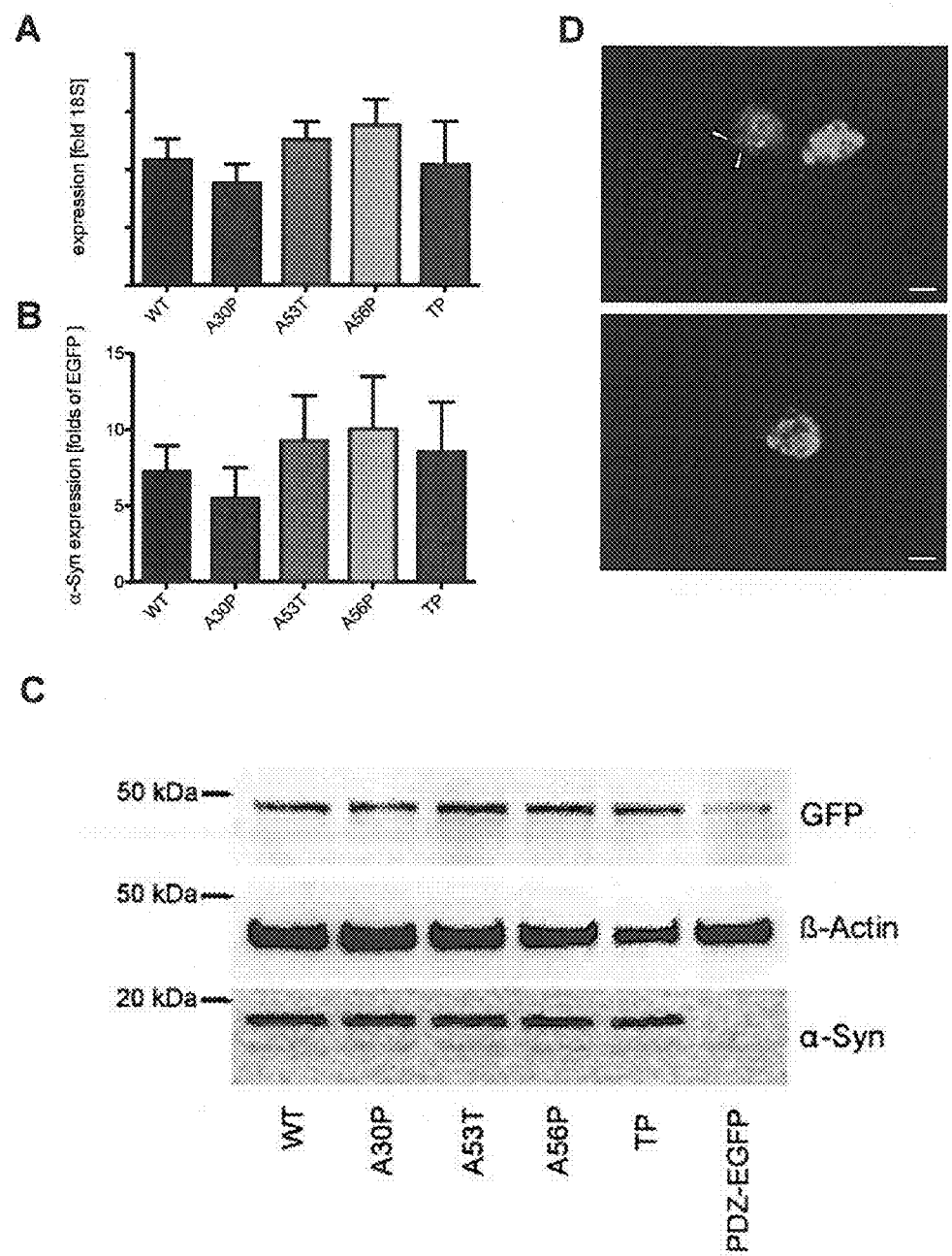

FIG. 18. Aggregate formation and toxicity in HEK293T cells.

(A) Real time PCR quantification of alpha-S mRNA extracted 24 h after transfection. Bars represent alpha-S mRNA relative to the ribosomal 18S subunit mRNA. (mean±SEM, n=3 independent experiments, no significant different between different alpha-S variants) (B) Quantification of the western-blot bands (exemplified in E) no significant different between the different alpha-S variants (mean±SEM, n=3 independent experiments). (C) Western-blot of transfected (24 h) HEK293T cells. Alpha-S including the PDZ binding domain has a molecular weight close to 19 kDa, PDZ domain fused to EGFP has a predicted molecular weight of 46 kDa and beta-actin is close to 42 kDa. (D) Representative images of aggregates (top panel, arrowheads) and preapoptotic cell (lower panel). Scale bar is 10 μm.

Figure 19:
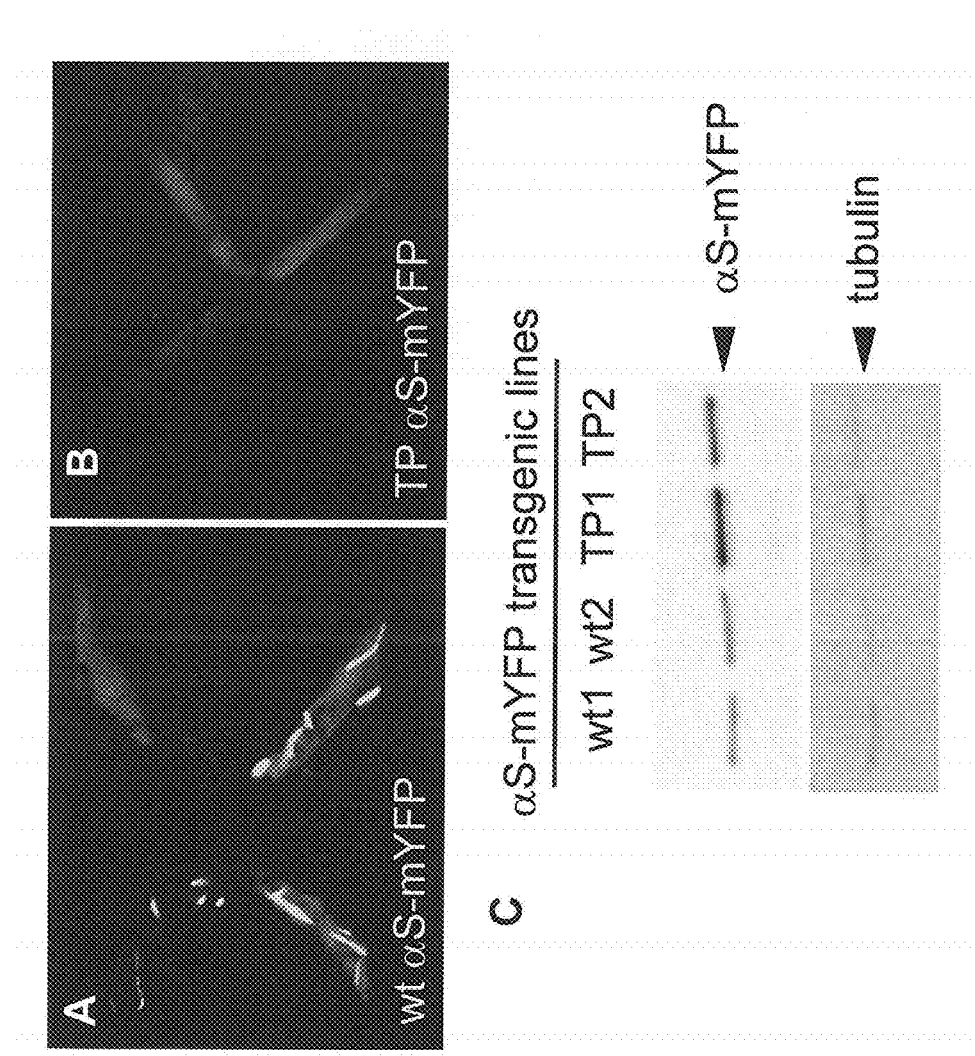

FIG. 19. TP alpha-S displays reduced aggregation propensity in vivo.

Ten-day old vulva muscles are show from transgenic animals expressing either wt alpha-S A) or TP alpha-S B) fused to mYFP. Only wt alpha-S-mYFP leads to extensive fibrilar aggregates while TP alpha-S-mYFP remains diffusely distributed in the cytoplasm. (C) The expression levels of the alpha-S-mYFP fusion proteins are similar as shown by Western blot using anti alpha-S antibodies. Tubulin staining serves as a loading control.

Figure 20:
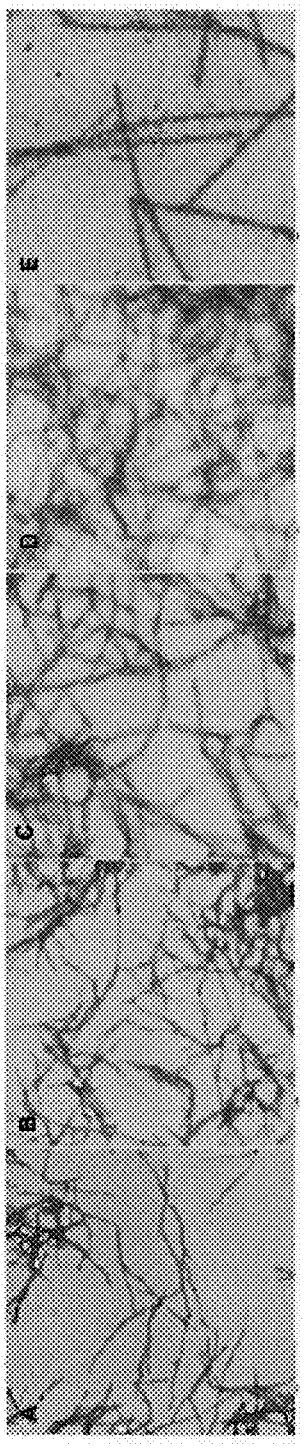

FIG. 20. Electron micrographs of alpha-S variants.

Electron micrographs of alpha-S variants (A: wt, B: A30P, C: A53T, D: A56P, E: TP) after 5 days of incubation at 37° C., 50 mM HEPES, 100 mM NaCl, pH 7.4 and 0.01% $NaN_3$, stirred at 200 rpm. The protein concentration was 0.8 mM. Scale bars correspond to 1000 nm for wt, A30P and A53T and 500 nm for A56P and TP alpha-S.

Figure 21:
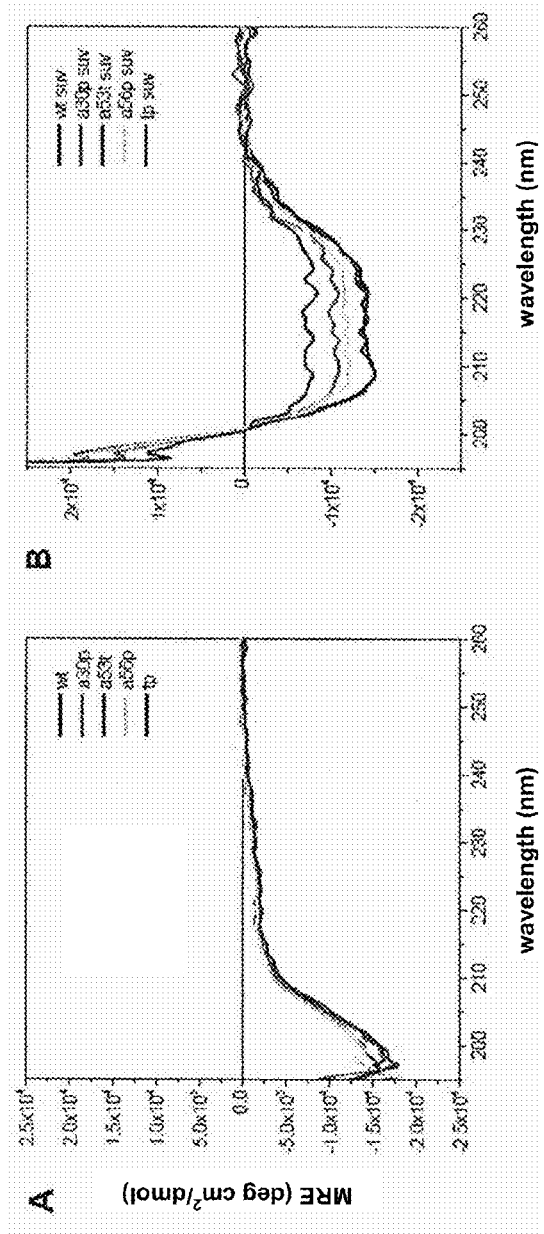

FIG. 21. Circular dichroism spectra of alpha-S variants in the free state (A) and when bound to SUVs formed by POPC: POPA (ratio 1:1) (B).

Figure 22:
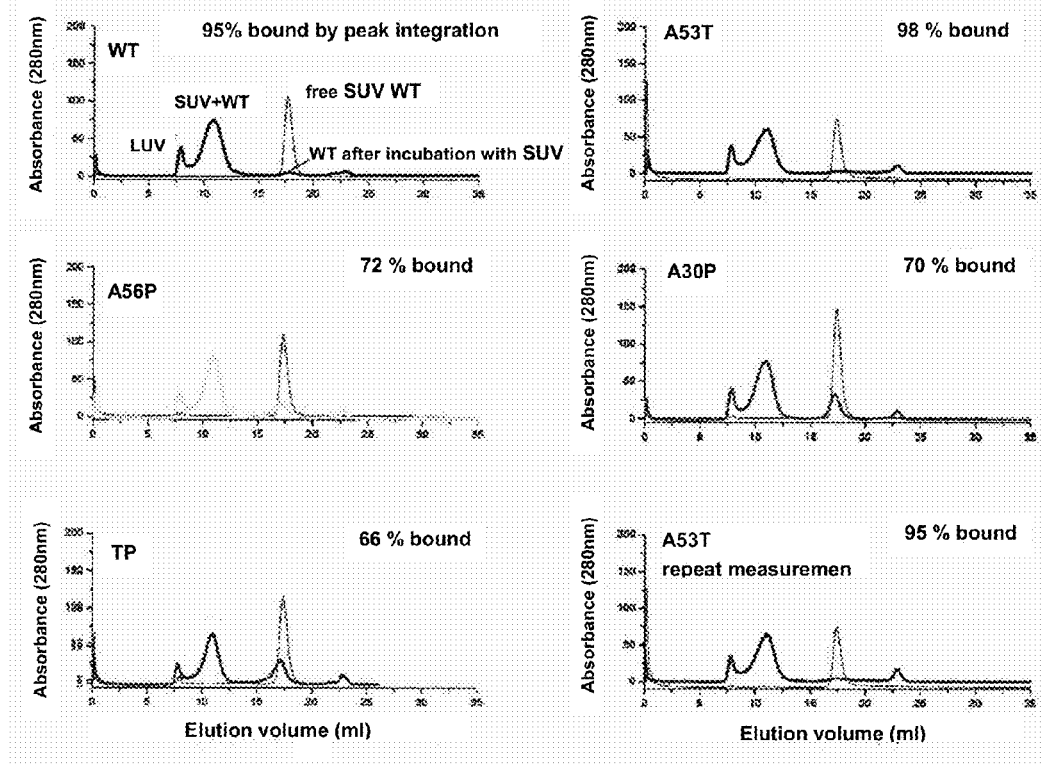

FIG. 22. Binding of αS variants to phospholipid vesicles.

Vesicles prepared from a 1:1 mixture of POPC and POPA were incubated for 5 hours at room temperature with alpha-S variants at a mass ratio of 250:1, and the mixture was separated by gel filtration chromatography on a Superose 6 10/300 GL column (GE healthcare). For comparison, lipid-free alpha-S variants (thin black line) were subjected to similar separation.

FIG. 23. Expression levels of different alpha-S variants are comparable in (A) *C. elegans*, (B) rat neuronal cultures and (C) fruit flies. In (B), A53T alpha-S runs at a slightly higher molecular weight due to the presence of the seven amino acid (DTYRYI) long epitope tag AU1.

EXAMPLES

In the following, the present invention is illustrated by figures and examples which are not intended to limit the scope of the present invention.

Example 1

Design of Alpha-S Variants

Figure 1:
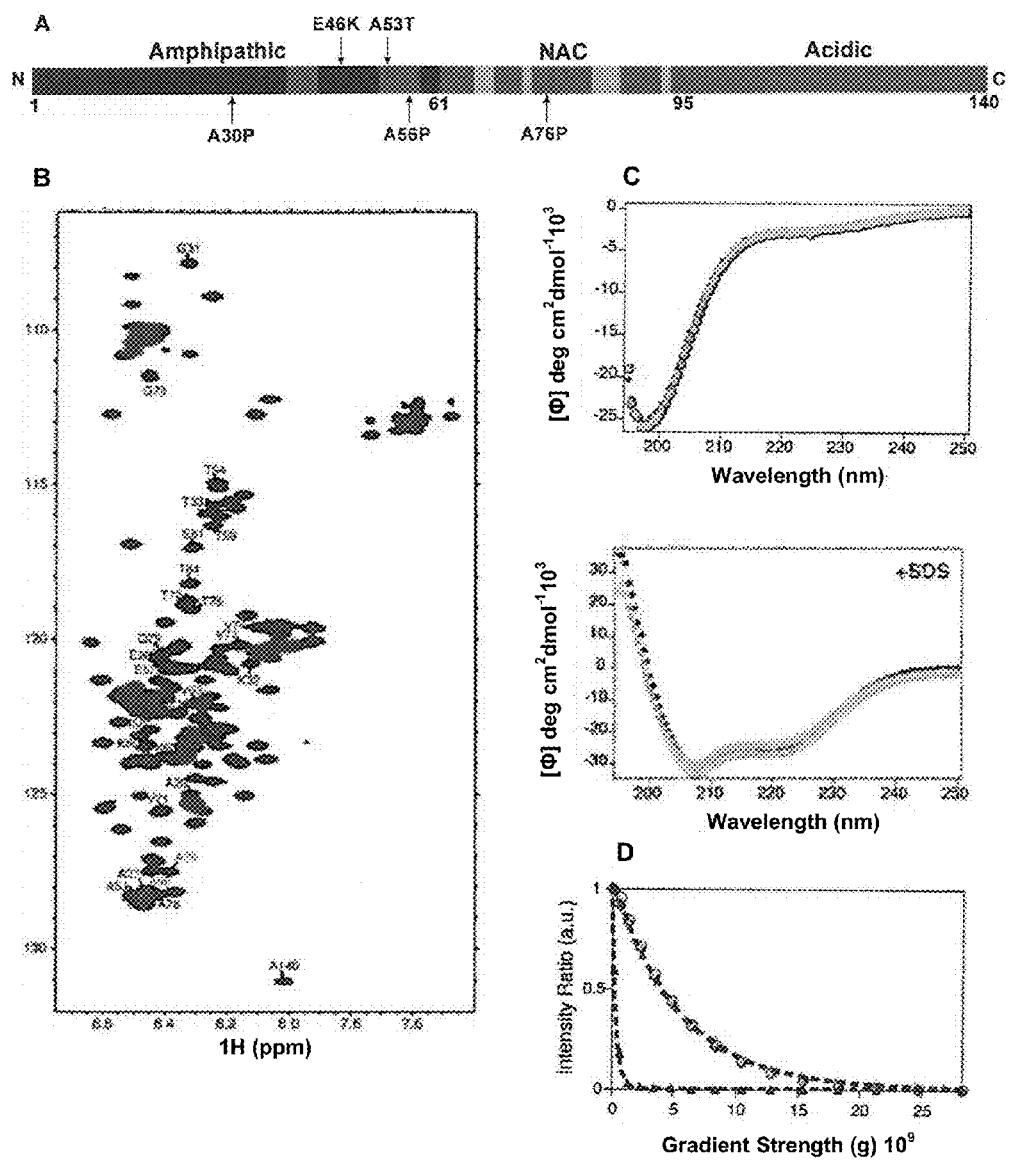
FIG. 1. Structure-based design of alpha-S mutants.

A design of alpha-S variants that aims at the production of toxic species should keep the structural and functional properties of the respective multimers nearly constant. The design was based on the conformational properties of the alpha-S monomer in solution and the topology of alpha-S fibrils known from previous solid-state nuclear magnetic resonance (NMR) measurements (Lee et al., supra; Heise et al. *Proc Nati Acad Sci USA* 102, 15871-15876 (2005)). The genetic mutation A30P is located in a region of alpha-S that is statically disordered in amyloid fibrils (Heise et al., supra). To interfere with aggregation, the single proline mutation found in the genetic mutant were moved to a position that is part of the beta-sheet rich core of alpha-S fibrils (FIG. 1A). The alanine residues 56 and 76 were selected as they are characterized by relatively large residual dipolar coupling values in the soluble monomer, suggestive of a rigid nature (Lee et al., supra; Bertoncini et al., 2005).

Cloning, Expression, and Purification of Alpha-S Variants pT7-7 plasmid encoding for human wt alpha-synuclein (alpha-S) was kindly provided by the Lansbury Laboratory, Harvard Medical School, Cambridge, Mass. A codon replacement was performed for residue Y136 (TAC to TAT) for codon usage concerns. The resulting construct was then used as the template for mutagenesis reactions. Mutations were performed by using the QuickChange site-directed mutagenesis kit (Stratagene) and verified by DNA sequencing. Plasmids containing alpha-S variants were expressed in *Escherichia coli* BL21 (DE3) cells. Following transformation, cells were grown in LB in the presence of ampicillin (100 μg/ml). Induction of expression was performed by 1 mM IPTG at 37° C. for five hours and cells were then harvested by centrifugation. Cell lysis was performed by three consecutive freeze-thaw cycles that were followed by sonication. The majority of the host cell proteins were then denatured by incubation of the crude extract at 95° C. for 20 min in a water bath and the supernatant containing the soluble protein fraction was recovered by centrifugation. Streptomycin sulfate was added to the supernatant to a final concentration of 10 mg/ml and the mixture was gently rotated for 15 minutes at 4° C. After centrifugation, the supernatant was collected and ammonium sulfate was added slowly to a final concentration of 0.36 g/ml. The solution was stirred for 15 minutes at 4° C. and centrifuged. The resulting pellet was resuspended in 25 mM Tris-HCl (pH 7.7). After overnight dialysis against the same buffer, anion exchange chromatography was performed at room temperature on a AKTA Basic system (Amersham Pharmacia Biotech) by using a POROS 20 HQ (Pharmacia Biotech) column. The protein was eluted in a linear NaCl gradient. Subsequent size-exclusion chromatography over HiLoad Superdex 75 (Pharmacia Biotech) ensured a high purity of alpha-S samples. Finally, the protein was dialysed overnight against buffer. The protein concentration was estimated from the absorbance at 280 nm using an extinction coefficient of 5960 M-1 cm-1. For production of 15N-labeled proteins, M9-minimal medium supplemented with 15NH4Cl (Cambridge Isotope Laboratories) was used. For double labeled solid-state samples, 13C-Glucose (Cambridge Isotope Laboratories) was also added to the M9-minimal medium.

The following alpha-S variants were generated: the genetic mutant A30P, the single-proline design mutants A56P, A76P, the double mutants A30PA56P and A30PA76P, and the triple mutant A30PA56PA76P (TP alpha-S), respectively. Based on the known beta-breaking propensity of proline residues, these mutations are expected to cause an increasingly strong delay in aggregation.

Nuclear Magnetic Resonance (NMR) Spectroscopy

NMR samples contained ~0.2 mM 15N-labeled wt or mutant alpha-S in 50 mM Na-phosphate buffer, 100 mM NaCl at pH 7.4 and 90% $H_2O$/10% $D_2O$. The experiments were recorded on a Bruker Avance 600 MHz NMR spectrometer. The temperature was set to 15° C. unless otherwise stated. Data processing was performed using the software packages Topspin (Bruker) and Sparky (Goddard, T. D., Kneller, D. G., University of California, San Francisco). For chemical shift analysis, $^1H$—$^{15}N$ Heteronuclear Single Quantum Coherene (HSQC) 2D spectra were recorded. Mean weighted $^1H$—$^{15}N$ chemical shift differences were calculated according to $\Delta\delta=\{[(\Delta\delta^1H)2+((\Delta\delta^{15}N)/5)2]1/2\}/2$. NMR experiments on SDS micelle-bound alpha-S were performed by addition of deuterated SDS directly to the protein sample prior to the measurement to a final concentration of 40 mM. Measurements were performed at 40° C.

Pulse field gradient NMR experiments were performed with the PG-SLED (pulse gradient stimulated echo longitudinal encode-decode) pulse sequence (Jones et al. *Journal of Biomolecular NMR* 10, 199-203 (1997)). Sixteen one dimensional $^1H$ spectra were collected as a function of gradient strength varying between 2% and 95% of its maximum value. Acqusitions were performed using 16000 complex data points with 32 scans per increment and a relaxation delay of 3 s. Samples contained ~0.2 mM unlabeled wt or mutant alpha-S in deuterated 50 mM Na-phosphate buffer, 100 mM NaCl at pH 7.4. As an internal hydrodynamic radius standard and viscosity probe, 0.1% 1,4-dioxane was included. After baseline correction, the decay in the intensity of the signals from the aliphatic region was fitted as a function of gradient strength (g) to the equation $f(g)=Ae^{-d(g^{-2})}$.

To follow the consumption of monomeric alpha-S by NMR, 0.5 ml samples containing 0.1 mM alpha-S in 50 mM Na-phosphate, 100 mM NaCl, 0.1% $NaN_3$, pH 7.4 and 90% $H_2O/10\%$ $D_2O$ were incubated at 37° C. and stirred by 5×2 mm stirring bars inside a standard NMR tube. At appropriate time intervals, 1D $^1H$ spectra were measured. Spectra were baseline corrected and the decay in signal intensity was plotted as a function of time.

Circular Dichroism (CD) Spectroscopy

Far UV-CD measurements were performed on a Chirascan (Applied Photophysics, UK) circular dichroism spectrometer, using a protein concentration of 10 μM in 50 mM Naphosphate, 100 mM NaCl, pH 7.4 in a quartz cuvette with 0.1 cm light-path. In case of SDS micelle samples, a concentration of 40 mM SDS was added. Recordings were performed over the range of 190-250, with 0.5 nm steps and 2 seconds per point. The spectral bandwidth was 1 nm. Each experiment was repeated at least twice. Baseline correction was performed with the suitable buffer. Data were expressed as mean residue ellipticity (degree $cm^2$ $dmol^{-1}$).

Binding of aS Variants to Small Unilamellar Vesicles (SUV)

1-Palmitoyl-2-Oleoyl phosphatidyl choline (POPC) and 1-Palmitoyl-2-Oleoyl phosphatidic acid (POPA) were obtained from Avanti Polar Lipids. Vesicles were prepared from synthetic phospholipids in the following ratios: POPC/POPA (1:1). The lipids were dissolved together in a 4 ml mixture of chloroform/methanol (1:1 vol/vol), followed by the evaporation of all solvents under a stream of $N_2$ gas and lyophilized overnight. The resulting lipid film was hydrated in 20 mM TrisHCl (pH 7.4), 100 mM NaCl or in 50 mM Na-phosphate buffer (pH 7.4), 100 mM NaCl to obtain a total lipid concentration 12.5 mM. For preparation of SUV, the Suspension was bath sonicated at 37 kHz (4 times for 10 min with 5 min breaks at room temperature) in a glass tube, and the SUV were isolated by ultracentrifugation at 55,000 rpm in a Beckman TLA 100.3 rotor for 2 hours at 298 K. The isolated SUV exhibited hydrodynamic diameter of 20 nm±5 nm from dynamic light scattering. SUVs were mixed with purified alpha-S variants at 250:1 mass ratio of phospholipid to protein for 5 hours at room temperature, then subjected to gel filtration on a Superose 6 10/300 GL column (GE healthcare) at a flow rate of 0.5 l/min. The peak volume (detected by UV at 280 nm) at the elution position of free synuclein was integrated and compared to the corresponding peak volume obtained in the absence of SUV.

Results

The biophysical properties of wt and mutant alpha-S monomers were very similar. As expected, the chemical shift changes observed in $^{15}N$—$^1H$ heteronuclear single quantum coherence spectra by liquid-state NMR spectroscopy were small and restricted to the vicinity of the replaced residues, indicating that mutation-induced structural changes are only subtle (FIG. 1B and FIG. 5). Moreover, secondary structure and hydrodynamic radius of the alpha-S monomer were not affected, as observed with circular dichroism and pulsed field gradient spectroscopy assays, respectively (FIG. 1C,D). Furthermore, the alpha-S mutations do not prohibit the interaction with negatively charged micelles and subsequent alpha-helix formation (FIG. 1C and FIG. 6), two features of alpha-S that are potentially important for its cellular function.

Next we quantified the amount of alpha-S bound to SUVs, which were formed by a 1:1 mixture of 1-Palmitoyl-2-Oleoyl phosphatidyl choline (POPC) and 1-Palmitoyl-2-Oleoyl phosphatidic acid (POPA). Gel filtration of αS-SUV mixtures (phospholipid to protein mass ratio of 250:1) revealed that more than 95% of wt and A53T alpha-S are bound to SUVs when using Tris buffer (Table 1 and FIG. 22). In case of A30P alpha-S, only 70±3% of the total protein was bound to POPC:POPA SUVs. A value very similar to that observed for A30P was obtained for A56P alpha-S. In addition, the affinity of TP alpha-S was only very slightly reduced compared to A30P and A56P alpha-S, with 66±3% of SUV-bound protein (Table 1). When phosphate buffer was used instead of Tris, the overall amount of SUV-bound alpha-S was reduced, but relative differences between different alpha-S variants were very similar (A53≈wt>A56P≈A30P≥TP) (Table 1). In addition, the content of alpha-helix, which was detected by CD spectroscopy for the alpha-S variants in the SUV-bound state, followed the amount of SUV-bound protein (wt≈A53>A56P≈A30P≥TP) (FIG. 21 and Table 1).

TABLE 1

Alpha-helical content of alpha-S variants bound to POPC:POPA SUVs.

| Sample (POPC/POPA 1:1) | Secondary structure predictions by K2D* alpha-Helix (%) |
|---|---|
| WT | 52 |
| A30P | 31 |
| A53T | 46 |
| A56P | 35 |
| TP | 27 |

Determined using the K2D web server (http://www.embl-heidelberg.de/~andrade/k2d.htm).

Example 2

In Vitro Fibril Formation

Preparation of Alpha-S Aggregates

Recombinant human wt and mutant alpha-S solutions were dialysed against 50 mM Na-phosphate buffer with 100 mM NaCl at pH 7.4 unless otherwise stated. To remove any potential seed prior to aggregation, ultracentrifugation was performed in a Beckman ultracentrifuge equipped with TLA.100 rotor (Beckman Coulter) at 60000 rpm for 2 h at 4° C. Supernatant was filtered through 0.22 μm filter. Protein concentration was adjusted to 100 μM unless otherwise stated. 0.01% sterile filtered $NaN_3$ was included in the aggregation mixtures, which were then incubated in glass vials at 37° C. with constant stirring at 200 rpm on a multi-position magnetic stirring device (Variomag Telesystem 15.40, H+P Labortechnic AG, Germany). For every experiment, at least triplicates were prepared.

For seeded incubations, 200 μM solutions of TP alpha-S were incubated for five days at 37° C. prior to seeding. For electron microscopy, 50 mM HEPES 100 mM NaCl pH 7.4 was used. Without further purification or attempt to separate monomers from oligomers, the solution, which contained monomers and oligomers of TP aS, was added to wt monomeric alpha-S at an equimolar ratio. As control, we performed an aggregation assay, in which monomeric TP alpha-S was added to monomeric wt alpha-S at an equimolar ratio. Error bars in FIG. 2 D represent mean±Standard deviation of three to four independent experiments.

NMR Spectroscopy

NMR spectroscopy was carried out as described in Example 1. The drop in signal intensity during aggregation is due to formation of higher molecular weight aggregates not detectable by solution-state NMR. Thus, the NMR signal intensity remaining during the course of the aggregation allows estimation of the concentration of monomeric protein. Simultaneously performed EM measurements, which were performed in the early stages of the aggregation, only showed small oligomeric species and no amyloid fibrils. In addition, no increase in ThioT signal compared to the monomeric protein was detected during the lag phase. Thus, the reduction of NMR signal intensity during the lag phase of fibril formation allows estimation of the concentration of soluble oligomers. In case of the NMR aggregation assay performed for TP alpha-S at a concentration of 0.1 mM (FIG. 18C), no amyloid fibrils were detected during the complete time course of the experiment, indicating that the reduction in signal intensity is solely due to formation of soluble oligomers. Errors in the estimation of the oligomer concentration depend on the basis of the signal-to-noise ratio in the NMR spectra and are determined from the variation observed in three independently performed aggregation assays. In case of TP alpha-S, they were ±2%.

Thioflavin T (ThioT) Fluorescence Measurements

Aliquots (5 μl) were withdrawn from alpha-S incubations and added to 2 ml of 5 μM ThioT in 50 mM Glycine-NaOH pH 8.2. Fluorescence measurements were carried out on Cary Eclipse Spectrofluorometer (Varian) using 3.5 ml quartz cuvettes (Hellma, Germany) with a path length of 1 cm. Fluorescence emission spectra were recorded from 465 to 600 nm, using excitation wavelength of 446 nm, an integration time of 0.1 second, and both excitation and emission bandwidths of 10 nm. Kinetic aggregation traces were generated from time traces of ThioT fluorescence intensity at 482 nm and corrected for free ThioT fluorescence. Aggregation yields were normalized to the final values and the averaged data points were fitted to a sigmoidal equation. (Data was represented as mean±standard deviation, n=3).

Dynamic Light Scattering (DLS)

To monitor the build-up of oligomeric intermediates of alpha-S, aliquots of 15 μl were withdrawn from the aggregation mixture at different time intervals and measurements were performed directly on a DynaPro Titan instrument (Wyatt Technology) at 25° C. Data analysis was performed with the built-in software DYNAMICS from 30 successful measurements. For the higher concentration samples (0.8 mM), 10 μl aliquots were taken at the end of incubation (11 days), then diluted 8-fold with the buffer and centrifuged at 14000 rpm for 30 minutes, and the supernatant was measured on a DLS machine. The same laser power was used for all alpha-S variants. Data analysis was performed with the built-in software DYNAMICS from 30 successful measurements.

UV Spectroscopy

After 11 days of incubation of 0.8 mM alpha-S solutions in the aggregation condition, 10 μl aliquots were taken out and diluted 8-fold with the buffer. Thereafter, the samples were centrifuged at 14000 rpm for 30 minutes and the supernatant was investigated for apparent UV absorbance in the 210-310 nm range.

Transmission Electron Microscopy (TEM)

For negative staining, a solution containing protein was applied to glow-discharged carbon coated grids and stained with 1% uranyl acetate. Images were taken in a Philips CM120 electron microscope (Philips Inc.) at a defocus of 2.3 μm using a TemCam 224A slow scan CCD camera (TVIPS, Gauting, Germany).

Atomic Force Microscopy (AFM)

A TP alpha-S solution (0.8 mM) in 50 mM HEPES, 100 mM NaCl, pH 7.4, with 0.01% NaN3 was incubated at 37° C. with stirring at 200 rpm. An aliquot of 2 μl was diluted 8-fold in the above-mentioned buffer and 4 μl of the diluted sample were deposited on freshly cleaved mica. After drying in air for 1 hr, unbound sample and buffer were washed out with 100 μl of distilled water. The samples were imaged using an Asylum MFP3D AFM machine, with a resonant frequency of about 100 kHz, a scan frequency of 1 Hz, using silicone nitride tips.

Solid-State NMR Spectroscopy

For solid-state NMR measurements, 200 μM 13C- and 15N-labeled A56P alpha-S was incubated for two weeks and 200 μM 13C- and 15N-labeled TP alpha-S was incubated for four weeks at 37° C. and 200 rpm. Subsequently, alpha-S aggregates were recovered by centrifugation at 60000 rpm for 2 h at 4° C. (TLA.100, Beckman ultracentrifuge). Two-dimensional NMR experiments were conducted on 14.1 T ($^1$H resonance frequency: 600 MHz) and 18.8 T ($^1$H resonance frequency: 800 MHz) NMR instruments (Bruker Biospin, Germany) equipped with 4 mm triple-resonance ($^1$H, $^{13}$C, $^{15}$N) MAS probes. All experiments were carried out at probe temperatures of 0° C. MAS rates were set to values that facilitate sequential correlations at longer mixing times, i.e., 9375 Hz at 600 MHz and 12500 Hz at 800 MHz. Resonance assignments for A56P alpha-S and a residue-specific analysis of beta-strands in alpha-S variants was based on sequential ($^{13}$C—$^{13}$C) correlation data obtained at mixing times of 150 ms (data not shown).

Dot Blotting

Purified recombinant proteins were spotted onto nitrocellulose membrane. Blotting was performed using the conformation-specific A11 antibody (Invitrogen's Biosource). The amount of protein used for each spot was 10 μg. In a parallel experiment, same samples were blotted using the anti-alpha-S antibody (BD Biosciences). The amount of the protein used was 1 μg.

Results

Despite the high structural resemblance of the monomeric proteins, fibril formation in vitro and in cells was dramatically reduced by the alpha-S mutations (FIG. 2 and FIG. 9). Whereas 0.1 mM of wt and A30P αS formed fibrils after about 20-30 hours as probed by thioflavin T (ThioT) fluorescence, A56P, A30PA56P and A30PA76P alpha-S had an approximately five time longer lag phase (FIG. 2A and FIG. 9). In addition, their fibril elongation rate was strongly reduced suggesting a reduced cooperativity of the transition. TP alpha-S did not show any fibrils even after two weeks of incubation (FIG. 2A). However, electron microscopy and dynamic light scattering detected pre-fibrillar TP alpha-S aggregates already at an early stage of the aggregation process (FIG. 2c and FIG. 7). A quantitative analysis of the NMR signal decay showed that after 50 hours of incubation at 37° C. and 0.1 mM protein concentration the oligomeric intermediates constituted a 6% and 2% fraction of the protein mixture for A56P and TP alpha-S, respectively. In case of TP alpha-S, the oligomeric fraction increased to 4% after 160 hours (FIG. 2B).

Dynamic light scattering identified high molecular weight species with both A56P and TP alpha-S (FIG. 2C). The hydrodynamic radius was approximately 100 nm, a value very similar to that observed with oligomers of wt and A30P alpha-S (FIG. 2C and FIG. 8). Measurement of monomer consumption throughout the aggregation by 1D $^1$H NMR spectroscopy revealed that the oligomeric intermediates formed by A56P and TP alpha-S constitute a 6% and 2% fraction of the protein mixture after 50 hours, and a 40% and 4% fraction after 160 hours respectively (FIG. 2B). A mixture of oligomeric and monomeric TP alpha-S, which was obtained after five days of aggregation of TP alpha-S at 37° C. and 0.2 mM protein concentration, was able to seed fibril formation of monomeric wt alpha-S (FIG. 2D). In contrast, addition of the same concentration of purely monomeric TP alpha-S did not accelerate aggregation of wt alpha-S. In addition, the mixture of oligomeric and monomeric TP alpha-S was recognized by the conformation-specific antibody A11 (FIG. 2E), which detects a variety of toxic amyloid oligomers. Notably, the TP oligomers were not resistant to sodium dodecyl sulfate (data not shown).

Increasing the concentration to 0.8 mM significantly accelerated the rate and amount of aggregation and amyloid formation of all alpha-S variants (FIG. 2G). At 0.8 mM protein concentration, wt and A30P alpha-S had a distinct lag phase of about 9-12 hours, whereas ThT reactivity of A53T rose from the beginning (inset in FIG. 2G). On the other hand, A56P started to form ThioT-positive fibrils after about 72 hours and TP alpha-S displayed a clear but very slow rising ThioT signal only after about 5 days of incubation (FIG. 2G). Surprisingly, the strongest ThioT signal after 5 days of incubation was observed for A30P alpha-S, followed by wt and A53T alpha-S. This is most likely caused by the very gel-like behaviour of the aggregated wt, A30P and in particular A53T alpha-S sample that interfered with ThioT binding. The samples of A56P and TP alpha-S were much more fluid, indicating that a smaller amount of fibrils was formed. In addition, A56P and TP alpha-S had strongly reduced fibril elongation rates. Whereas for wt, A30P and A53T alpha-S it took about 20 hours to reach the saturating ThioT signal from end of the lag phase, this time was increased to about 60 hours in case of A56P alpha-S. With TP alpha-S a saturating ThioT signal could not be reached within the experimental time, indicating that it has an extremely slow fibril elongation rate (FIG. 2G).

Electron microscopy of wt, A30P, A53T and A56P alpha-S samples after 6 days of incubation (protein concentration of 0.8 mM) revealed a high number of fibrils of about 8 nm in diameter and various lengths but without clearly observable oligomeric species. In case of TP alpha-S, the fibrils were significantly lower in number, longer and frequently associated with oligomers of various shapes and sizes (FIG. 2O and FIG. 17A). Atomic force microscopy of the TP alpha-S sample showed a similar picture, with the presence of fibrils of about 8 nm in diameter, and oligomers of 20-100 nm in diameter (FIG. 17B).

The aggregation process of the alpha-S variants was further investigated by dynamic light scattering and electron microscopy. Dynamic light scattering revealed the formation of soluble oligomers with a hydrodynamic radius of approximately 80-180 nm after six hours of incubation in the aggregation assay employing protein concentrations of 0.1 mM (FIG. 8). In the same assay, a heterogeneous distribution of larger species was observed for all alpha-S variants after 12 hours of incubation by electron microscopy (FIG. 8).

In addition, DLS was used to study the soluble oligomers of alpha-S, which were formed after 11 days of incubation. At protein concentrations of 0.8 mM, fibrils were observed for all alpha-S variants (see above and FIG. 17A). The fibrillar material was separated from soluble oligomers by centrifugation at 14,000 rpm for 30 minutes and careful pipetting of the upper 50% of the supernatant. DLS measurements of the supernatant samples showed quite different scattering patterns for the different alpha-S variants. The smallest scattering intensity was observed for wt alpha-S (FIG. 17C). A30P and A53T alpha-S had very similar scattering intensities, which were slightly larger than that of wt alpha-S, and for A56P alpha-S the scattering intensity was further increased. The most dramatic increase, however, was seen for TP alpha-S, for which the scattering intensity of the supernatant sample was an order of magnitude higher than in case of the wt protein (FIG. 17C) and mostly caused by 140-170 nm oligomeric species. The UV absorbance spectrum of the supernatant showed a very similar trend for the alpha-S variants (FIG. 17D). The combined EM, AFM, DLS and UV data indicate that A56P and in particular TP alpha-S have an impaired ability to form amyloid fibrils, but soluble oligomers accumulate in later stages of the aggregation.

The late-stage aggregates of A56P and TP alpha-S were characterized at single residue resolution by solid-state NMR (ssNMR) spectroscopy (FIG. 10). For both A56P and TP alpha-S, magnetization transfer from water to the protein proceeded with the same rate suggesting that the relative water-accessible surface in these fibrils was similar to that of fibrils from wt protein (FIG. 10A). Assuming a cylindrical (proto)fibril model, we estimated fibril diameters of about 60 Å for all three cases. However, cross peak signals in sequential ($^{13}C,^{13}C$) correlation experiments conducted on A56P alpha-S were absent around the mutation site (e.g. Y39, S42, T54 and A56) but were identified for the other three beta-strand segments previously seen for the wt, A30P and A53T protein (Heise et al., 2005) (FIG. 10B). In addition, we detected alterations in chemical shifts for residues including T75, Q79, I88, and E83, indicative of a perturbed beta-strand structure. These findings point to a reduced beta-sheet content in late stage aggregates of A56P alpha-S compared to wt, A30P and A53T alpha-S. Concomitantly, we detected in ssNMR experiments probing mobile A56P fibril segments an enhanced contribution from residue types such as threonine, which are found in the residue stretch 22-93 (FIG. 10C). For TP alpha-S, a further significant reduction of cross-peak correlations was detected (FIG. 10D) under experimental conditions comparable to A56P, consistent with structural alterations or increased dynamics/disorder in the last two beta-strands (FIG. 10E).

Collectively, these results indicate that there were only subtle changes with respect to the biophysical properties of mutant versus wild type alpha-S protein with the exception that the aggregation process was drastically slowed down.

Example 3

In Vivo Fibril Formation
Human Embriyonic Kidney (HEK) Cell Cultures
Cell Culture HEK293 cells were cultured in Dulbecco's MEM (PAN-Biotech, Aidenbach, Germany) with 10% fetal calf serum and 1% penicillin-streptomycin. Cells were transiently transfected using Metafectene (Biontex Laboratories, Martinsried, Germany), following the manufacturer instructions. For imaging, cells were grown on poly-L-lysine (Sigma, Munich, Germany) coated glass coverslips and used 24 h after transfection. For staining of chromatin and F-actin, cells where submerged in PBS with 0.5 µg/ml of Hoechst 33258 (Invitrogen) and 1:500 of Alexa-568 conjugated phalloidin (Invitrogen) for 15 min at room temperature and washed 3 times in PBS. Coverslips were mounted on glass slides using mounting medium consisting of 24% w/v Glycerol, 0.1 M Tris-base pH 8.5, 9.6% w/v Mowiol 4.88 (Calbiochem, Darmstadt, Germany) and 2.5% w/v of DABCO (Sigma).

Imaging

Imaging at 24 h was performed at room temperature using an inverted fluorescence microscope (DMI6000B, Leica Microsystems, Bensheim, Germany) with a 63× dry objective (HCX PL FLUOTAR, N.A. 0.7) and a Leica FX350 Camera. For each genotype, 200-300 cells per coverslip from from 4-5 independent experiments were classified manually based on their EGFP distribution as either "homogenous", "with a single aggresome", "with many aggregates" or "preapoptotic". For statistical analysis, One-Way ANOVA was performed with GraphPad Prism 4.00 (GraphPad Software, San Diego, USA). P values were derived from Dunnett's post-tests. All comparisons were made against the control PDZ-EGFP alone. Bars depicted in the graphs represent mean±standard error of the mean.

Quantitative rtPCR.

Total RNA was isolated from HEK293 cells 24 h after transfection using the RNeasy Mini Kit (Quiagen, Hilden, Germany). RNA was digested by RQ1 RNase Free DNase (Promega, Mannheim, Germany) and protected against RNases by adding 20 U of RNase Inhibitor RNasin (Promega, Mannheim, Germany). 2.5 mg of total RNA was used for reverse transcriptase PCR (M-MLV; Promega, Mannheim, Germany). cDNA was diluted 1:50 and real-time reaction samples were prepared using ABsolute QPCR SYBR Green (ABgene, Hamburg, Germany), according to the manufacturer instructions. Real-time PCR was performed in a Stratagene Mx3000P Realtime device (Stratagene, La Jolla, Calif.). Primers for detection of a-synuclein were Fw__5'CAG GGTGTGGCAGAAGCAGC3' (SEQ ID NO: 4) and Rv__5'CTGCTGTCACACCCGTCACC3' (SEQ ID NO: 5). Eucariotic 18s ribosomal mRNA was chosen as reference gene and quantification calculated using the comparative 2-ΔΔCt method. Water and pEGFP-N1 transfected cells were used as negative controls. Three independent experiments (n=3) were performed, each with triplicates. Significance of expression differences, were tested using one-way ANOVA, which was not significant.

Western Blot.

Cells were plated in 6 well plates at equal density and transfected the next day. 24 h after transfection, cells were harvested in phosphate buffered saline (PBS), centrifuged and resuspended in 100 µl of lysis buffer: PBS with 1% TritonX and protease inhibitor cocktail (Pierce, Rockford, Ill., USA). Lysates were cleared by centrifugation (15,000 g, 20 min, 4° C.) and the supernatant transferred to new tubes. 10 µl of each were separated by SDS-PAGE. Primary monoclonal antibody against alpha-S was used over night at 1:1000 and at 4° C. (BD Transduction Laboratories, Cat. #610786). After incubation with the secondary antibody and visualization, the membrane was washed 3 times 20 min with stripping buffer (0.2 M Glycin, 0.5 M NaCl, pH 2.80) and incubated overnight with antibody against GFP (polyclonal; Santa Cruz #SC 8334). The secondary antibodies for both primaries (GE Healthcare, #NXA931 & #NA934V) were coupled to horseradish-peroxidase (1:10000) and visualized independently by chemiluminescence (Alphalmager, Alphalnnotech, San Leandro, Calif.). Quantification of aS signal was normalized against the EGFP signal of the same sample. This is a better expression control since EGFP is in the same vector but under a second CMV promotor). Beta-actin levels were equivalent among the different constructs, but normalizing with beta-actin would control for transfection efficiency, and not for protein expression levels. Tree independent experiments (cells plated, transfections and western blots) were performed.

The in vivo formation of insoluble aggregates in human embryonic kidney (HEK) cells was tested after expression of fluorescently labelled A30P, A53T, A56P and TP alpha-S, having a six-amino acid PDZ binding motif for recognition by enhanced green fluorescent protein (EGFP). Equal expression levels of all alpha-S variants were verified by quantitative PCR and Western blot (FIG. 18). A second, independent cassette expressed a fusion protein of EGFP and the corresponding PDZ domain (PDZ-EGFP), thus non-covalently labelling alpha-S variants with EGFP. We classified cells based on their EGFP fluorescence to determine the frequency of cells with aggregates and the fraction of preapoptotic cells (see above). Significantly more cells transfected with A30P or A53T alpha-S formed aggregates (as visualized by EGFP fluorescence) as compared to cells expressing the control protein PDZ-EGFP alone (FIGS. 18A and 18B; FIG. 2F, clear bars). In contrast, expression of the design mutants A56P and TP alpha-S mutants did not induce aggregates in more cells than background (EGFP-PDZ alone). Thus, A56P and TP alpha-S fulfilled their design principle, i.e. they show strongly impaired aggregation both in vitro and in living cells. Expression of the genetic mutants A30P and A53T alpha-S resulted in more cells with aggregates and a higher fraction of preapotic cells than control. (FIG. 18A; FIG. 2F, hatched bars). In contrast, expression of A56P and TP alpha-S resulted in toxicity comparable to that observed for A53T alpha-S, despite the observation that the occurrence of aggregates was at background levels (PDZ-EGFP alone). From the induction of toxicity but not aggregates by the design mutants A56P and TP alpha-S we conclude that cellular toxicity in response to alpha-S expression does not require the formation of visible alpha-S aggregates. However, differences in toxicity between A56P and TP alpha-S that are related to aggregation cannot be revealed in this system, as already the single A56P mutation had a dominant effect on aggregation.

Example 4

Intervertebrate Animal Models
C. elegans Experiments
Expression Constructs

As described previously (Pitman et al., supra), a 719 bp dat-1 promoter fragment was PCR amplified and cloned upstream of the start ATG of enhanced gfp in the C. elegans expression vector pPD115.62 (myo-3::gfp; kindly provided by A. Fire) in order to express alpha-S in dopaminergic neurons, replacing the myo-3 promoter creating Pdat-1::gfp. Subsequently alpha-S and its mutant variant were also PCR amplified and cloned as a NdeI/HindIII fragment into the Pdat-1::gfp vector replacing GFP. To create Pdat-1::mCherry, the gfp coding sequence of Pdat-1::gfp was exchanged with that of the red fluorescent protein variant mCherry. To analyze aggregation alpha-S—mYFP citrine fusion proteins were specifically expressed in muscle cells under the control of the myo-3 promoter of pPD115.62. Wt and TP alpha-S were PCR amplified without stop codon for C-terminal fusion and cloned along with mYFP citrine into pPD115.62 replacing GFP, resulting in Pmyo3::αS-YFP. All constructs were verified by sequencing. A11 constructs were verified by sequencing.

Transgenic Animals

C. elegans strains were cultured as described previously (Brenner, S., supra) and kept at 20° C. if not otherwise stated. To create transgenic animals expressing alpha-S or its mutants in dopaminergic neurons the gonads of young adult wild type N2 hermaphrodites were injected with a plasmid mix of Pdat-1::alpha-syn (60 ng/µl) and Pdat-1::mCherry (40 ng/µl) as co-injection marker. The concentration of the alpha-S expression constructs were chosen such that wild type alpha-S expression at this given concentration shows only a weak phenotype. The concentration of all other alpha-S expression constructs was kept constant accordingly. To express mYFP citrine tagged alpha-S variants in body wall and sex muscles a plasmid mix containing Pmyo3::αS-mYFP (40 ng/µl) and the coinjection markers pRF4 (rol-6 (su1006sd); 40 ng/µl) and Pttx3::gfp (10 ng/µl) were injected. To allow comparable expression levels, the injection mix was always adjusted to a total DNA concentration of 100 ng/µl by adding pBlueScript SKII (Stratagene). Only transgenic lines showing highly uniform expression were selected and similar levels of alpha-S expression were confirmed by RT-PCR and Western Blot. Alpha-S was detected using a polyclonal rabbit αS antibody (Anaspec). All blots were normalized against alpha-tubulin using monoclonal Ab 12G10 (DSHB). To image alpha-S-mYFP aggregation in muscle cells 10 day old trangenic animals were anesthetised and imaged using the UltraviewVOX spinning disk microscope (PerkinElmer). At least two independent strains per alpha-S variant were imaged. Vulva muscles were scored positive if at least one fibrilar aggregate was visible.

Microscopy and Behavioral Analysis

C. elegans contains eight dopaminergic neurons which are involved in food sensation. These neurons have been widely used as an accepted model system to mimic Parkinson related phenotypes in C. elegans. As in the human system exposure of the worm to 6-hydroxydopamine (6-OHDA) or MPTP results in a specific degeneration of dopaminergic neurons and associated alterations in dopamine controlled behaviors. Furthermore, this toxicity is dependent on the presence of the dopamine transporter DAT-1 as no degeneration is observed in dat-1 mutant animals or if dopamine transporter inhibitors are used. Thus C. elegans can also be used to test and find neuroprotective compounds (Marvanova & Nichols Journal of Molecular Neuroscience 31, 127-137 (2007)). This exemplifies that the dopaminergic system of C. elegans is highly similar to mammalian system and can therefore be used as a model to assay the neuronal physiology linked to Parkinson's disease (PD). Accordingly, expression of alpha-S or its mutant versions linked to PD specifically in dopaminergic neurons have been shown to cause neuronal toxicity and degeneration (Pitman et al., supra; Shaw et al. Science 287, 1834-1837 (2000)). Interestingly, in C. elegans familial PD linked A30P alpha-S and A53T alpha-S exhibit an increased neuronal toxicity as compared to wild type alpha-S (Pitman et al., supra).

Routinely, transgenic animals were imaged or assayed four days after reaching adulthood at least three independent strains per transgene were tested. To image dopaminergic neurons, transgenic animals were anesthetized by 50 mM sodium azide in M9 buffer and mounted on a 2% agarose pad. RFP positive dopaminergic neurons were visualized using a Leica SP2 confocal microscope system. Neurite defects were scored positive if one or more dendritic processes out of four had degenerated. For each transgenic strain at least 75-80 animals were tested.

As a response to the presence of food wild type animals slow down their movement and reduce their area restricted searching behavior in order to feed more efficiently. This dopamine-controlled behavior is absent when dopaminergic neurons are ablated or not functional. Therefore, this behavior allows to directly assess the functional integrity of dopaminergic neurons in C. elegans. For behavioral analysis wellfed adult animals were transferred to the center of an assay plate with or without food as described previously (Brenner, supra). After an initial time of adjustment for 5 min the movement was assayed by counting body bends over a one min interval with three repetitions per animal. The slowing rate was calculated and defined as the percentage of locomotion on food as compared to the locomotion on plates without food. For each transgenic strain at least 35-50 animals were tested in double blind fashion. Each trail was repeated three times.

Drosophila Experiments

Generation of Transgenic Flies

The site-specific recombination system based on φC31 integrase was used to generate transgenic flies (Sawin et al. Neuron 26, 619-631 (2000)). The targeting constructs were prepared by cloning the cDNAs of alpha-S variants into the GAL4-responsive pUAST expression vector containing attB site (attachment site B). The resulting plasmids were then injected into the fly embryos, which are double homozygous for both attP (attachment site P) site and germ-linespecific φC31 integrase. The genomic location of the attP landing site used for integration was mapped to the 3R-86Fb position in the genome (ZH φX-86Fb line) (Sawin et al., supra). All the site-specific insertions were verified by single fly PCR using the primer pairs: 5'ACT GAA ATC TGC CAA GAA GTA 3' (SEQ ID NO: 2) and 5'GCA AGA AAG TAT ATC TCT ATG ACC 3' (SEQ ID NO: 3). In order to compare the ddc-Gal4 driven protein expression levels in transgenic animals expressing different variants of alpha-S, SDS-PAGE and subsequent western blotting were performed from fly head extracts as described previously (Edery et al. Proc Natl Acad Sci USA 91, 2260-4 (1994)).

Immunohistochemistry.

Whole-mount adult fly brains from the 28-30 day old animals were prepared and immuno-stained. Rabbit anti-tyrosine hydroxylase (TH) (1:150; Chemicon International, Temecula, Calif.) was used to positively stain the DA neurons, and Mouse anti-nc82 (1: 200; Developmental Studies Hybridoma Bank, University of Iowa, Iowa City, Iowa) was used as a counter stain. From the confocal sections of fly brains of different genotypes, DM and DL clusters of DA neurons were defined and counted by using the ImageJ64 software (National Institutes of Health, Maryland, USA) (10-15 brains per genotype; two independent experiments).

Behavioral Analysis

Longevity Assay

Flies expressing alpha-S variants and control animals expressing lac Z were collected and maintained under LD 12:12 at 25° C. with constant humidity and population density per vial. Flies were transferred to the fresh food vials and scored for survival every 5 days. Survival curves were calculated and plotted using Kaplan-Meier statistics, and differences between them were analysed by using the log rank method (GraphPad Prism software, San Diego, USA).

Sleep Assay

Fly embryos of different genotypes were collected in 2 hour window periods, and were grown under LD 12:12 at 25°

C. before the eclosion. Males were collected from the progeny and aged with equal population density under LD 12:12 at 25° C. After 25-30 days, locomotor activity of the aged flies was recorded in LD by the *Drosophila* Activity Monitoring (DAM) system (Trikinetics, Waltham, Mass.) as described in (Hendricks et al. *Nat Neurosci* 4, 1108-15 (2001); Hendricks et al. *Neuron* 25, 129-38 (2000)). Sleep was measured as bouts of 5 min of inactivity, using a moving window of 1 min intervals. Average bout length (ABL) was calculated from the sum of sleep bouts of all lengths (in minutes) divided by the total number of sleep bouts.

Climbing Assay

Flies expressing different alpha-S variants were placed in an apparatus containing a bottom vial and an inverted upper vial. They were assayed for their ability to reach upper vial from the bottom vial in twenty seconds. During the assay, to avoid photic effects from outside environment, both vials have been encased in black cases. Since flies generally get attracted towards light, a light source at the top of upper vial with the help of two light emitting diodes was also provided. This type of set up provides a directionality and motivation for the flies to climb up.

Results

To further explore the consequences of delayed alpha-S aggregate formation in living organisms and to elucidate its functional consequences, the impact of the biophysically characterized alpha-S mutants on various behavioural aspects related to PD in model organisms such as locomotor activitiy of fly *Drosophila melanogaster* and the nematode *C. elegans* was tested. Expression levels of all alpha-S variants in a neuspecific model system were comparable (FIGS. 18, 19 and 23).

*C. elegans*

When expressed in muscle cells of *C. elegans*, wt alpha-S had been shown to form aggregates in an age dependent manner. To demonstrate that the TP variant of alpha-S has a strongly impaired ability to form insoluble aggregates in vivo—as has been shown in vitro—we expressed wt and TP alpha-S as a fusion to monomeric YFP in body wall and sex muscles of *C. elegans* and followed its aggregation with time. As reported previously aggregates of wt alpha-S-mYFP are first detected in six-day old adult muscles and at day 10 large fibrillar aggregates were visible in most muscles (86% and 75% in 25 animals analyzed in each of two independent stains, respectively) (FIG. 19A). In contrast, at day six no TP alpha-S-mYFP aggregates could be detected in any of the transgenic strains and even at day 10 only rare, small TP alpha-S-mYFP aggregates were visible in a few muscle cells (4% and 8% in 26 animals analyzed in each of two independent stains, respectively) (FIG. 19B). The alpha-S-mYFP expression levels were comparable as judged by Western blot analysis and even slightly higher for the TP strains used (FIG. 19C). Therefore, we conclude that, like in vitro, the TP mutations strongly impair fibril formation of alpha-S in vivo.

A hallmark of PD is the progressive loss of dopaminergic neurons in patients. Dopaminergic neurons in *C. elegans* have been successfully used as a model system to assay the toxicity of alpha-S mutants associated with familial PD (Nass & Blakely *Annu Rev Pharmacol Toxicol* 43, 521-544 (2003)). The six dopaminergic neurons in the head of *C. elegans* are cleary visible and morphologically invariant from animal to animal, enabling reliable scoring of morphological defects (Nass & Blakely, supra). To assay alpha-S induced neuronal toxicity, transgenic strains were generated expressing the different alpha-S variants exclusively in dopaminergic neurons of *C. elegans*. As these neurons are dispensable and are not required for viability, their alpha-S induced degeneration can be studied without affecting the animal's fitness. For each expressed alpha-S variant, the morphology of dopaminergic neurons in the head in multiple independent transgenic strains was analyzed. Two representative lines each are shown in FIG. 4B. Transgenic strains overexpressing the genetic mutants A30P (45±5% and 42±4%) and A53T (36±6% and 48±5%) alpha-S developed more neurite defects than control animals expressing wt alpha-S (13±5% and 8±3%) (FIG. 4B). More pronounced neurodegeneration, however, was observed for *C. elegans* strains expressing the designed alpha-S variants A56P (63±3% and 68±3%) and TP (88±2% and 81±3%) (FIG. 4B). Importantly the A56P alpha-S mutant caused more severe neurite defects than the A30P alpha-S mutant. In both alpha-S variants, alanine is replaced by proline within the alpha-S domain that converts from an unfolded conformation in the soluble monomer to an alpha-helical structure by interaction with membrane mimetics. Within this domain, A30 is not part of the rigid beta-structure of alpha-S fibrils whereas A56P carries the replacement right in the center of the second beta-strand (FIG. 1A) (Heise et al., supra). The alpha-S expression levels were similar in all strains studied as shown by Western blot analysis using an alpha-S-specific antibody (FIG. 23). However, the degeneration was not restricted to dopaminergic neurons. When alpha-S was expressed under the control of a pan-neuronal promoter degeneration of other neurons was visible leading to sick animals (data not shown).

In response to the presence of food, *C. elegans* worms slow down movement and reduce the area-restricted searching behaviour. This behaviour depends on dopaminergic neurotransmission and is absent when dopaminergic neurons are ablated or not functional (Sawin et al., supra). Transgenic worms expressing the A56P or TP alpha-S variant in dopaminergic neurons showed a strong impairment of this dopamine (DA)-dependent behaviour. This impairment was strongly enhanced as compared to animals expressing the A30P or A53T mutant or wt alpha-S (FIG. 3A).

*D. melanogaster*

Next wt alpha-S, A53T, A56P or TP alpha-S mutant proteins were expressed in *Drosophila*. To ensure comparable expression of the different alpha-S variants, the corresponding transgenes were targeted to the same genomic location by using the φ-C31 based site-specific recombination system (FIG. 11).

To assess the impact of the alpha-S variants on dopaminergic neurons in *Drosophila*, we immunostained wholemount brains from flies at 2 and 29 day posteclosion with an antibody against tyrosine hydroxylase, which specifically identifies these neurons (FIG. 4C). In young flies overexpressing wt, A53T, A56P and TP alpha-S under control of the pan-neuronal driver elav-Gal4 the number of neurons in the dorsomedial (DM) and dorsolateral (DL) cluster of the brain was not altered when compared to the LacZ control (FIG. 4D). At day 29, however, adult flies expressing A53T and A56P alpha-S demonstrated a marked loss of tyrosine-hydroxylase-positive cells in both clusters (FIG. 4D). An even more pronounced reduction in the number of dopaminergic neurons was observed in flies expressing TP alpha-S, in particular in the DM cluster (FIGS. 4C,D).

Using the pan-neuronal driver elav-Gal4, flies were assayed for motor defects using a climbing assay which addresses the combined geotactic and phototactic response of flies. The loss of the climbing response has been used to monitor aging-related changes in *Drosophila* and to reveal behavioral manifestations of nervous system dysfunction in alpha-S transgenic flies. The climbing abilities of 25-30 day old flies expressing wt alpha-S (or A30P alpha-S according to initial tests) were comparable to those of the LacZ control flies (FIG. 3B). In contrast, flies expressing the genetic mutant A53T alpha-S or the aggregation-impaired design mutant A56P alpha-S showed a reduced climbing ability. In agreement with the lowest number of dopaminergic neurons (FIG. 4D), adult flies expressing TP alpha-S were most strongly impaired (FIG. 3B).

To further explore the effects of wt alpha-S and alpha-S mutants when directly expressed in the dopamine producing target cells, a driver line was used that contains the promoter for the DOPA decarboxylase gene (ddc-Ga14) which then allows transgene expression in a subset of neurons including dopaminergic neurons.

It was found that overexpression of mutant alpha-S did not affect the survival rate within the first 33 days, after that, however, flies overexpressing A56P alpha-S, and in particular TP alpha-S, had a higher morbidity resulting in an average reduction of the life span by approximately 10 days when compared to wt alpha-S flies (FIG. 3C and Tables 2 and 3). Furthermore, 25-30 day old flies expressing the designed mutants showed aberrant sleep patterns (FIG. 3D,E), which were strongest for flies expressing the A56P and TP alpha-S mutants, affecting both the sleep profiles and the average lengths of sleep bouts (FIG. 3D,E and FIGS. 12, 13). It is interesting to note that DA neurons in *Drosophila* innervate the mushroom body, a brain area involved in sleep regulation (Pitman et al., supra), and common features have been suggested between sleep states in insects and mammals (Shaw et al., supra)). Thus, flies expressing toxic variants of alpha-S might provide a means to investigate the mechanism underlying sleep impairment by genetic and pharmaceutical tools that in turn can be useful for developing PD therapy.

TABLE 2

| Comparison of Survival Curves | wt alpha-S and A56P alpha-S |
|---|---|
| Logrank Test | |
| Chi square | 5.270 |
| df | 1 |
| P value | 0.0217 |
| P value summary | * |
| Are the survival curves sig different? | Yes |
| Median survival | |
| Data 1:a-Syn-wt | 48.00 |
| Data 1:a-Syn-A56P | 42.00 |
| Ratio | 1.143 |
| 95% CI of ratio | 0.2754 to 2.010 |
| Hazard Ratio | |
| Ratio | 0.8769 |
| 95% CI of ratio | 0.6766 to 0.9697 |

TABLE 3

| Comparison of Survival Curves | wt alpha-S and TP alpha-S |
|---|---|
| Logrank Test | |
| Chi square | 47.74 |
| df | 1 |
| P value | P < 0.0001 |
| P value summary | *** |
| Are the survival curves sig different? | Yes |
| Median survival | |
| Data 1:a-syn(wt) | 48.00 |
| Data 1:a-syn(triple) | 42.00 |

TABLE 3-continued

| Comparison of Survival Curves | wt alpha-S and TP alpha-S |
|---|---|
| Ratio | 1.143 |
| 95% CI of ratio | 0.2733 to 2.012 |
| Hazard Ratio | |
| Ratio | 0.6946 |
| 95% CI of ratio | 0.4266 to 0.6217 |

Taken together the data demonstrate that over-expression of alpha-S variants, which delay fibril formation but allow oligomer formation, causes increased neurotoxicity in established model systems for PD: increasing impairment to form fibrils is consistently correlated with increasing neurodegeneration (wt~A30P<A56P<TP). The genetic mutant A53T alpha-S has a neurotoxicity comparable to that of A56P alpha-S in the three model systems, but does not allow a conclusion about the importance of a certain aggregate species for neurotoxicity as A53T alpha-S forms both oligomers and amyloid fibrils more rapidly. These results indicate that delayed fibril formation by the structure-based design mutants of alpha-S causes functional impairments in both *Drosophila* and *C. elegans*, that can be attributed to dopaminergic dysfunction. They alter mobility of flies and worms, affect the sleeping behaviour of flies and reduce their lifespan.

Example 5

Mammalian Neurons
Primary Neuronal Cultures

AAV-1/2 mosaic serotype viral vectors were prepared essentially as described (Nass & Blakely, supra). Their genomes consisted of AAV-2 ITRs, human synapsin-1 gene promoter driving expression of alpha-S variants, WPRE for enhanced mRNA stability and bovine growth hormone polyadenylation site.

Primary cortical and midbrain neurons were prepared from rat embryos at E18 or E16, respectively. Neurons were plated in 96 well plates for WST assay and tyrosine hydroxylase (TH) immunocytochemistry and in 24 well plates for NeuN immunocytochemistry. Neurons were transduced by AAV vectors at day 3 in vitro (DIV 3) and were analysed at DIV 10. WST assay, measuring mitochondrial dehydrogenase activity, was performed according to the protocol of the manufacturer (Roche Diagnostics). Immunocytochemistry was performed with anti-NeuN (Chemicon) and anti-TH antibodies (Advanced Immunochemicals Inc.) detected by Cy3 coupled secondary antibody. Cell counts were performed in at least 5 randomly selected fields per well and in at least 6 wells each of at least two independent replicates of respective transduction by AxioVision software (Zeiss).

To perform statistical analysis, respective groups were tested by Levene's test for equality of variances in order to confirm that One-Way ANOVA could be performed, for which Student-Newman-Keuls test for all pair wise comparisons was used. Data are presented as mean±standard error of the mean (SEM).

Results

We further investigated toxic effects of the alpha-S mutants upon expression in cultured mammalian neurons. Rat primary cortical neurons were transduced with Adeno-associated-virus (AAV) (Kugler et al. *Am J Hum Genet* 80, 291-297 (2007)) expressing wt or mutant alpha-S. Transgene expression was absolutely neuron-restricted and transduction efficacy was in the range of 95% as evidenced by EGFP fluorescence. Using a water-soluble tetrazolium salt (WST) colorimetric assay for mitochondrial dehydrogenase activity, we found that A56P alpha-S was more toxic than A53T alpha-S (which did not show significant differences to wt and A30P alpha-S, data not shown) and control neurons expressing EGFP (FIG. 4A). Furthermore, the TP alpha-S variant was significantly more cytotoxic than the A56P mutant (FIG. 4A). Since the WST colorimetric assay estimates not only the mitochondrial capacity to produce reduced equivalents but also the decline of mitochondrial activity due to diminished cell numbers, numbers of neurons by neuronal nuclei (NeuN) immunocytochemistry were also counted after expression of A53T, A56P and TP alpha-S variants as well as EGFP control protein. It was found that the TP mutant was again the most cytotoxic alpha-S species (FIG. 4A). However, while both A53T and A56P over-expression significantly reduced cortical neuron numbers as compared with EGFP over-expression, their effect was not statistically different from each other as in the WST assay, indicating that A56P might exert more subtle neurotoxic effects not directly leading to neurodegeneration as observed with the TP mutant. Finally, it was explored whether and which of the alpha-S mutants exerts a specific neurotoxic effect in dopaminergic neurons. Expression of A53T, A56P and TP alpha-S resulted in a lower mitochondrial dehydrogenase activity and a reduced number of surviving neurons than wt and A30P alpha-S and control neurons expressing EGFP (FIG. 4A). Similarly, in primary midbrain cultures the number of dopaminergic neurons was decreasing in the order EGFP≈wt≈A30P>A53T~A56P>TP (FIG. 4A). It is important to note that the genetic mutant A30P, in which the single proline mutation occurs outside the core of alpha-S fibrils, had a similar effect as wt and A53T alpha-S in cultured mammalian neurons (data not shown). This observation is consistent with a failure to detect neurodegeneration in transgenic mice overexpressing A30P alpha-S (Lee et al., supra).

A strong correlation between delayed formation of and lack of beta-sheet content in fibrils of alpha-S variants and the strength of PD-related behavioural effects of the alpha-S variants was found when expressed in animal models such as *Drosophila* and *C. elegans* and with increased neurotoxic effects on dopaminergic neurons of both *C. elegans* and mammals. These findings highlight the importance of pre-fibrillar, soluble alpha-S species in the pathogenesis and progression of PD and other neurodegenerative disorders collectively referred to as synucleinopathies and suggest that the inhibition of alpha-S mutants to form beta-sheets correlates with toxicity. Furthermore, the corresponding biological effects including the degree of toxicity in the different PD models used here suggest that structure-based design mutants of alpha-S provide a powerful tool for the identification of potential therapeutic compounds. In particular, the strong neurodegeneration exerted by TP alpha-S raises the possibility that cell death and neurodegeneration will be observed early on in rodent models of PD.

Example 6

Design of Alpha-S Variants

A design of alpha-S variants that aims at the production of toxic species should keep the structural and functional properties of the respective multimers nearly constant. The design was based on the conformational properties of the alpha-S monomer in solution (Bertoncini, C. W., et al. *Proc Natl Acad Sci USA* 102, 1430-1435 (2005)). V118 and M127A are hydrophobic residues that are located in the highly negatively charged C-terminal domain of alpha-S, which folds back onto the hydrophobic NAC region that is essential for aggregation of alpha-S into amyloid fibrils. To interfere with the intramolecular interaction between the C-terminal domain and the NAC region of alpha-S, which shields alpha-S from self association, V118 and M127 were replaced by alanine.

Cloning, Expression, and Purification of Alpha-S Variants

The following alpha-S variants were generated as described in Example 1: the single mutants M127A, V118A and the double mutant V118A+M127A. Based on the intramolecular interactions observed in monomeric alpha-S, these mutations are expected to cause a destabilization of the folding nucleus of alpha-S and lead to increased self-association.

NMR Spectroscopy

NMR samples contained ~0.2 mM 15N-labelled mutant alpha-S in 50 mM Na-phosphate buffer, 100 mM NaCl at pH 7.4 and 90% $H_2O$/10% $D_2O$. The experiments were recorded on a Bruker Avance 600 MHz NMR spectrometer. The temperature was set to 15° C. unless otherwise stated. Data processing was performed using the software packages Topspin (Bruker) and Sparky (Goddard, T. D., Kneller, D. G., University of California, San Francisco). For chemical shift analysis, 1H-15N Heteronuclear Single Quantum Coherene (HSQC) 2D spectra were recorded.

NMR spectroscopy showed that substitution of M127 and V118 by alanine or E or D does not induce rigid secondary or tertiary structure. Instead, the small chemical shift dispersion of NMR signals indicates that the variant alpha-Syn remains highly dynamic and samples a large ensemble of conformations.

*C. elegans* Experiments

The *C. elegans* experiments were carried out as described above in Example 4. FIG. 16 A clearly shows that worms expressing M127A alpha-S or A30P+A56P+A76P alpha-S are statistically more likely to show neurite defects in comparison to worms expressing either wild-type alpha-S or A30P alpha-S. This data is consistent to the results depicted in FIG. 16 B, showing a decreased slowing rate for worms expressing M127A alpha-S or A30P+A56P+A76P alpha-S in comparison to worms expressing either wild-type alpha-S or A30P alpha-S.

Yeast Experiments

Yeast cells were inoculated to an OD600 of 0.1 and incubated under alpha-S inducing conditions (SC-ura/Galactose). Total growth was measured at OD600 after 16 h of incubation. Three independent measurements were performed. Toxicity of the alpha-S variants can be judged by the growth impairment compared to vector control. FIG. 15 shows a strong impaired growth for yeast cells expressing M127A alpha-S and M127A+V118A alpha-S in comparison to the vector control, or cells expressing either wild-type alpha-S, A30P alpha-S, or A53T alpha-S.

Discussion

A better understanding of the relationship between the process of alpha-S amyloid formation and disease progression in animal models for Parkinson's disease is essential for understanding the molecular basis of neurodegeneration and the development of effective therapeutic strategies to prevent and treat PD and other synucleinopathies. We presented a structure-based rational design of alpha-S mutants and their biophysical properties in vitro. The results establish that alpha-S mutants that cause reduced fibrillization and beta-structure formation and lead to the formation of increased amounts of soluble oligomers can be predicted. We demonstrate that differences in the biophysical properties of these mutants translate into "predictable" changes in neuronal toxicity and behavioral defects in neuronal cell cultures and animal models of synucleinopathies. The structure-based design mutants provide unique tools to dissect the relative contribution of oligomers and fibrils to alpha-S toxicity and establish the relationship between biophysical properties of multimeric alpha-S species and their function in different in vivo models.

The rational design of the alpha-S variants was based on the flexibility of the alpha-S backbone in the monomeric state and the location of beta-strands in amyloid fibrils (Bertoncini et al., 2005, supra, Heise et al., 2005). The genetic mutation A30P is located in a domain that is statically disordered and not part of the core of amyloid fibrils of alpha-S. We carried the alanine-to-proline replacement right into the center of the beta-strands of amyloid fibrils of alpha-S (FIG. 1A). In agreement with the design principle, even the single point mutation A56P strongly reduced aggregation of alpha-S both in vitro (FIG. 2) and in living cells (FIG. 18). Assuming that only drastic differences in the rate of aggregation in vitro can be reliably transferred to the in vivo situation, the A56P mutation was complemented by the triple proline A30P/A56P/A76P mutation, which shows impaired formation of insoluble aggregates in vitro (FIG. 2) and in vivo (FIG. 19). At the same time, however, both the A56P and the A30P/A56P/A76P alpha-S variant showed a strongly increased propensity to form soluble oligomers (FIG. 17). In combination with wt alpha-S, the two structure-based design mutants allowed a detailed study of the relationship between oligomerization, fibril formation and neurotoxicity in animal models for PD.

HEK cells, rat primary neurons, *C. elegans* and *Drosophila* that over-express alpha-S are established models for PD. Here we over-expressed the wt protein, the genetic mutants A30P and A53T and the two structure-based design mutants A56P and TP alpha-S in all four of these model systems. The simultaneous use of four model systems was motivated by previous reports that over-expression of wt, genetic mutants and phosphorylation mimics of alpha-S induced different degrees of toxicity in different PD model systems. In contrast, expression of the structure-based design variants A56P and TP alpha-S caused increased neurotoxicity in all four model systems: increasing impairment to form fibrils was consistently correlated with increasing neurodegeneration (wt A30P<A56P<TP) (FIGS. 3 and 4). This provides strong evidence for the importance of soluble oligomers as the most toxic species in PD. In agreement with the importance of soluble oligomers for neurodegeneration, other studies have suggested that aggregation intermediates are the pathologically relevant species in Alzheimer and Huntington disease.

A mutational strategy as employed in our study allows correlations between biophysical properties observed for the mutated proteins in vitro and functional deficits observed in vivo. In agreement with the design principle, the most dramatic effect observed for the structure-based design variants of alpha-S was their impaired fibrillation but strongly enhanced formation of soluble oligomers. In agreement with this design principle, our studies showed that the A56P variant of αS has an affinity for phospholipid vesicles that is comparable and even slightly higher than A30P alpha-S (Table 1). Even for the triple-proline variant TP alpha-S an only slightly reduced vesicle-affinity (compared to A30P alpha-S) was observed, suggesting that the alpha-S variants are flexible enough to efficiently bind to phospholipid vesicles. Despite the very similar vesicle affinities, however, only the A56P and A30P/A56P/A76P variant of alpha-S showed a strongly increased neurotoxicity, consistent with their higher propensity to form soluble oligomers.

Our solid-state NMR data of late-stage aggregates of A56P and TP alpha-S showed that their morphology is similar to amyloid fibrils of wt alpha-S, however the molecular level structure is strongly changed. A dramatically diminished beta-sheet rich core was observed (FIG. 10), which suggests that soluble oligomers formed by the structure-based design variants might also have a reduced ability to adopt beta-structure. Importantly, neurotoxicity of variants of alpha-S (wt~A30P<A56P<TP alpha-S) in the four model systems for PD was inversely correlated with the amount of beta-structure detected in insoluble alpha-S aggregates (wt~A30P>A56P>TP alpha-S) (FIGS. 2, 4, 18). Thus formation of rigid beta-structure might not to be as important for neurotoxicity as previously thought.

In conclusion, our combined biophysical and in vivo data revealed a strong correlation between enhanced formation of soluble oligomers and lack of beta-sheet content in fibrils of alpha-S variants, and neurotoxicity, the strength of PD-related behavioural effects and survival in four model systems for PD. This provides strong evidence that structurally less stable aggregation intermediates of alpha-S are key players in the pathogenesis and progression of PD and other neurodegenerative disorders collectively referred to as synucleinopathies. The ability to engineer mutants that promote and stabilize specific toxic intermediates is essential not only for understanding the structural basis of alpha-S toxicity, but also for developing diagnostic tools and imaging agents.

LIST OF REFERENCES

US 2007/0192879
US 2007/0213253
WO 2008/063779
Bertoncini, C. W., Jung Y. S., Fernandez C. O., Hoyer W., Griesinger C. et al. Release of long-range tertiary interactions potentiates aggregation of natively unstructured alpha-synuclein. *Proc Natl Acad Sci USA* 102, 1430-1435 (2005).
Brenner, S. The genetics of *Caenorhabditis elegans*. *Genetics* 77, 71-94 (1974).
Edery, I., Zwiebel, L. J., Dembinska, M. E. & Rosbash, M. Temporal phosphorylation of the *Drosophila* period protein. *Proc Natl Acad Sci USA* 91, 2260-4 (1994).
Harada, R., Kobayashi, N., Kim, J, Nakamura, C., Han, S. W., Ikebukuro, K., Sode, K. The effect of amino acid substitution in the imperfect repeat sequences of alpha-synuclein of ibrillation. *Biochim. Biophys. Acta*, Epub July 2009.
Heise, H., Hoyer W., Becker S., Andronesi 0. C., Riedel D. et al. Molecular-level secondary structure, polymorphism, and dynamics of full-length alpha-synuclein fibrils studied by solid-state NMR. *Proc Natl Acad Sci USA* 102, 15871-15876 (2005).
Hendricks, J. C. et al. A non-circadian role for cAMP signaling and CREB activity in *Drosophila* rest homeostasis. *Nat Neurosci* 4, 1108-15 (2001).
Jones, J. A., Wilkins, D. K., Smith, L. J. & Dobson, C. M. Characterisation of protein unfolding by NMR diffusion measurements. *Journal of Biomolecular NMR* 10, 199-203 (1997).
Koo, H. J., Lee, H. J., Im, H. Sequence determinants regulating fibrillation of human alpha-synuclein. *Biochem Biophys Res Commun.* 368(3), 772-778(2008).
Koo, H. J., Choi, M. Y., Im, H. Aggregation-defective alpha-synuclein mutants inhibit the fibrillation of Parkinson's disease-linked alpha-synuclein variants. *Biochem. Biophys. Res. Commun.* 386(1): 165-169 (2009).
Kumar, S., Sarkar, A., Sundar D., Controlling aggregation propensity in A53T mutant of alpha-synuclein causing Parkinson's disease. *Biochem. Biophys. Res. Commun.*, Epub July 2009.

Kugler, S., Hahnewald R., Garrido M. & Reiss J. Long-term rescue of a lethal inherited disease by adeno-associated virus-mediated gene transfer in a mouse model of molybdenum-cofactor deficiency. *Am J Hum Genet* 80, 291-297 (2007).

Lashuel, H. A. & Lansbury P. T., Jr. Are amyloid diseases caused by protein aggregates that mimic bacterial pore-forming toxins? *Q Rev Biophys* 39, 167-201 (2006).

Lee, M. K., Stirling W., Xu Y., Xu X., Qui D. et al. Human alpha-synuclein-harboring familial Parkinson's disease-linked Ala-53-->Thr mutation causes neurodegenerative disease with alpha-synuclein aggregation in transgenic mice. *Proc Natl Acad Sci USA* 99, 8968-8973 (2002).

Marvanova, M. & Nichols, C. Identification of neuroprotective compounds of *Caenorhabditis elegans* dopaminergic neurons against 6-OHDA. *Journal of Molecular Neuroscience* 31, 127-137 (2007).

Masliah, E., Rockenstein E., Veinbergs I., Mallory M., Hashimoto M. et al. Dopaminergic loss and inclusion body formation in alpha-synuclein mice: implications for neurodegenerative disorders. *Science* 287, 1265-1269 (2000).

Nass, R. & Blakely R. D. The *Caenorhabditis elegans* dopaminergic system: opportunities for insights into dopamine transport and neurodegeneration. *Annu Rev Pharmacol Toxicol* 43, 521-544 (2003).

Pitman, J. L., McGill J. J., Keegan K. P. & Allada R. A dynamic role for the mushroom bodies in promoting sleep in *Drosophila*. *Nature* 441, 753-756 (2006).

Sawin, E. R., Ranganathan R. & Horvitz H. R. *C. elegans* locomotory rate is modulated by the environment through a dopaminergic pathway and by experience through a serotonergic pathway. *Neuron* 26, 619-631 (2000).

Shaw, P. J., Cirelli C., Greenspan R. J. & Tononi G. Correlates of sleep and waking in *Drosophila melanogaster*. *Science* 287, 1834-1837 (2000).

Ulrih, N. P., Barry, C. H. Fink, A. L. Impact of Tyr to Ala mutations on alpha-synuclein fibrillation and structural properties. *Biochim. Biophys. Acta* 1782(10): 581-585 (2008).

Zhou, W., Milder, J. B., Freed, C. R. Transgenic mice overexpressing tyrosine-to-cysteine mutant human alpha-synuclein: a progressive neurodegenerative model of diffuse Lewy body disease. *J Biol Chem*. 283(15), 9863-9870 (2008).

---

The invention claimed is:

1. A genetically engineered polynucleotide encoding an alpha-synuclein comprising at least 96% amino acid sequence identity to SEQ ID NO: 1, and having increased toxicity compared to wild-type alpha-synuclein having the amino acid sequence of SEQ ID NO: 1 wherein said toxicity is tested in a neuronal cell using an in vitro water soluble tetrazolium (WST) assay, and wherein the alpha-synuclein comprises at least one amino acid substitution at the alanine at position 56 (A56) and/or at the valine at position 118 (V118).

2. An expression vector comprising the polynucleotide of claim 1.

3. A cell comprising the polynucleotide according to claim 1, wherein the cell is a yeast cell, an invertebrate cell, or a vertebrate cell.

4. The cell of claim 3 wherein the invertebrate cell is a cell of *C. elegans* or a cell of *D. melanogaster*.

5. The cell of claim 3 wherein the vertebrate cell is a mammalian cell.

6. The cell of claim 5 wherein the mammalian cell is a mouse cell, a rat cell or a primate cell.

7. The cell of claim 5 wherein the mammalian cell is a non-human embryonic stem cell.

8. The cell of claim 5 wherein the mammalian cell is a dopaminergic neuronal cell.

* * * * *

SEQUENCE LISTING

<160> NUMBER OF SEQ ID NOS: 5

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 21
<212> TYPE: DNA
<213> ORGANISM: Artificial Sequence
<220> FEATURE:
<223> OTHER INFORMATION: Primer for determining the integration site in
      transgenic flies

<400> SEQUENCE: 2
actgaaatct gccaagaagt a                                          21

<210> SEQ ID NO 3

-continued

```
<211> LENGTH: 24
<212> TYPE: DNA
<213> ORGANISM: Artificial Sequence
<220> FEATURE:
<223> OTHER INFORMATION: Primer for the determination of the integration
      site in transgenic flies

<400> SEQUENCE: 3
gcaagaaagt atatctctat gacc                                          24

<210> SEQ ID NO 4
<211> LENGTH: 20
<212> TYPE: DNA
<213> ORGANISM: Artificial Sequence
<220> FEATURE:
<223> OTHER INFORMATION: forward primer for detection of alpha-synuclein

<400> SEQUENCE: 4
cagggtgtgg cagaagcagc                                               20

<210> SEQ ID NO 5
<211> LENGTH: 20
<212> TYPE: DNA
<213> ORGANISM: Artificial Sequence
<220> FEATURE:
<223> OTHER INFORMATION: reverse primer for detection of alpha-synuclein

<400> SEQUENCE: 5
ctgctgtcac acccgtcacc                                               20
```